US010254739B2

(12) United States Patent
Jones et al.

(10) Patent No.: US 10,254,739 B2
(45) Date of Patent: Apr. 9, 2019

(54) COIL POSITIONING SYSTEM

(71) Applicant: Mevion Medical Systems, Inc, Littleton, MA (US)

(72) Inventors: Mark R. Jones, Reading, MA (US); Mark Robinson, Littleton, MA (US); Ken Yoshiki Franzen, Acton, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 15/468,656

(22) Filed: Mar. 24, 2017

(65) Prior Publication Data

US 2017/0199506 A1   Jul. 13, 2017

Related U.S. Application Data

(63) Continuation-in-part of application No. 15/074,975, filed on Mar. 18, 2016, which is a continuation of
(Continued)

(51) Int. Cl.
*A61N 5/10* (2006.01)
*H05H 13/02* (2006.01)
(Continued)

(52) U.S. Cl.
CPC ........... *G05B 19/19* (2013.01); *A61N 5/1077* (2013.01); *H02K 7/08* (2013.01); *H02K 7/116* (2013.01);
(Continued)

(58) Field of Classification Search
USPC ....... 250/290–294, 298, 436, 396 R, 492.21, 250/492.3; 376/112, 121, 141, 142;
(Continued)

(56) References Cited

U.S. PATENT DOCUMENTS 498,915 A   6/1893  Heimann
2,280,606 A   4/1942  Roberts
(Continued)

FOREIGN PATENT DOCUMENTS

CA   2629333 A1   5/2007
CN   1537657 A   10/2004
(Continued)

OTHER PUBLICATIONS

US 8,581,524 B2, 11/2013, O'Neil et al. (withdrawn)
(Continued)

*Primary Examiner* — Wyatt A Stoffa
(74) *Attorney, Agent, or Firm* — Choate, Hall & Stewart LLP

(57) ABSTRACT

An example system includes: a magnet including one or more coils to conduct current to generate a magnetic field, with the magnetic field to affect output of radiation to a target; and one or more actuators, with an actuator among the one or more actuators being at least part of a physical coupling to the one or more coils, and with the actuator being controllable to move the one or more coils via the physical coupling based on movement of the magnet.

53 Claims, 43 Drawing Sheets

Related U.S. Application Data application No. 14/039,342, filed on Sep. 27, 2013, now Pat. No. 9,301,384.

(60) Provisional application No. 61/707,515, filed on Sep. 28, 2012.

(51) Int. Cl.
| | |
|---|---|
| *H04N 5/232* | (2006.01) |
| *H04N 5/225* | (2006.01) |
| *G05B 19/19* | (2006.01) |
| *H02K 7/08* | (2006.01) |
| *H02K 7/116* | (2006.01) |
| *H02K 11/215* | (2016.01) |
| *H02K 11/30* | (2016.01) |
| *H05H 7/04* | (2006.01) |
| *H05H 7/00* | (2006.01) |

(52) U.S. Cl.
CPC ........... *H02K 11/215* (2016.01); *H02K 11/30* (2016.01); *H05H 7/04* (2013.01); *H05H 13/02* (2013.01); *A61N 2005/1095* (2013.01); *G05B 2219/39221* (2013.01); *G05B 2219/40555* (2013.01); *H05H 2007/004* (2013.01)

(58) Field of Classification Search
USPC ............... 315/502, 503, 507; 313/62; 600/1
See application file for complete search history.

(56) References Cited

U.S. PATENT DOCUMENTS

| | | | |
|---|---|---|---|
| 2,492,324 A | 12/1949 | Salisbury |
| 2,615,129 A | 10/1952 | Mcmillan |
| 2,616,042 A | 10/1952 | Ray |
| 2,626,351 A | 1/1953 | Powell |
| 2,659,000 A | 11/1953 | Salisbury |
| 2,701,304 A | 2/1955 | Dickinson |
| 2,789,222 A | 4/1957 | Martin et al. |
| 2,812,463 A | 11/1957 | Teng et al. |
| 2,958,327 A | 11/1960 | Geissmann |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,883,761 A | 5/1975 | Hendry |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,095,201 A | 6/1978 | Kervizic et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,173 A | 4/1988 | Basil, Jr. et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |

(56) References Cited

U.S. PATENT DOCUMENTS

| | | |
|---|---|---|
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,625,331 A | 4/1997 | Yamada et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,717,371 A | 2/1998 | Crow |
| 5,726,448 A | 3/1998 | Smith et al. |
| 5,727,554 A | 3/1998 | Kalend et al. |
| 5,730,745 A | 3/1998 | Schulte et al. |
| 5,751,781 A | 5/1998 | Brown et al. |
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,963,615 A | 10/1999 | Egley et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,961 B1 | 12/2002 | Kirkpatrick |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,794,868 B1 | 9/2004 | Wong et al. |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,822,244 B2 | 11/2004 | Beloussov et al. |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |

(56) References Cited

U.S. PATENT DOCUMENTS

| | | |
|---|---|---|
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski et al. |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski et al. |
| 7,629,598 B2 | 12/2009 | Harada |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski et al. |
| 7,728,311 B2 | 6/2010 | Gall |
| 7,746,978 B2 | 6/2010 | Cheng et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,827,950 B2 | 11/2010 | Hu et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,801 B2 | 1/2011 | Tsotsis |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,906,769 B2 | 3/2011 | Blasche et al. |
| 7,914,734 B2 | 3/2011 | Livingston |

(56) References Cited

U.S. PATENT DOCUMENTS

| | | |
|---|---|---|
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,940,881 B2 | 5/2011 | Jongen et al. |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,111,125 B2 | 2/2012 | Antaya et al. |
| 8,129,699 B2 | 3/2012 | Balakin |
| 8,144,832 B2 | 3/2012 | Balakin |
| 8,173,981 B2 | 5/2012 | Trbojevic |
| 8,188,688 B2 | 5/2012 | Balakin |
| 8,198,607 B2 | 6/2012 | Balakin |
| 8,222,613 B2 | 7/2012 | Tajiri et al. |
| 8,227,768 B2 | 7/2012 | Smick et al. |
| 8,232,536 B2 | 7/2012 | Harada |
| 8,278,634 B2 | 10/2012 | Vanderberg et al. |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,378,299 B2 | 2/2013 | Frosien |
| 8,378,321 B2 | 2/2013 | Balakin |
| 8,382,943 B2 | 2/2013 | Clark |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,440,987 B2 | 5/2013 | Stephani et al. |
| 8,445,872 B2 | 5/2013 | Behrens et al. |
| 8,466,441 B2 | 6/2013 | Iwata et al. |
| 8,472,583 B2 | 6/2013 | Star-Lack et al. |
| 8,483,357 B2 | 7/2013 | Siljamaki et al. |
| 8,487,278 B2 | 7/2013 | Balakin |
| 8,502,173 B2 | 8/2013 | Vanderberg et al. |
| 8,552,406 B2 | 10/2013 | Phaneuf et al. |
| 8,552,408 B2 | 10/2013 | Hanawa et al. |
| 8,569,717 B2 | 10/2013 | Balakin |
| 8,581,125 B2 | 11/2013 | Chen |
| 8,581,215 B2 | 11/2013 | Balakin |
| 8,581,523 B2 | 11/2013 | Gall et al. |
| 8,581,525 B2 | 11/2013 | Antaya et al. |
| 8,643,314 B2 | 2/2014 | Touchi |
| 8,653,314 B2 | 2/2014 | Pelati et al. |
| 8,653,473 B2 | 2/2014 | Yajima |
| 8,791,656 B1 | 7/2014 | Zwart et al. |
| 8,927,950 B2 | 1/2015 | Gall et al. |
| 8,975,836 B2 | 3/2015 | Bromberg et al. |
| 9,155,186 B2 | 10/2015 | Zwart et al. |
| 9,185,789 B2 | 11/2015 | Zwart et al. |
| 9,301,384 B2 * | 3/2016 | Zwart ............. H05H 7/04 |
| 9,491,361 B2 * | 11/2016 | Beard ............. G02B 27/646 |
| 9,706,636 B2 * | 7/2017 | Zwart ............. H05H 7/04 |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0159795 A1 | 8/2004 | Kaercher et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0058245 A1 | 3/2005 | Ein-Gal |
| 2005/0089141 A1 | 4/2005 | Brown |
| 2005/0161618 A1 | 7/2005 | Pedroni |
| 2005/0184686 A1 | 8/2005 | Caporaso et al. |
| 2005/0228255 A1 | 10/2005 | Saracen et al. |
| 2005/0234327 A1 | 10/2005 | Saracen et al. |
| 2005/0247890 A1 | 11/2005 | Norimine et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0145088 A1 | 7/2006 | Ma |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0023699 A1 | 2/2007 | Yamashita et al. |
| 2007/0029510 A1 | 2/2007 | Hermann et al. |
| 2007/0051904 A1 | 3/2007 | Kaiser et al. |
| 2007/0061937 A1 | 3/2007 | Curle |
| 2007/0092812 A1 | 4/2007 | Caporaso et al. |
| 2007/0114945 A1 | 5/2007 | Mattaboni et al. |

(56) References Cited

U.S. PATENT DOCUMENTS

| | | | |
|---|---|---|---|
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0284548 A1 | 12/2007 | Kaiser et al. |
| 2008/0093567 A1 | 4/2008 | Gall |
| 2008/0218102 A1 | 9/2008 | Sliski et al. |
| 2009/0096179 A1 | 4/2009 | Stark et al. |
| 2009/0140671 A1 | 6/2009 | O'Neal, III et al. |
| 2009/0140672 A1 | 6/2009 | Gall et al. |
| 2009/0200483 A1 | 8/2009 | Gall et al. |
| 2010/0045213 A1 | 2/2010 | Sliski et al. |
| 2010/0230617 A1 | 9/2010 | Gall |
| 2011/0240874 A1 | 10/2011 | Iwata |
| 2011/0304416 A1 | 12/2011 | Warner et al. |
| 2012/0142538 A1 | 6/2012 | Antaya et al. |
| 2013/0009571 A1 | 1/2013 | Antaya |
| 2013/0053616 A1 | 2/2013 | Gall et al. |
| 2013/0127375 A1 | 5/2013 | Sliski et al. |
| 2013/0237425 A1 | 9/2013 | Leigh et al. |
| 2013/0249443 A1 | 9/2013 | Antaya et al. |
| 2013/0328475 A1 | 12/2013 | Hashimoto |
| 2014/0028220 A1 | 1/2014 | Bromberg et al. |
| 2014/0042934 A1 | 2/2014 | Tsutsui |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094638 A1 | 4/2014 | Gall et al. |
| 2014/0094639 A1* | 4/2014 | Zwart ............ H05H 7/04 600/1 |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0097920 A1 | 4/2014 | Goldie et al. |
| 2014/0320006 A1 | 10/2014 | Abs et al. |
| 2014/0371511 A1 | 12/2014 | Zwart et al. |
| 2016/0070270 A1* | 3/2016 | Beard ............ G02B 27/646 318/647 |
| 2016/0205760 A1* | 7/2016 | Zwart ............ H05H 7/04 315/502 |
| 2016/0316552 A1 | 10/2016 | Hashimoto |

FOREIGN PATENT DOCUMENTS

| | | |
|---|---|---|
| CN | 101061759 A | 10/2007 |
| CN | 101361156 A | 2/2009 |
| CN | 101932361 A | 12/2010 |
| CN | 101933405 A | 12/2010 |
| CN | 101933406 A | 12/2010 |
| CN | 102214494 A | 10/2011 |
| CN | 102387836 A | 3/2012 |
| CN | 104244562 A | 12/2014 |
| DE | 2753397 A1 | 6/1978 |
| DE | 3148100 A1 | 6/1983 |
| DE | 3530446 A1 | 3/1986 |
| DE | 4101094 C1 | 5/1992 |
| DE | 4411171 A1 | 10/1995 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0276123 A2 | 7/1988 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A2 | 8/1992 |
| EP | 0776595 A1 | 6/1997 |
| EP | 0864337 A2 | 9/1998 |
| EP | 0911064 A2 | 4/1999 |
| EP | 1069809 A1 | 1/2001 |
| EP | 1153398 A1 | 11/2001 |
| EP | 1294445 A2 | 3/2003 |
| EP | 1348465 A1 | 10/2003 |
| EP | 1358908 A1 | 11/2003 |
| EP | 1371390 A1 | 12/2003 |
| EP | 1402923 A1 | 3/2004 |
| EP | 1430932 A1 | 6/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1738798 A2 | 1/2007 |
| EP | 1826778 A2 | 8/2007 |
| EP | 1949404 A2 | 7/2008 |
| EP | 2183753 A1 | 5/2010 |
| EP | 2227295 A1 | 9/2010 |
| EP | 2232961 A1 | 9/2010 |
| EP | 2232962 A2 | 9/2010 |
| EP | 2363170 A1 | 9/2011 |
| EP | 2363171 A1 | 9/2011 |
| EP | 2394498 A2 | 12/2011 |
| EP | 2811813 A1 | 12/2014 |
| EP | 2814304 A1 | 12/2014 |
| EP | 3342462 A1 | 7/2018 |
| FR | 2560421 A1 | 8/1985 |
| FR | 2911843 A1 | 8/2008 |
| GB | 0957342 A | 5/1964 |
| GB | 1360085 A | 7/1974 |
| GB | 1485329 A | 9/1977 |
| GB | 2015821 A | 9/1979 |
| GB | 1583400 A | 1/1981 |
| GB | 2361523 A | 10/2001 |
| JP | S47-028762 U | 12/1972 |
| JP | U48-108098 | 9/1973 |
| JP | 57-162527 | 10/1982 |
| JP | 58-141000 | 8/1983 |
| JP | 61-225798 | 10/1986 |
| JP | 62-150804 | 7/1987 |
| JP | 62-186500 | 8/1987 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 06-036893 | 8/1994 |
| JP | 06-233831 | 8/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 10-071213 | 3/1998 |
| JP | 11-47287 | 2/1999 |
| JP | 11-102800 | 4/1999 |
| JP | 11-243295 | 9/1999 |
| JP | 2000-294399 A | 10/2000 |
| JP | 2001-6900 | 1/2001 |
| JP | 2001-009050 A | 1/2001 |
| JP | 2001-129103 A | 5/2001 |
| JP | 2001-346893 A | 12/2001 |
| JP | 2002-164686 A | 6/2002 |
| JP | 2003-517755 A | 5/2003 |
| JP | 2005-526578 A | 9/2005 |
| JP | 2006-036895 A | 2/2006 |
| JP | 2008-507826 A | 3/2008 |
| JP | 04-128717 B2 | 7/2008 |
| JP | 04-129768 B2 | 8/2008 |
| JP | 61-80800 | 1/2009 |
| JP | 2009-515671 A | 4/2009 |
| JP | 2009-516905 A | 4/2009 |
| JP | 04-273409 B2 | 6/2009 |
| JP | 2009-524201 A | 6/2009 |
| JP | 04-337300 B2 | 9/2009 |
| JP | 43-23267 B2 | 9/2009 |
| JP | 2011-505191 A | 2/2011 |
| JP | 2011-505670 A | 2/2011 |
| JP | 2011-507151 A | 3/2011 |
| JP | 05-046928 B2 | 10/2012 |

(56) References Cited

FOREIGN PATENT DOCUMENTS

| | | |
|---|---|---|
| JP | 05-341352 B2 | 11/2013 |
| JP | 2015-532509 A | 11/2015 |
| SU | 300137 | 11/1969 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| TW | 1401176 | 7/2013 |
| TW | 201422279 A | 6/2014 |
| TW | 201424466 A | 6/2014 |
| TW | 201429514 A | 8/2014 |
| TW | 201433331 A | 9/2014 |
| TW | 201434508 A | 9/2014 |
| WO | WO-86/07229 A1 | 12/1986 |
| WO | WO-90/12413 A1 | 10/1990 |
| WO | WO-92/03028 A1 | 2/1992 |
| WO | WO-93/02536 A1 | 2/1993 |
| WO | WO-98/17342 A2 | 4/1998 |
| WO | WO-1999/39385 A1 | 8/1999 |
| WO | WO-00/40064 A2 | 7/2000 |
| WO | WO-00/49624 A1 | 8/2000 |
| WO | WO-01/26230 A1 | 4/2001 |
| WO | WO-01/126569 | 4/2001 |
| WO | WO-02/07817 | 1/2002 |
| WO | WO-03/039212 A1 | 5/2003 |
| WO | WO-03092812 A1 | 11/2003 |
| WO | WO-2004026401 A1 | 4/2004 |
| WO | WO-2004101070 A1 | 11/2004 |
| WO | WO-2006012467 A2 | 2/2006 |
| WO | WO-2007/061937 A2 | 5/2007 |
| WO | WO-2007/084701 A1 | 7/2007 |
| WO | WO-2007130164 A2 | 11/2007 |
| WO | WO-2007145906 A2 | 12/2007 |
| WO | WO-2008/030911 A2 | 3/2008 |
| WO | WO-2008081480 A1 | 7/2008 |
| WO | WO-2009/048745 A2 | 4/2009 |
| WO | WO-2009/070173 A1 | 6/2009 |
| WO | WO-2009070588 A1 | 6/2009 |
| WO | WO-2009073480 A2 | 6/2009 |
| WO | WO-2009/80080 A1 | 7/2009 |
| WO | WO-2010089574 A2 | 8/2010 |
| WO | WO-2013098089 A1 | 7/2013 |
| WO | WO-2013/142409 A1 | 9/2013 |
| WO | WO-2013/0179311 A1 | 12/2013 |
| WO | WO-2014/018706 A1 | 1/2014 |
| WO | WO-2014/018876 A1 | 1/2014 |
| WO | WO-2014/052708 A2 | 4/2014 |
| WO | WO-2014/052716 A2 | 4/2014 |
| WO | WO-2014/052718 A2 | 4/2014 |
| WO | WO-2014/052719 A2 | 4/2014 |
| WO | WO-2014/052722 A2 | 4/2014 |

OTHER PUBLICATIONS

"510(k) Summary: Ion Beam Applications S.A.", FDA, Jul. 12, 2001, 5 pages.
"510(k) Summary: Optivus Proton Beam Therapy System", Jul. 21, 2000, 5 pages.
"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.
"Beam Delivery and Properties," Journal of the ICRU, 2007, 7(2):20 pages.
"CPAC Highlights Its Proton Therapy Program at ESTRO Annual Meeting", TomoTherapy Incorporated, Sep. 18, 2008, Madison, Wisconsin, pp. 1-2.
"Indiana's mega-million proton therapy cancer center welcomes its first patients" [online] Press release, Health & Medicine Week, 2004, retrieved from NewsRx.com, Mar. 1, 2004, pp. 119-120.
"LLNL, UC Davis Team Up to Fight Cancer," Lawrence Livermore National Laboratory, Apr. 28, 2006, SF-06-04-02, Livermore, California, pp. 1-4.
"Patent Assignee Search Paul Scherrer Institute," Library Services at Fish & Richardson P.C., Mar. 20, 2007, 40 pages.
"Patent Prior Art Search for 'Proton Therapy System'," Library Services at Fish & Richardson P.C., Mar. 20, 2007, 46 pages.
"Superconducting Cyclotron Contract" awarded by Paul Scherrer Institute (PSI), Villigen, Switzerland, http://www.accel.de/News/superconducting_cyclotron_contract.htm, Jan. 2009, 1 page.
"The Davis 76-Inch Isochronous Cyclotron", Beam on: Crocker Nuclear Laboratory, University of California, 2009, 1 page.
"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.
"The K250 Proton therapy Cyclotron," National Superconducting Cyclotron Laboratory at Michigan State University (NSCL), retrieved from: http://www.nscl.msu.edu/tech/accelerators/k250.html , Feb. 2005, 2 pages.
18th Japan Conference on Radiation and Radioisotopes [Japanese], Nov. 25-27, 1987, 9 pages.
Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.
Abrosimov, N.K., et al., "Neutron Time-of-Flight Spectrometer Gneis at the GatchinalGeV Proton Synchrocyclotron", Lemingrad Nuclear Physics Institute, USSR, 1985.
Adachi et al., "A 150MeV FFAG Synchrotron with "Return-Yoke Free" Magent," Proceedings of the 2001 Particle Accelerator Conference, Chicago, 2001, 3 pages.
Ageyev et al., "The IHEP Accelerating and Storage Complex (UNK) Status Report," 11th International Conference on High-Energy Accelerators, 1980, pp. 60-70.
Agosteo et al., "Maze Design of a gantry room for proton therapy, " Nuclear Instruments & Methods in Physics Research, 1996, Section A, 382, pp. 573-582.
Alexeev et al., "R4 Design of Superconducting Magents for Proton Synchrotrons," Proceedings of the Fifth International Cryogenic Engineering Conference, 1974, pp. 531-533.
Allardyce et al., "Performance and Prospects of the Reconstructed CERN 600 MeV Synchrocyclotron," IEEE Transactions on Nuclear Science USA, Jun. 1977, ns-24:(3) 1631-633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" Nuclear Instruments and Methods in Physics Research A, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference,2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators," Journal for All Engineers Interested in the Nuclear Field, 1967, pp. 10-16 (1967) [Lang.: German], English bibliographic information (http://www.osti.gov/energycitations/product.biblio.jsp?osti_id=4442292).
Arduini et al. "Physical specifications of clinical proton beams from a synchrotron," Med. Phys, Jun. 1996, 23 ( 6): 939-951.
Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," Nuclear Instruments and Methods in Physics Research B56/57, 1991, pp. 1201-1204.

(56) References Cited

OTHER PUBLICATIONS

Bellomo et al., "The Superconducting Cyclotron Program at Michigan State University," Bulletin of the American Physical Society, Sep. 1980, 25(7):767.
Benedikt and Carli, "Matching to Gantries for Medical Synchrotrons" IEEE Proceedings of the 1997 Particle Accelerator Conference, 1997, pp. 1379-1381.
Bieth et al., "A Very Compact Protontherapy Facility Based on an Extensive Use of High Temperature Superconductors (HTS)" Cyclotrons and their Applications 1998, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, IEEE, 1979, pp. 1923-1926.
Blackmore et al., "Operation of the Triumf Proton Therapy Facility," IEEE Proceedings of the 1997 Particle Accelerator Conference, May 12-16, 19973:3831-3833.
Bloch, "The Midwest Proton Therapy Center," Application of Accelerators in Research and Industry, Proceedings of the Fourteenth Int'l Conf, Part Two, Nov. 1996, pp. 1253-1255.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11th International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Problems and Accomplishments of Superconducting Cyclotrons," Proceedings of the 14th International Conference, Cyclotrons and Their Applications, Oct. 1995, pp. 674-684.
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "Superconducting Cyclotron for Medical Application", IEEE Transactions on Magnetics, Mar. 1989, 25(2): 1746-1754.
Blosser et al., "Superconducting Cyclotrons", Seventh International Conference on Cyclotrons and their Applications, Aug. 19-22, 1975, pp. 584-594.
Blosser, "Application of Superconductivity in Cyclotron Construction," Ninth International Conference on Cyclotrons and their Applications, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, the Sixth International Cyclotron Conference, 1972, pp. 16-32.
Blosser, "Medical Cyclotrons," Physics Today, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," Bulletin of the American Physical Society, Apr. 1981, 26(4):558.
Blosser, "Synchrocyclotron Improvement Programs," IEEE Transactions on Nuclear Science USA, Jun. 1969, 16(3):Part I, pp. 405-414.
Blosser, "The Michigan State University Superconducting Cyclotron Program," Nuclear Science, Apr. 1979, NS-26(2):2040-2047.
Blosser, H., Present and Future Superconducting Cyclotrons, Bulletin of the American Physical Society, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," IEEE Transactions on Nuclear Science, 1977, NS-24(3): 1118-1120.
Chichili et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chong et al., Radiology Clinic North American 7, 3319, 1969, 27 pages.
Chu et al., "Instrumentation for Treatment of Cancer Using Proton and Light-ion Beams," Review of Scientific Instruments, Aug. 1993, 64 (8):2055-2122.
Chu et al., "Performance Specifications for Proton Medical Facility," Lawrence Berkeley Laboratory, University of California, Mar. 1993, 128 pages.
Chu, "Instrumentation in Medical Systems," Accelerator and Fusion Research Division, Lawrence Berkeley Laboratory, University of California, Berkeley, CA, May 1995, 9 pages.
Cohen, R. et al., "Nevis Synchrocyclotron Conversion Project", IEEE Transactions on Nuclear Science, IEEE Service Center, New York, NY, US, vol. 16, No. 3, Jun. 1, 1969, pp. 421425, XP011351570, ISSN: 0018-9499, DOI: 10.1109/TNS.1969.4325264 abstract; figures I-4aChap. 1, p. 421-2; chap. 11 from p. 423, col. 2 top. 425, col. 1. (5 pages).
Cole et al., "Design and Application of a Proton Therapy Accelerator," Fermi National Accelerator Laboratory, IEEE, 1985, 5 pages.
Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," Proceedings of EPAC, 2002, pp. 560-562.
C/E Source of Ions for Use in Sychro-Cyclotrons Search, Jan. 31, 2005, 9 pages.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Cosgrove et al., "Microdosimetric Studies on the Orsay Proton Synchrocyclotron at 73 and 200 MeV," Radiation Protection Dosimetry, 1997, 70(1-4):493-496.
Coupland, "High-field (5 T) pulsed superconducting dipole magnet," Proceedings of the Institution of Electrical Engineers, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," Medical Physics, Nov./Dec. 1991, 18(6):1093-1099.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dey, M.K., et al., "Coil Centering for the Kolkata Superconducting Cyclotron Magnet", Cyclotrons and their applications, Proceedings, 18th International Conference, Cyclotrons 2007, Giardini Naxo, Italy, Oct. 1-5, 2007 (3 pages).
Dialog Search, Jan. 31, 2005, 17 pages.
Dugan et al., "Tevatron Status" IEEE, Particle Accelerator Conference, Accelerator Science & Technology, 1989, pp. 426-430.

(56) References Cited

OTHER PUBLICATIONS

Eickhoff et al., "The Proposed Accelerator Facility for Light Ion Cancer Therapy in Heidelberg," Proceedings of the 1999 Particle Accelerator Conference, New York, 1999, pp. 2513-2515.
Elo, Don, et al., "Mechanical Design of Regenerative Deflector for the Berkeley 88-Inch Cyclotron", Proceedings of the International Conference on Isochronous Cyclotrons, Gatlinburg, Tennessee, Aug. 1966 (7 pages).
Enchevich et al., "Minimizing Phase Losses in the 680 MeV Synchrocyclotron by Correcting the Accelerating Voltage Amplitude," Atomnaya Energiya, 1969, 26:(3):315-316.
Endo et al., "Compact Proton and Carbon Ion Synchrotrons for Radiation Therapy," Proceedings of EPAC 2002, Paris France, 2002, pp. 2733-2735.
First Office Action (Chinese translation) for CN 201380062116.1, 16 pages (dated Dec. 5, 2016).
First Office Action (English translation) for CN 201380062116.1, 24 pages (dated Dec. 5, 2016).
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flanz et al., "Treating Patients with the Nptc Accelerator Based Proton Treatment Facility," Proceedings of the 2003 Particle Accelerator Conference, 2003, pp. 690-693.
Flood and Frazier, . "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," IEEE Transactions on Applied Superconductivity, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, 995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman, et. al. "Proton radiotherapy with the Uppsala cyclotron. Experience and plans" Strahlentherapie, 1985, 161(12):764-770.
Graffman, S., et al., Clinical Trials in Radiotherapy and the Merits of High Energy Protons, Acta Radiol. Therapy Phys. Biol. 9:1-23 (1970).
Hede, "Research Groups Promoting Proton Therapy "Lite,"" Journal of the National Cancer Institute, Dec. 6, 2006, 98(23):1682-1684.
Heinz, "Superconducting Pulsed Magnetic Systems for High-Energy Synchrotrons," Proceedings of the Fourth International Cryogenic Engineering Conference, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," International Journal of Radiation Oncology Biology Physics, vol. 3 complete, 1977, pp. 387-391.
Hirabayashi, "Development of Superconducting Magnets for Beam Lines and Accelerator at KEK," IEEE Transaction on Magnetics, Jan. 1981, Mag-17(1):728-731.
International Preliminary Report on Patentability from PCT application PCT/US2013/062117 dated Apr. 9, 2015 (11 pages).
International Search Report and Written Opinion dated Jun. 10, 2014 from PCT application No. PCT/US2013/062102 (12 pages).
International Search Report and Written Opinion dated May 26, 2014 from corresponding PCT application No. PCT/US2013/062117 (14 pages).
Invitation to pay additional fees and, where applicable, protest fee dated Nov. 25, 2013 from corresponding PCT application No. PCT/US2013/062117 (5 pages) (including attached search report).
Ishibashi and Mcinturff, "Stress Analysis of Superconducting 10T Magnets for Synchrotron," Proceedings of the Ninth International Cryogenic Engineering Conference, May 11-14, 1982, pp. 513-516.
Ishibashi and Mcinturff, "Winding Design Study of Superconducting 10 T Dipoles for a Synchrotron," IEEE Transactions on Magnetics, May 1983, MAG-19(3):1364-1367.
Jahnke et al., "First Superconducting Prototype Magnets for a Compact Synchrotron Radiation Source in Operation," IEEE Transactions on Magnetics, Mar. 1988, 24(2):1230-1232.
Jones and Dershem, "Synchrotron Radiation from Proton in a 20 TEV, 10 TESLA Superconducting Super Collider" Proceedings of the 12th International Conference on High-Energy Accelerator, Aug. 11-16, 1983, pp. 138-140.
Jones and Mills, "The South African National Accelerator Centre: Particle Therapy and Isotope Production Programmes," Radiation Physics and Chemistry, Apr.-Jun. 1998, 51(4-6):571-578.
Jones et al., "Status Report of the NAC Particle Therapy Programme," Stralentherapie and Onkologie, vol. 175, Suppl. II, Jun. 1999, pp. 30-32.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jongen et al., "Development of a Low-cost Compact Cyclotron System for Proton Therapy," National Institute of Radiol.. Sci,1991, No. 81, pp. 189-200.
Jongen et al., "Progress report on the IBA-SHI small cyclotron for cancer therapy" Nuclear Instruments and Methods in Physics Research, Section B, vol. 79, issue 1-4, 1993, pp. 885-889.
Jongen et al., "The proton therapy system for MGH's NPTC: equipment description and progress report," Bulletin du Cancer/Radiotherapie, Proceedings of the meeting of the European Heavy Particle Therapy Group, 1996, 83(Suppl. 1):219-222.
Jongen et al., "The proton therapy system for the NPTC: Equipment Description and progress report," Nuclear Instruments and methods in physics research, 1996, Section B, 113(1): 522-525.
Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," Med. Radial., Moscow, 28(3):28-32 (Mar. 1983)(German with English Abstract on end of p. 32).
Kats and Druzhinin, "Comparison of Methods for Irradiation Prone Patients," Atomic Energy, Feb. 2003, 94(2): 120-123.
Kats and Onosovskii, "A Simple, Compact, Flat System for the Irradiation of a Lying Patient with a Proton Beam from Different Directions," Instruments and Experimental Techniques, 1996, 39(1): 132-134.
Kats and Onosovskii, "A Planar Magnetooptical System for the Irradiation of a Lying Patient with a Proton Beam from Various Directions," Instruments and Experimental Techniques, 1996, 39(1):127-131.

(56) References Cited

OTHER PUBLICATIONS

Khoroshkov et al.," Moscow Hospital-Based Proton Therapy Facility Design," Am. Journal Clinical Oncology: CCT, Apr. 1994, 17(2):109-114.
Kim and Blosser, "Optimized Magnet for a 250 MeV Proton Radiotherapy Cyclotron," Cyclotrons and Their Applications 2001, May 2001, Sixteenth International Conference, pp. 345-347.
Kim and Yun, "A Light-Ion Superconducting Cyclotron System for Multi-Disciplinary Users," Journal of the Korean Physical Society, Sep. 2003, 43(3):325-331.
Kim et al., "Construction of 8T Magnet Test Stand for Cyclotron Studies," IEEE Transactions on Applied Superconductivity, Mar. 1993, 3(1):266-268.
Kim et al., "Design Study of a Superconducting Cyclotron for Heavy Ion Therapy," Cyclotrons and Their Applications 2001, Sixteenth International Conference, May 13-17, 2001, pp. 324-326.
Kim et al., "Trim Coil System for the Riken Cyclotron Ring Cyclotron," Proceedings of the 1997 Particle Accelerator Conference, IEEE, Dec. 1981, vol. 3, pp. 214-235 or 3422-3424, 1998.
Kim, "An Eight Tesla Superconducting Magnet for Cyclotron Studies," Ph.D. Dissertation, Michigan State University, Department of Physics and Astronomy, 1994, 138 pages.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the Riken SSC (II)," Scientific Papers of the Institute of Physical and Chemical Research, Dec. 1981, 75(4):214-235.
Koehler et al., "Range Modulators for Protons and Heavy Ions," Nuclear Instruments and Methods, 1975, vol. 131, pp. 437-440.
Koto and Tsujii. "Future of Particle Therapy," Japanese Journal of Cancer Clinics, 2001, 47(1):95-98 [Lang.: Japanese], English abstract (http://sciencelinks.jp/j-east/article/200206/000020020601A0511453.php).
Kraft et al., "Hadrontherapy in Oncology," U. Amaldi and Larrsson, editors Elsevier Science, 1994, 390 pages.
Krevet et al., "Design of a Strongly Curved Superconducting Bending Magnet for a Compact Synchrotron Light Source," Advances in Cryogenic Engineering, 1988, vol. 33, pp. 25-32.
Laisne et al., "The Orsay 200 MeV Synchrocyclotron," IEEE Transactions on Nuclear Science, Apr. 1979, NS-26(2):1919-1922.
Larsson et al., Nature,1958, 182:1222.
Larsson, "Biomedical Program for the Converted 200-MeV Synchrocyclotron at the Gustaf Werner Institute," Radiation Research, 1985, 104:S3I O-S3 I 8.
Lawrence et al., "Heavy particles in acromegaly and Cushing's Disease," in Endocrine and Norendocrine Hormone Producing Tumors (Year Book Medical Chicago, 1973, pp. 29-61.
Lawrence et al., "Successful Treatment of Acromegaly: Metabolic and Clinical Studies in 145 Patients," The Journal of Clinical Endrocrinologu and Metabolism, Aug. 1970, 31(2), 21 pages.
Lawrence et al., "Treatment of Pituitary Tumors," (Excerpta medica, Amsterdam/American Elsevier, New York, 1973, pp. 253-262.
Lawrence, J.H., Proton Irradiation of the Pituitary Cancer, vol. 10, pp. 795-798 (1957).
Lecroy et al., "Viewing Probe for High Voltage Pulses," Review of Scientific Instruments USA, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Search and Keyword Search for Synchrocyclotron, Jan. 25, 2005, 68 pages.
Literature Search, Jan. 26, 2005, 36 pages.
Literature Author and Keyword Search, Feb. 14, 2005, 44 pages.
Literature Keyword Search, Jan. 24, 2005, 98 pages.
Literature Search by Company Name/Component Source, Jan. 24, 2005, 111 pages.
Livingston et al., "A capillary ion source for the cyclotron," Review Science Instruments, Feb. 1939, 10:63.
Mandrillon, "High Energy Medical Accelerators," EPAC 90, 2nd European Particle Accelerator Conference, Jun. 12-16, 1990, 2:54-58.
Marchand et al., "IBA Proton Pencil Beam Scanning: an Innovative Solution for Cancer Treatment," Proceedings of EPAC 2000, Vienna, Austria, 3 pages.
Marti et al., "High Intensity Operation of a Superconducting Cyclotron," Proceedings of the 14th International Conference, Cyclotrons and Their Applications, Oct. 1995, pp. 45-48 (Oct. 1995).
Martin, "Operational Experience with Superconducting Synchrotron Magnets" Proceedings of the 1987 IEEE Particle Accelerator Conference, Mar. 16-19, 1987, vol. 3 of 3: 1379-1382.
Meote et al., "ETOILE Hadrontherapy Project, Review of Design Studies" Proceedings of EPAC 2002, 2002, pp. 2745-2747.
Miyamoto et al., "Development of the Proton Therapy System," The Hitachi Hyoron, 79(10):775-779 (1997) [Lang: Japanese], English abstract (http://www.hitachi.com/rev/1998/revfeb98/rev4 706.htm).
Montelius et al., "The Narrow Proton Beam Therapy Unit at the Svedberg Laboratory in Uppsala," Acta Oncologica, 1991, 30:739-745.
Moser et al., "Nonlinear Beam Optics with Real Fields in Compact Storage Rings," Nuclear Instruments & Methods in Physics Research/ Section B, B30, Feb. 1988, No. 1, pp. 105-109.
Moyers et al., "A Continuously Variable Thickness Scatterer for Proton Beams Using Self-compensating Dual Linear Wedges" Loma Linda University Medical Center, Dept. of Radiation Medicine, Loma Linda, CA, Nov. 2, 1992, 21 pages.
N.F. Verster: "Regenerative Beam Extraction from the 150-MeV Synchrocyclotron at the Laboratoire Curie", Proceedings of Sector-Focused Cyclotrons 1959, 1959, pp. 224-229 (6 pages).
National Cancer Institute Funding (Senate—Sep. 21, 1992) (www.thomas.loc.gov/egi-bin/query/z?r102:S21SE2-712 (2 pages).
Nicholson, "Applications of Proton Beam Therapy," Journal of the American Society of Radiologic Technologists, May/Jun. 1996, 67(5): 439-441.
Nolen et al., "The Integrated Cryogenic—Superconducting Beam Transport System Planned for MSU," Proceedings of the 12th International Conference on High-Energy Accelerators, Aug. 1983, pp. 549-551.
Norimine et al., "A Design of a Rotating Gantry with Easy Steering for Proton Therapy," Proceedings of EPAC 2002, 2002, pp. 2751-2753.
Notice of Allowance for U.S. Appl. No. 15/074,975, 41 pages (dated May 1, 2017).
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," Japanese Journal of Cancer Clinics, 1997, 43(2):209-214 [Lang.: Japanese].
Okumura et al., "Proton Radiotherapy" Japanese Journal of Cancer and Chemotherapy, 1993, 10. 20(14):2149-2155[Lang.: Japanese].
Ormrod, J.H., et al, "Status of the Chalk-River Superconducting Heavy-Ion Cyclotron", Proceedings of 9th International Conference on Cyclotrons and their Applications '81, 1981 (9 pages).
Ormrod, J.H., et al., "The Chalk-River Superconducting Cyclotron", Proceedings of 8th International Conference on Cyclotrons and their applications '79, 1979 (6 pages).
Outstanding from Search Reports, "Accelerator of Polarized Portons at Fermilab," dated 2005, 20 pages.
Paganetti et al., "Proton Beam Radiotherapy—The State of the Art," Springer Verlag, Heidelberg, ISBN 3-540-00321-5, Oct. 2005,36 pages.
Palmer and Tollestrup, "Superconducting Magnet Technology for Accelerators," Annual Review of Nuclear and Particle Science, 1984, vol. 34, pp. 247-284.
Patent Assignee and Keyword Searches for Synchrocyclotron, Jan. 25, 2005, 78 pages.

(56) References Cited

OTHER PUBLICATIONS

Pavlovic, "Beam-optics study of the gantry beam delivery system for light-ion cancer therapy," Nuclear Instruments and Methods in Physics Research, Section A, Nov. 1997, 399(2):439-454(16).
Pedroni and Enge, "Beam optics design of compact gantry for proton therapy" Medical & Biological Engineering & Computing, May 1995, 33(3):271-277.
Pedroni and Jermann, . "SGSMP: Bulletin Mar. 2002 Proscan Project, Progress Report on the PROSCAN Project of PSI" [online] retrieved from www.sgsmp.ch/protA23.htm, Mar. 2002, 5 pages.
Pedroni et al., "A Novel Gantry for Proton Therapy at the Paul Scherrer Institute," Cycloctrons and Their Applications 2001: Sixteenth International Conference. AIP Conference Proceedings, 2001, 600:13-17.
Pedroni et al., "The 200-MeV proton therapy project at the Paul Scherrer Institute: Conceptual design and practical realization," Medical Physics, Jan. 1995, 22(1):37-53.
Pedroni, "Accelerators for Charged Particle Therapy: Performance Criteria from the User Point of View," Cyclotrons and their Applications, Proceedings of the 13th International Conference, Jul. 6-10, 1992, pp. 226-233.
Pedroni, "Latest Developments in Proton Therapy" Proceedings of EPAC 2000, 2000, pp. 240-244.
Pedroni, "Status of Proton Therapy: results and future trends," Paul Scherrer Institute, Division of Radiation Medicine, 1994, 5 pages.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" Medical Physics, Sep./Oct. 1988, 15(5):798.
Pourrahimi et al., "Powder Metallurgy Processed Nb3Sn(Ta) Wire for High Field NMR magnets," IEEE Transactions on Applied Superconductivity, Jun. 1995, 5(2):1603-1606.
Prieels et al., "The IBA State-of-the-Art Proton Therapy System, Performances and Recent Results," Application of Accelerators in Research and industry—Sixteenth Int'l Conj, American Institute of Physics, Nov. 1-5, 2000, 576:857-860.
Prosecution History of U.S. Appl. No. 14/039,073 (downloaded Jul. 17, 2014).
Rabin et al., "Compact Designs for Comprehensive Proton Beam Clinical Facilities," Nuclear Instruments & Methods in Physics Research, Apr. 1989, Section B, vol. 40-41, Part II, pp. 1335-1339.
Rainwater, James, "Status of the Nevis Synchrocyclotron Modification", AIP Conference Proceedings No. 9, 1972 (14 pages).
Research & Development Magazine. "Proton Therapy Center Nearing Completion," Aug. 1999, 41(9): 2 pages (www.rdmag.com).
Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.
Rifuggiato et, al., "Status Report of the LNS Superconducting Cyclotron" Nukleonika, 2003, 48: SI31-S134, Supplement 2.
Rode, "Tevatron Cryogenic System," Proceedings of the 12th International Conference on High-ener5'Y Accelerators, Fermilab, Aug. 11-16, 1983, pp. 529-535.

Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesforsch. Fuer Forsch. U. Technol. In German; English Summary.
Schillo et al,. "Compact Superconducting 250 MeV Proton Cyclotron for the PSI Proscan Proton Therapy Project," Cyclotrons and Their Applications 2001, Sixteenth International Conference, 2001, pp. 37-39.
Schneider et al., "Nevis Synchrocyclotron Conversion Program—RF System," IEEE Transactions on Nuclear Science USA, Jun. 1969, ns 16( 3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," Application of Accelerators in Research and Industry, American Institute of Physics, Proceedings of the Fifteenth International Conference, Nov. 1998, Part Two, pp. 963-966.
Schreuder, "Recent Developments in Superconducting Cyclotrons," Proceedings of the 1995 Particle Accelerator Conference, May 1-5, 1995, vol. 1, pp. 317-321.
Schubert and Blosser, "Conceptual Design of a High Field Ultra-Compact Cyclotron for Nuclear Physics Research," Proceedings of the 1997 Particle Accelerator Conference, May 12-16, 1997, vol. 1, 3 pp. 1060-1062.
Schubert, "Extending the Feasibility Boundary of the Isochronous Cyclotron," Dissertation submitted to Michigan State University, 1997, Abstract http://adsabs.harvard.edu/abs/1998PhDt.......147S.
Shelaev et al., "Design Features of a Model Superconducting Synchrotron of JINR," Proceedings of the 12th International Conference on High-energy Accelerators, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/1 1 0001493249/en/.
Sisterson, "World Wide Proton Therapy Experience in 1997," The American Institute of Physics, Applications of Accelerators in Research and Industry, Proceedings of the Fifteenth International Conference, Part Two, Nov. 1998, pp. 959-962.
Sisterson, "Clinical use of proton and ion beams from a world-wide perspective," Nuclear Instruments and Methods in Physics Research, Section B, 1989, 40-41:1350-1353.
Slater et al., "Development of a Hospital-Based Proton Beam Treatment Center," International Journal of Radiation Oncology Biology Physics, Apr. 1988, 14(4):761-775.
Slater et al., "Developing a Clinical Proton Accelerator Facility: Consortium-Assisted Technology Transfer," Conference Record of the 1991 IEEE Particle Accelerator Conference: Accelerator Science and Technology, vol. I, May 6-9, 1991, pp. 532-536.
Smith et al., "The Northeast Proton Therapy Center at Massachusetts General Hospital" Journal of Brachytherapy International, Jan. 1997, pp. 137-139.
Snyder and Marti, "Central region design studies for a proposed 250 MeV proton cyclotron," Nuclear Instruments and Methods in Physics Research, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" Proceedings of the 2003 Particle Accelerator Conference, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Tadashi et al., "Large superconducting super collider (SSC) in the planning and materials technology," 1992, 78(8):1305-1313, The Iron and Steel Institute of Japan 00211575.

(56) References Cited

OTHER PUBLICATIONS

Takada, "Conceptual Design of a Proton Rotating Gantry for Cancer Therapy," Japanese Journal of Medical Physics, 1995, 15(4):270-284.
Takayama et al., "Compact Cyclotron for Proton Therapy," Proceedings of the 8th Symposium on Accelerator Science and Technology, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly et al., "Development and verification of the pulsed scanned proton beam at the Svedberg Laboratory in Uppsala," Phys. Med. Biol., 2007, 52:2741-2754.
Tilly, et al., "Development and verification of the pulsed scanned proton beam at the Svedberg Laboratory in Uppsala", Physics in Medicine and Biology, Phys. Med. Biol. 52, pp. 2741-2454 (2007).
Tobias et al., Cancer Research,1958, 18, 121 (1958).
Tom, "The Use of Compact Cyclotrons for Producing Fast Neutrons for Therapy in a Rotatable Isocentric Gantry," IEEE Transaction on Nuclear Science, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," Nuclear Instruments and Methods in Physics Research, Section A, 1986, vol. 244, pp. 273-282.
Tsuji, "The Future and Progress of Proton Beam Radiotherapy," *Journal of Japanese Society for Therapeutic Radiology and Oncology* , 1994, 6(2):63-76.
U.S. Appl. No. 13/830,792, filed Mar. 14, 2013.
U.S. Appl. No. 13/949,459, filed Jul. 24, 2013.
U.S. Appl. No. 61/676,377, filed Jul. 27, 2012.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003_04_ 104.pdf or http://www.hitachi.com/rev/archive/2003/2005649_12606.html (full text) [Hitachi, 52(4), Dec. 2003].
Umezawa et al., "Beam Commissioning of the new Proton Therapy System for University of Tsukuba," Proceedings of the 2001 Particle Accelerator Conference, vol. 1, Jun. 18-22, 2001, pp. 648-650.
van Steenbergen, "Superconducting Synchroton Development at BNL," Proceedings of the 8th International Conference on High-Energy Accelerators CERN 1971, 1971, pp. 196-198.
van Steenbergen, "The CMS, a Cold Magnet Synchrotron to Upgrade the Proton Energy Range of the BNL Facility," IEEE Transactions on Nuclear Science, Jun. 1971, 18(3):694-698.
Vandeplassche et al., "235 MeV Cyclotron for MGH's Northeast Proton Therapy Center (NPTC): Present Status," EPAC 96, Fifth European Partical Accelerator Conference, vol. 3, Jun. 10-14, 1996, pp. 2650-2652.
Vorobiev et al., "Concepts of a Compact Achromatic Proton Gantry with a Wide Scanning Field", Nuclear Instruments and Methods in Physics Research, Section A., 1998, 406(2):307-310.
Vrenken et al., "A Design of a Compact Gantry for Proton Therapy with 2D-Scanning," Nuclear Instruments and Methods in Physics Research, Section A, 1999, 426(2):618-624.
Wikipedia, "Cyclotron" http://en.wikipedia.org/wiki/Cyclotron (originally visited Oct. 6, 2005, revisited Jan. 28 2009). 7 pages.
Wikipedia, "Synchrotron" http//en.wikipedia.orci/wiki/Synchrotron (originally visited Oct. 6, 2005. revisited Jan. 28. 2009). 7 pages.
Worldwide Patent Assignee Search, Jan. 24, 2005, 224 pages.
Worldwide Patent Keyword Search, Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
Wu, Xiao Yu, "Conceptual Design and Orbit Dynamics in a 250 MeV Superconducting Synchrocyclotron", Michigan State University, 1990 (170 pages).
York et al., "Present Status and Future Possibilities at NSCL-MSU," EPAC 94, Fourth European Particle Accelerator Conference, pp. 554-556, Jun. 1994.
York et al., "The NSCL Coupled Cyclotron Project—Overview and Status," *Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," Cyclotrons and their applications 2001, 16th International Conference. American Institute of Physics Conference Proceedings, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
Communication under Rule 71(3) EPC for EP13779442.6, 96 pages (dated Jul. 24, 2017).
Notice of Allowance for CN201380062116.1, 5 pages (dated Aug. 4, 2017).
First Office Action for JP2016-174372 (English Translation), 8 pages (dated Oct. 2, 2017).
First Office Action for JP2016-174372 (Japanese Translation), 8 pages (dated Oct. 2, 2017).
Communication pursuant to Article 94(3) EPC for EP18150010.9, 3 pages (dated Jun. 22, 2018).
European Search Report for EP18150010.9, 80 pages (dated Jun. 4, 2018).
International Search Report for PCT/US2018/023694 (Coil Positioning System, filed Mar. 22, 2018), issued by ISA/EP, 5 pages (dated Jul. 16, 2018).
Written Opinion for PCT/US2018/023694 (Coil Positioning System, filed Mar. 22, 2018), issued by ISA/EP, 11 pages (dated Jul. 16, 2018).

\* cited by examiner

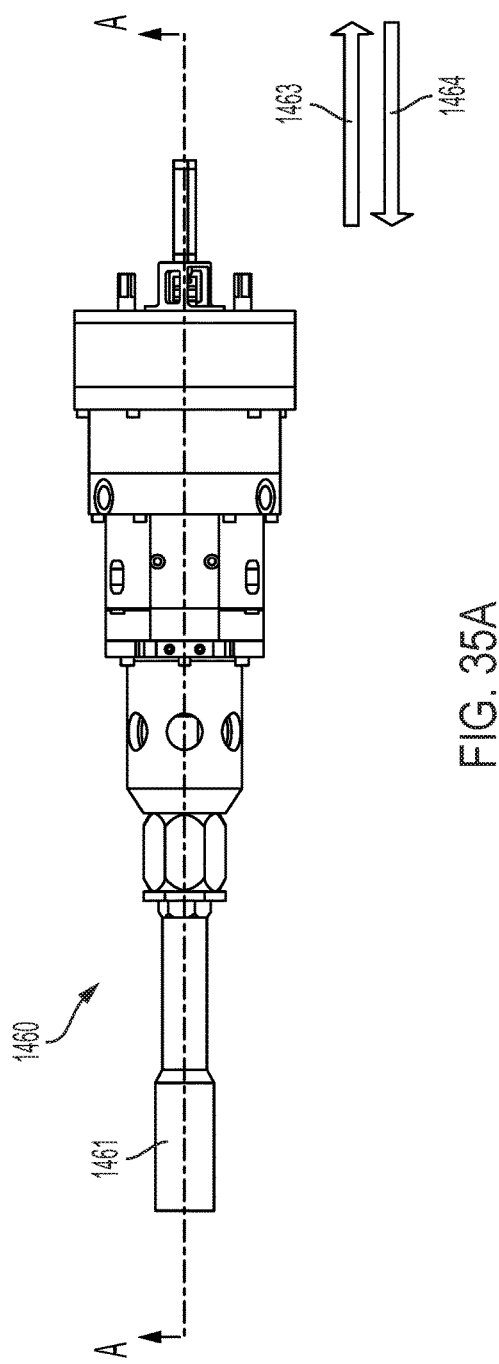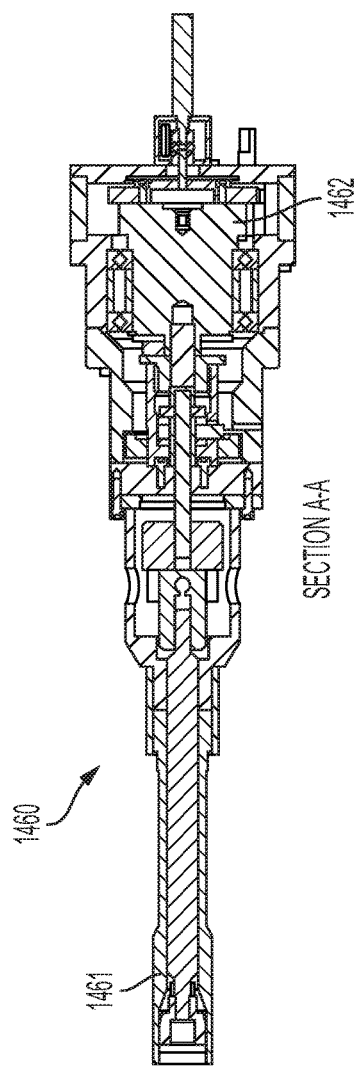
FIG. 35A
FIG. 35B
SECTION A-A
FIG. 35

COIL POSITIONING SYSTEM

CROSS-REFERENCE TO RELATED APPLICATIONS

This application is a continuation-in part of U.S. patent application Ser. No. 15/074,975 which was filed on Mar. 18, 2016, which is a continuation of U.S. patent application Ser. No. 14/039,342 which was filed on Sep. 27, 2013 (now, U.S. Pat. No. 9,301,384). The contents of U.S. patent application Ser. Nos. 15/074,975 and 14/039,342 are hereby incorporated by reference into this application. This application also claims priority to U.S. Provisional Application No. 61/707,515 which was filed on Sep. 28, 2012. The contents of U.S. Provisional Application No. 61/707,515 are hereby incorporated by reference into this application.

TECHNICAL FIELD

This application relates generally to systems for physically moving coils of a magnet in order to adjust its magnetic field distribution.

BACKGROUND

Movement of a magnet can impact its operation. Rotation, in particular, can cause coils of the magnet to move in unwanted or unexpected ways. In some cases, even very small movements—e.g., on the sub-millimeter level—can affect the magnitude and/or the shape of a magnetic field produced by the magnet. For applications, such as radiation therapy, that require accurate and predictable magnetic fields, changes in the magnetic field produced by unwanted or unexpected coil movement can be consequential.

SUMMARY

An example system comprises a magnet comprising one or more coils to conduct current to generate a magnetic field. The magnetic field is for affecting output of radiation to a target. The system also comprises one or more actuators. An actuator among the one or more actuators is at least part of a physical coupling to the one or more coils. The actuator is controllable to move the one or more coils via the physical coupling based on movement of the magnet. The example system may include one or more of the following features, either alone or in combination.

A housing may at least partly enclose the magnet. Movement of the magnet causes the one or more coils to move relative to the housing in a first direction. The one or more actuators is controllable to move the one or more coils relative to the housing in a second direction that is substantially opposite to the first direction in response to movement of the one or more coils in the first direction.

A housing may border the magnet. Movement of the magnet causes the one or more coils to move relative to the housing. The one or more actuators are controllable to move the one or more coils relative to the housing to compensate, at least partly, for movement of the one or more coils relative to the housing caused by movement of the magnet.

A housing may hold the magnet. The magnet is movable from a first orientation to a second orientation, with the movement of the magnet causing the one or more coils to move from a first position relative to the housing at the first orientation to a second position relative to the housing at the second orientation. The one or more actuators are controllable to move the one or more coils so that the one or more coils are at the first position relative to the housing when the housing is at the second orientation.

The magnet may comprise a support structure to hold the one or more coils. The physical coupling may comprise the support structure, and the actuator may be configured to move the one or more coils by moving the support structure. A vacuum enclosure may be around the magnet. The physical coupling may comprise a strap connected between the actuator and the support structure. The actuator may be connected to the vacuum enclosure and to the strap. The actuator may be configured to increase tension on the strap to move the one or more coils. The actuator may comprise a differential screw that connects to the strap, and a motor connected to drive the differential screw to increase tension on the strap. The magnet may be a superconducting magnet. The system may comprise a cryostat to maintain the one or more coils at temperatures that enable superconductivity in the one or more coils. The cryostat may include the support structure.

The one or more actuators may comprise a group of actuators. Each actuator in the group may be at least part of a separate physical coupling to the one or more coils. Each actuator in the group may be controllable to move the one or more coils via a respective physical coupling based on movement of the magnet. An enclosure may house the magnet. The group of actuators are may be inside an external perimeter of the enclosure. Each actuator may be configured to pull the one or more coils at least partly inwards towards an interior of the external perimeter. Each actuator in the group of actuators may be configured to pull the one or more coils at least partly outwards relative to an external perimeter of the enclosure. The group of actuators may be mounted in a symmetric arrangement on the enclosure and are controllable to act in concert.

An enclosure may at least partly surround the magnet. The system may also comprise one or more sensors to detect movement of the one or more coils relative to the enclosure. The actuator may be controllable based on detection of the movement of the one or more coils relative to the enclosure. The one or more sensors may comprise one or more magnetic field sensors mounted to the enclosure. The one or more magnetic field sensors may be configured to detect a change in the magnetic field generated by the one or more coils relative to the one or more magnetic field sensors. The detected change in the magnetic field may be indicative of the movement of the one or more coils relative to the enclosure. The one or more sensors may comprise one or more displacement sensors mounted to the enclosure to obtain measurements based on positions of the one or more coils. The system may comprise one or more processing devices to determine the movement of the one or more coils based on the measurements.

The system may comprise a particle accelerator. The magnet may be part of the particle accelerator. The particle accelerator may be configured for movement that is at least partly rotational, translational, and/or pivotal. The magnet may be configured for movement as a result of the magnet being part of the particle accelerator. The particle accelerator may be a synchrocyclotron, the magnet may be a superconducting magnet, and the system may comprise a gantry on which the particle accelerator is mounted to produce the movement of the particle accelerator and of the magnet.

The radiation may comprise a particle beam, and current in the one or more coils is controllable to affect the particle beam prior to application to an irradiation target. The current may be controllable to direct the particle beam to one or more points in the irradiation target. The current may be controllable to focus the particle beam prior to output to the irradiation target.

An example particle therapy system comprises a magnet comprising one or more coils to conduct current to generate a magnetic field, with the magnetic field to affect output of a particle beam; a housing to hold the magnet; a mount to which the housing is connected to enable movement of the housing, with the movement causing a displacement of the one or more coils relative to the housing; and one or more actuators that are part of a physical coupling to the one or more coils, with the one or more actuators being controllable to move, via the physical coupling, the one or more coils relative to the housing to at least partly correct the displacement. The example particle therapy system may include one or more of the following features, either alone or in combination.

Two or more of the actuators may be controllable to act in concert to move the one or more coils. The displacement may occur along a first direction, and the one or more actuators may be controllable to move the one or more coils in a second direction that is substantially opposite to the first direction. The one or more actuators may be controllable to move the one or more coils in real-time during movement of the housing. The one or more actuators may be controllable to move the one or more coils following the movement of the housing that caused the displacement.

The magnet may comprise a support structure to hold the one or more coils. The physical coupling may comprise the support structure. The one or more actuators may be configured to move the coil by moving the support structure physically. For an actuator among the one or more actuators, a physical coupling comprises a strap connected between the actuator and the support structure, and the actuator is connected to the housing and to the strap. The actuator may be configured to increase tension on the strap to move the one or more coils.

The actuator may comprise a differential screw that connects to the strap, and the actuator mat comprise, or be associated with, a motor connected to drive the differential screw to increase tension on the strap.

The magnet may be a superconducting magnet. The system may comprises a cryostat to maintain the one or more coils at temperatures that enable superconductivity in the one or more coils. The cryostat may include the support structure (e.g., a reverse bobbing). The one or more actuators may comprise a group of actuators, with each actuator in the group being at least part of a separate physical coupling to the one or more coils, and with each actuator in the group being controllable to move the one or more coils via a respective physical coupling.

The group of actuators may be mounted inside of an exterior perimeter of the housing, with each actuator being configured to pull the one or more coils at least partly inwards towards an interior of the exterior perimeter. Each actuator in the group of actuators may be configured to pull the one or more coils at least partly outwards relative to an exterior perimeter of the housing. The group of actuators may be mounted in a symmetric arrangement on the housing and are controllable to act in concert.

The example system may comprise one or more sensors to detect movement of the one or more coils relative to the housing. The one or more actuators may be controllable based on detection of the movement of the one or more coils relative to the housing. The one or more sensors may comprise one or more magnetic field sensors mounted to the housing, with the one or more magnetic field sensors being configured to detect a change in the magnetic field generated by the one or more coils relative to the one or more magnetic field sensors, and with the detected change in the magnetic field being indicative of the movement of the one or more coils relative to the housing. The one or more sensors may comprise one or more displacement sensors mounted to the housing to obtain measurements based on the positions of the one or more coils. The system may comprise one or more processing devices to determine the movement of the one or more coils based on the measurements.

The example system may comprise a particle accelerator. The magnet and the housing may be part of the particle accelerator. The particle accelerator may be configured for movement that is at least partly rotational. The magnet and the housing may be configured for movement as a result of the magnet and the housing being part of the particle accelerator. The particle accelerator may be a synchrocyclotron. The magnet may be a superconducting magnet. The mount may comprise a rotatable gantry on which the particle accelerator is mounted. The current in the one or more coils may be controllable to affect the particle beam prior to application to an irradiation target. The current may be controllable to direct the particle beam to one or more points in the irradiation target. The current may be controllable to focus the particle beam prior to output to the irradiation target.

An example system comprises means for rotating a magnet. The magnet may comprise one or more coils to conduct current to generate a magnetic field. Movement of the magnet may cause displacement of the one or more coils away from a predefined position. The example system may comprise means for physically moving the one or more coils so that, following movement of the magnet, the one or more coils are in the predefined position.

An example system comprises a magnet comprising one or more coils to conduct current to generate a magnetic field; and one or more actuators, with an actuator among the one or more actuators being at least part of a physical coupling to the one or more coils. The actuator is controllable to move the one or more coils via the physical coupling to arrive at a target distribution of the magnetic field. The example system may include one or more of the following features, either alone or in combination.

The system may comprise one or more sensors to detect movement of the one or more coils relative to a reference. The actuator may be controllable based on detection of the movement of the one or more coils relative to the enclosure. The one or more sensors may comprise one or more magnetic field sensors. The one or more magnetic field sensors may be configured to detect a change in the magnetic field generated by the one or more coils relative to the one or more magnetic field sensors. The detected change in the magnetic field may be indicative of the movement of the one or more coils. The one or more sensors may comprise one or more displacement sensors to obtain measurements based on positions of the one or more coils. The system may comprise one or more processing devices to determine the movement of the one or more coils based on the measurements.

The system may comprise a particle accelerator. The magnet may be part of the particle accelerator. The particle accelerator may be configured for movement. The magnet may be configured for movement as a result of the magnet being part of the particle accelerator. The particle accelerator may be a synchrocyclotron. The magnet is a superconducting magnet, and the system may comprise a gantry on which the particle accelerator is mounted to produce the movement of the particle accelerator and of the magnet.

The magnet may be configured to accelerate particles in a cavity of the particle accelerator to produce a particle beam. The magnet may be configured to focus particles during extraction of a particle beam from the particle accelerator. The magnet may be configured to control movement of a particle beam output from the particle accelerator relative to a target of the particle beam.

An example particle accelerator includes a coil to provide a magnetic field to a cavity; a particle source to provide a plasma column to the cavity; a voltage source to provide a radio frequency (RF) voltage to the cavity to accelerate particles from the plasma column, where the magnetic field causes particles accelerated from the plasma column to move orbitally within the cavity; an enclosure containing an extraction channel to receive the particles accelerated from the plasma column and to output the received particles from the cavity; and a structure arranged proximate to the extraction channel to change an energy level of the received particles. This example particle accelerator may include one or more of the following features, either alone or in combination.

The structure may have multiple thicknesses. The structure may have variable thickness ranging from a maximum thickness to a minimum thickness. The structure may be movable relative to the extraction channel to place one of the multiple thicknesses in a path of the received particles. The structure may be wheel-shaped and may be rotatable within the extraction channel. The structure may include at least one of the following materials: beryllium, carbon and plastic.

The particle accelerator may be rotatable relative to a fixed position. The particle accelerator may include a control system to control movement of the structure based on a rotational position of the particle accelerator.

The particle accelerator may include a regenerator to adjust the magnetic field within the cavity to thereby change successive orbits of the particles accelerated from the plasma column so that, eventually, the particles output to the extraction channel.

An example proton therapy system may include the foregoing particle accelerator, where the particles comprise protons; and a gantry on which the particle accelerator is mounted. The gantry may be rotatable relative to a patient position. Protons may be output essentially directly from the particle accelerator to the patient position.

An example particle accelerator includes a coil to provide a magnetic field to a cavity; a particle source to provide a plasma column to the cavity; a voltage source to provide a radio frequency (RF) voltage to the cavity to accelerate particles from the plasma column, where the magnetic field causes particles accelerated from the plasma column to move orbitally within the cavity; an enclosure containing an extraction channel to receive the particles accelerated from the plasma column and to output the received particles from the cavity; and a regenerator to adjust the magnetic field within the cavity to thereby change successive orbits of the particles accelerated from the plasma column so that, eventually, the particles output to the extraction channel. The regenerator is movable within the cavity relative to orbits of the particles. This example particle accelerator may include one or more of the following features, either alone or in combination.

The regenerator may be configured to move radially relative to an approximate center of the cavity. An actuator may be configured to move the regenerator in response to a control signal. The particle accelerator may be rotatable relative to a fixed position. The particle accelerator may include a control system to generate the control signal to control movement of the regenerator based on a rotational position of the particle accelerator. The regenerator may include a ferromagnetic material, such as iron.

An example proton therapy system may include the foregoing particle accelerator, where the particles comprise protons; and a gantry on which the particle accelerator is mounted. The gantry may be rotatable relative to a patient position. Protons may be output essentially directly from the particle accelerator to the patient position.

An example particle accelerator includes a coil to provide a magnetic field to a cavity; a particle source to provide a plasma column to the cavity; a voltage source to provide a radio frequency (RF) voltage to the cavity to accelerate particles from the plasma column, where the magnetic field causes particles accelerated from the plasma column to move orbitally within the cavity; an enclosure containing an extraction channel to receive the particles accelerated from the plasma column and to output the received particles from the cavity; and a regenerator to adjust the magnetic field within the cavity to thereby change successive orbits of the particles accelerated from the plasma column so that, eventually, the particles output to the extraction channel. The enclosure includes magnetic structures, where at least one of the magnetic structures has a slot therein, where the slot contains a magnetic shim that is ferromagnetic and movable within the slot, where the magnetic shim is movable relative to the regenerator to affect an amount by which the regenerator adjusts the magnetic field. This example particle accelerator may include one or more of the following features, either alone or in combination.

The at least one magnetic structure may have multiple slots therein. Each slot may contain a magnetic shim that is ferromagnetic and that is movable within the slot. Each magnetic shim may be movable relative to the regenerator to affect an amount by which the regenerator adjusts the magnetic field.

The particle accelerator may be rotatable relative to a fixed position. The particle accelerator may include a control system to generate a control signal to control movement of the magnetic shim (or multiple magnetic shims) based on a rotational position of the particle accelerator. The magnetic shim (or multiple magnetic shims) may be or include an electromagnet.

An example proton therapy system may include the foregoing particle accelerator, where the particles comprise protons; and a gantry on which the particle accelerator is mounted. The gantry may be rotatable relative to a patient position. Protons may be output essentially directly from the particle accelerator to the patient position.

An example particle accelerator may include a cryostat comprising a superconducting coil, where the superconducting coil conducts a current that generates a magnetic field; magnetic structures adjacent to the cryostat, where the cryostat is attached to the magnetic structures and the magnetic structures contain a cavity; a particle source to provide a plasma column to the cavity; a voltage source to provide a radio frequency (RF) voltage to the cavity to accelerate particles from the plasma column, where the magnetic field cause particles accelerated from the plasma column to move orbitally within the cavity; an extraction channel to receive the particles accelerated from the plasma column and to output the received particles from the cavity; and an actuator that is controllable to move the cryostat relative to the magnetic structures. This example particle accelerator may include one or more of the following features, either alone or in combination.

The particle accelerator may be rotatable relative to a fixed position. The particle accelerator may include a control system to generate a control signal to control the actuator based on a rotational position of the particle accelerator. The actuator may be controlled to control movement of the cryostat so as to compensate for effects of gravity on the superconducting coil.

An example proton therapy system may include the foregoing particle accelerator, where the particles comprise protons; and a gantry on which the particle accelerator is mounted. The gantry may be rotatable relative to a patient position. Protons may be output essentially directly from the particle accelerator to the patient position.

An example variable-energy particle accelerator includes: magnetic structures defining a cavity in which particles are accelerated for output as a particle beam that has a selected energy from among a range of energies; an extraction channel to receive the particle beam; and a structure proximate to the extraction channel to intercept the particle beam prior to the particle beam entering the extraction channel, where the structure is movable based on the selected energy, and where the structure is for absorbing at least some energy of the particle beam prior to the particle beam entering the extraction channel. The example variable-energy particle accelerator may include one or more of the following features, either alone or in combination.

The structure may be a wheel having varying thickness, where different thicknesses are capable of absorbing different amounts of energy. The variable-energy particle accelerator may include a magnetic regenerator to implement a magnetic field bump at a particle orbit that corresponds to the selected energy. The magnetic regenerator may be movable based on movement of the variable-energy particle accelerator. The magnetic regenerator may be movable to intercept a particle orbit having the selected energy.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

FIG. 35, comprised of FIGS. 35A and 35B, includes engineering diagrams showing, respectively, a side view of the example coil positioning actuator of FIG. 34 and a cut-away, side view of the example coil positioning actuator of FIG. 34.

Like reference symbols in the various drawings indicate like elements.

DETAILED DESCRIPTION

Figure 1:
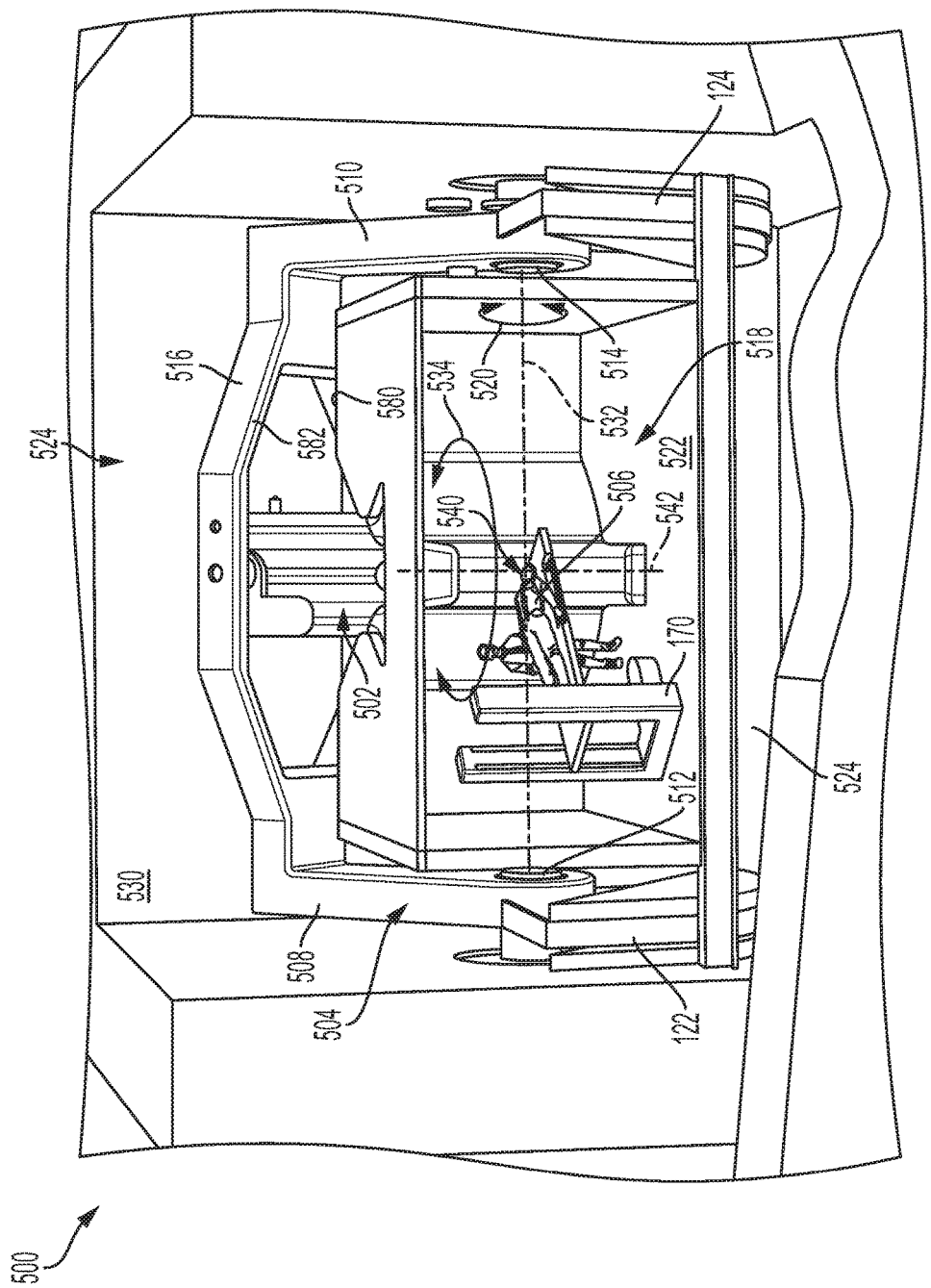
FIG. 1 is a perspective view of an example therapy system.
Figure 2:
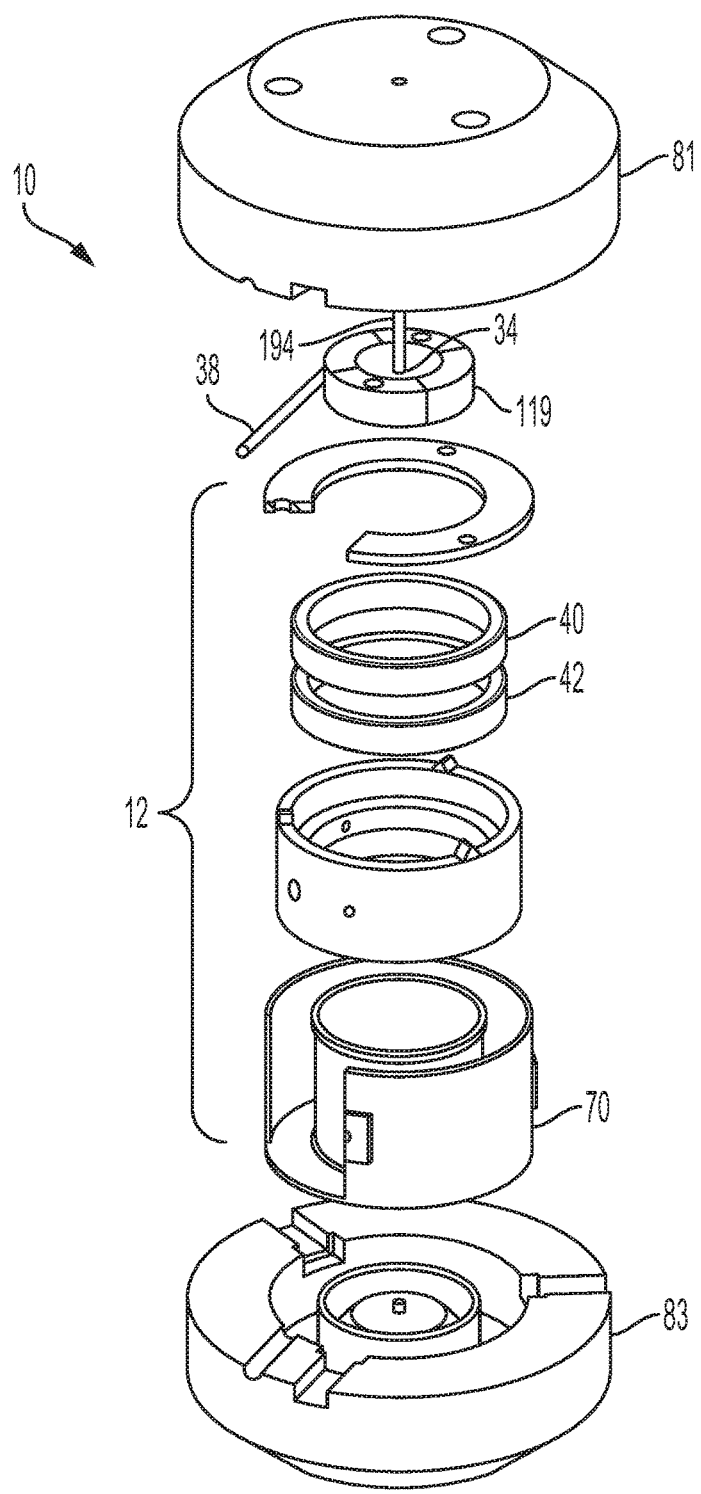
FIG. 2 is an exploded perspective view of components of an example synchrocyclotron.

Described herein is an example of a particle accelerator for use in a system, such as a proton or ion therapy system. The system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached stably at both ends to the rotating legs of the gantry. As a result of rotation of the gantry around the patient, the particle accelerator also rotates.

In an example implementation, the particle accelerator (e.g., the synchrocyclotron) includes a cryostat that holds a superconducting coil for conducting a current that generates a magnetic field (B). In this example, the cryostat uses liquid helium (He) to maintain the coil at superconducting temperatures, e.g., 4° Kelvin (K). Magnetic yokes are adjacent (e.g., around) the cryostat, and define a cavity in which particles are accelerated. The cryostat is attached to the magnetic yokes through straps or the like. While this attachment, and the attachment of the superconducting coil inside the cryostat, restricts movement of the superconducting coil, coil movement is not entirely prevented. For example, in some implementations, as a result of gravitational pull during rotation of the gantry, the superconducting coil is movable by small amounts (e.g., tenths of millimeters in some cases). As described below, this movement can affect the amount of energy in a particle beam that is received at an extraction channel and thereby affect the output of the particle accelerator.

In this example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate particles from the plasma column. As noted, in this example, the particle accelerator is a synchrocyclotron. Accordingly, the RF voltage is swept across a range of frequencies to account for relativistic effects on the particles (e.g., increasing particle mass) when extracting particles from the column. The magnetic field produced by the coil causes particles accelerated from the plasma column to accelerate orbitally within the cavity. A magnetic field regenerator is positioned in the cavity to adjust the existing magnetic field inside the cavity to thereby change locations of successive orbits of the particles accelerated from the plasma column so that, eventually, the particles output to an extraction channel that passes through the yokes. The regenerator may increase the magnetic field at a point in the cavity (e.g., it may produce a magnetic field "bump" at an area of the cavity), thereby causing each successive orbit of particles at that point to precess outward toward the entry point of the extraction channel, eventually reaching the extraction channel. The extraction channel receives particles accelerated from the plasma column and outputs the received particles from the cavity.

Movement of the superconducting coil can affect the locations of the orbits inside the cavity. For example, movement in one direction can cause lower-energy orbits to impact the regenerator, while movement in another direction can cause higher-energy orbits to impact the regenerator (particle orbit energy is proportional to the radial distance from the originating plasma column). So, in a case where overly low-energy orbits impact the regenerator, the particle beam may collide with the inner edge of the extraction channel, as noted above. In a case where overly high-energy orbits impact the regenerator, the particle beam may collide with the outer edge of the extraction channel, as noted above. The example systems described herein use techniques to compensate for these effects resulting from motion of the superconducting coil due to its rotation (e.g., due to the effect of gravity). A summary of these techniques is provided below, followed by a description of an example particle therapy system in which they may be implemented and more detailed descriptions of these various techniques.

In an example technique, a structure is incorporated proximate to (e.g., at the entry to or inside of) the extraction channel. The structure may be a rotatable variable-thickness wedge having a wheel-like shape. The structure absorbs energy of the particle beam, thereby allowing a lower-energy (e.g., appropriately energized) beam to pass through the extraction channel. The thicker portions of the structure absorb more energy than the thinner portions of the structure. In some implementations, the structure may contain no material at a point where the particle beam is meant to pass without any energy absorption. Alternatively, the structure may be movable out of the beam path. The structure thus enables the amount of energy in the beam to be variably adjusted. In some implementations, the structure is controlled based on a rotational position of the particle accelerator. For example, the position of the gantry may be determined, and that position may be used to control the rotational position of the energy-absorbing structure. Ideally, the structure minimizes scattering of the beam; however, in practice, there may be amounts of scatter that are present and that are tolerable.

In another example technique, the physical position of the regenerator within the cavity may be adjustable to compensate for movement of the superconducting coil. For example, computer-controlled actuators may be used to adjust the position of the regenerator within the cavity based, e.g., on a rotational position of the particle accelerator. By so adjusting the position of the regenerator, it may be possible to position the regenerator so that the appropriate adjustment to the magnetic field resulting from the regenerator impacts the proper particle orbits regardless of the rotational position of the particle accelerator.

The regenerator is typically made of a ferromagnetic material. It is therefore possible to adjust the magnetic strength of the regenerator using one or more magnetic shims. Accordingly, in another example technique, it is possible to adjust the magnetic field of the regenerator (e.g., to increase or decrease the magnetic field bump produced by the regenerator) or to move the effective location of the magnetic field perturbation produced by the regenerator without physically moving the regenerator. For example, if movement of the superconducting coil results in lower-energy orbits impacting the regenerator, the magnetic field of the regenerator can be decreased so that it doesn't begin to perturb beam orbits until higher energy orbits reach it. It could also be effectively moved radially outward while maintaining the same overall strength (peak field) so that the orbits gain higher energy before being effected by the regenerator. Likewise if the superconducting coil movement results in higher energy orbits impacting the regenerator the strength of the regenerator can be increased or positioned radially inward to interact with orbits at lower energies. In an example implementation, the magnetic field is adjusted by moving a magnetic shim (e.g., a metal plunger) within a slot/hole in a magnetic yoke that is near to the regenerator. The magnetic shim is made of ferromagnetic material and its proximity to the regenerator affects the magnetic field of the regenerator. Moving the magnetic shim closer to the regenerator (e.g., further inside the slot increases the magnetic field produced by the regenerator; and moving the magnetic shim away from the regenerator (e.g., upwards in, or outside of, the slot) decreases the magnetic field produced by the regenerator. In another example the magnetic shim can be placed radially closer to the center of the cyclotron than the regenerator magnetic center. When the shim is place closer to the acceleration plane, it moves the effective center of the regenerator magnetic perturbation without appreciably changing the peak magnetic field strength. The magnetic shim may be computer-controlled to vary its position based, e.g., on a rotational position of the particle accelerator.

In some implementations, more than one magnetic shim may be used. In still other implementations, miniature electromagnet(s) may be used as a magnetic shim, and the current therethrough controlled based, e.g., on a rotational position of the particle accelerator.

In another example, the entire cryostat may be moved relative to the yokes to compensate for movement of the superconducting coil. For example, movement of the cryostat can affect which orbits of particles impact the regenerator. So, if movement of the superconducting coil occurs in one direction, the cryostat may be moved in the direction to compensate for that movement and cause the superconducting coil to be properly repositioned.

The foregoing techniques for adjusting the energy of a particle beam in a particle accelerator may be used individually in a single particle accelerator, or any two or more of those techniques may be used in any appropriate combination in a single particle accelerator. An example of a particle therapy system in which the foregoing techniques may be used is provided below.

Referring to FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls, which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 4 to 20 Tesla or 6 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (e.g., 502 in FIG. 1) includes a magnet system 12 that contains an particle source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
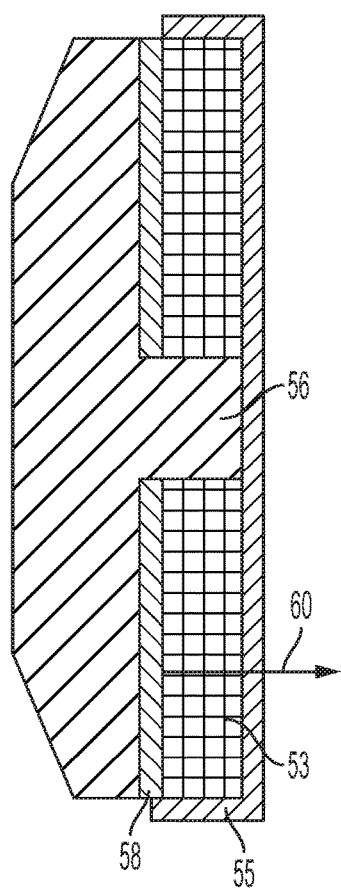
FIG. 7 is a cross-sectional view of a portion of an example reverse bobbin and windings.
Figure 8:
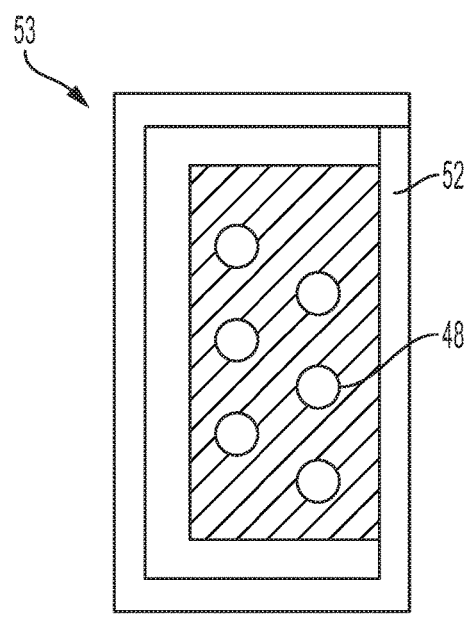
FIG. 8 is a cross sectional view of an example cable-in-channel composite conductor.

The two superconducting magnet coils are centered on a common axis 47 and are spaced apart along the axis. As shown in FIGS. 7 and 8, the coils are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation 52 (in this example, a woven fiberglass material). The copper channel containing the wires 53 is then wound in a coil having a rectangular cross-section of 8.55 cm×19.02 cm, having 26 layers and 49 turns per layer. The wound coil is then vacuum impregnated with an epoxy compound. The finished coils are mounted on an annular stainless steel reverse bobbin 56. Heater blankets 55 are placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 5:
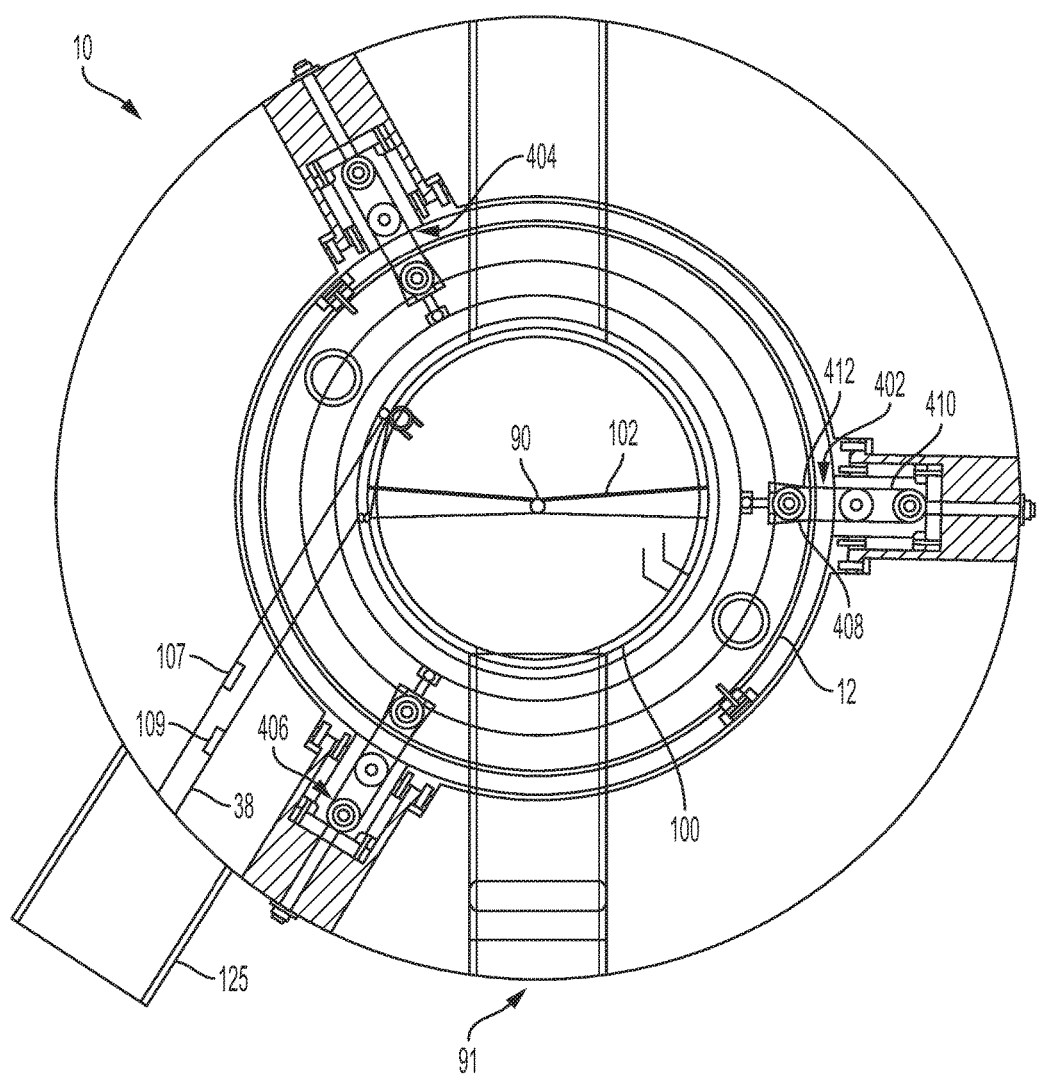
Figure 6:
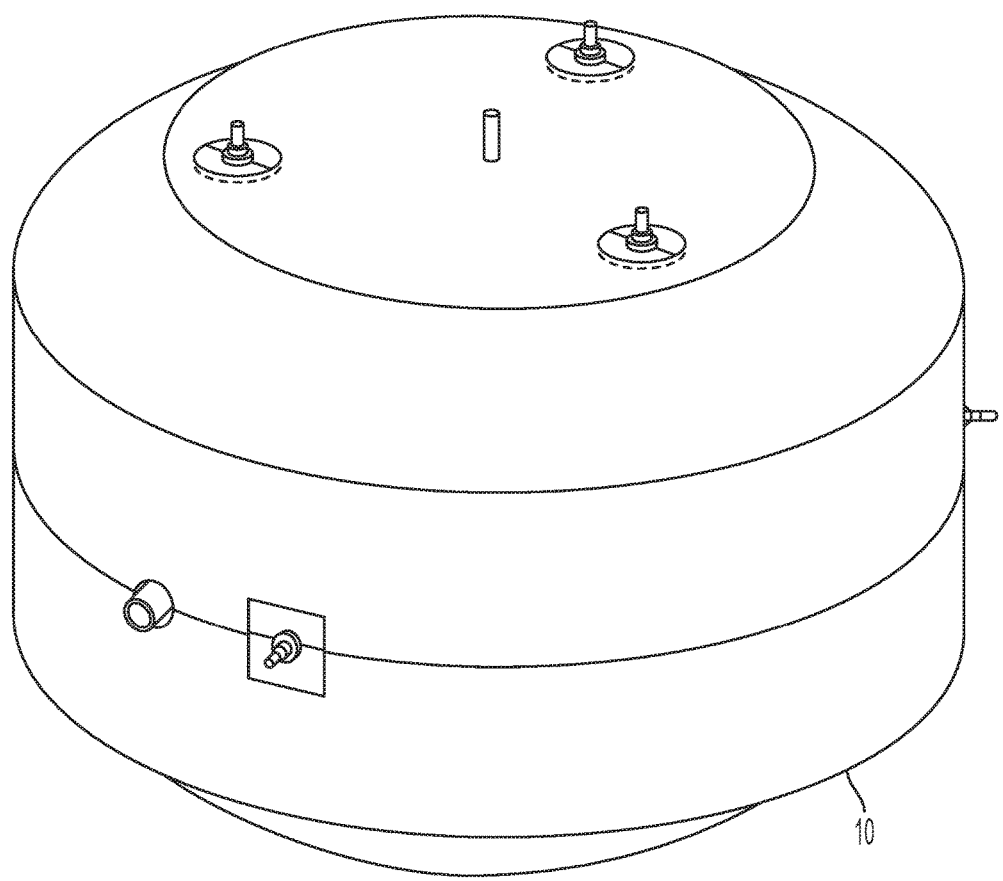
FIG. 6 is a perspective view of an example synchrocyclotron.

The geometry of the coil is maintained by mounting the coils in a reverse rectangular bobbin 56 to exert a restorative force 60 that works against the distorting force produced when the coils are energized. As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes one S2 fiberglass link and one carbon fiber link. In some implementations, the carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

Figure 3:
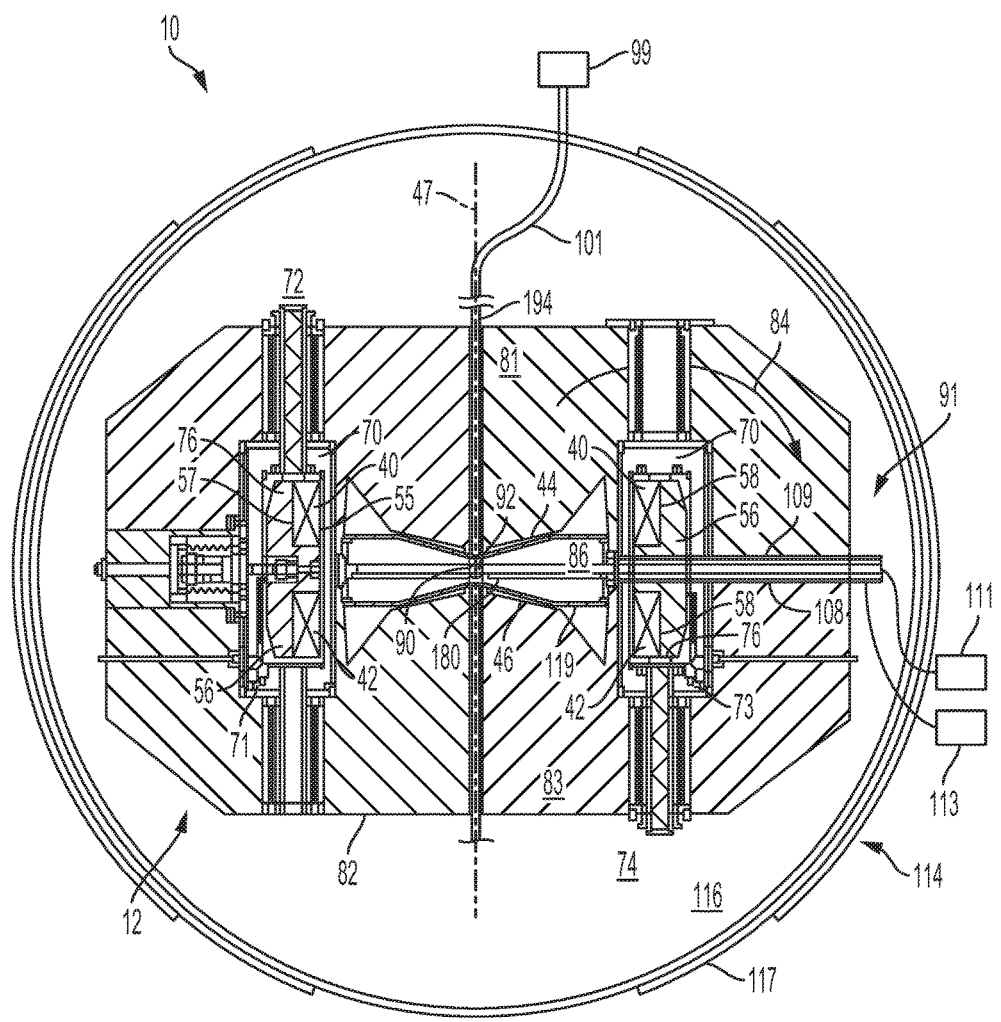
FIGS. 3, 4, and 5 are cross-sectional views of example synchrocyclotron structures.

Referring to FIG. 3, the field strength profile as a function of radius is determined largely by choice of coil geometry and pole face shape; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator. In some implementations, the synchrocyclotron may have an active return system to reduce stray magnetic fields. An example of an active return system is described in U.S. Pat. No. 8,791,656, entitled "Active Return System", the contents of which are incorporated herein by reference. In the active return system, the relatively large magnetic yokes described herein are replaced by smaller magnetic structures, referred to as pole pieces. Superconducting coils run current opposite to the main coils described herein in order to provide magnetic return and thereby reduce stray magnetic fields.

Figure 9:
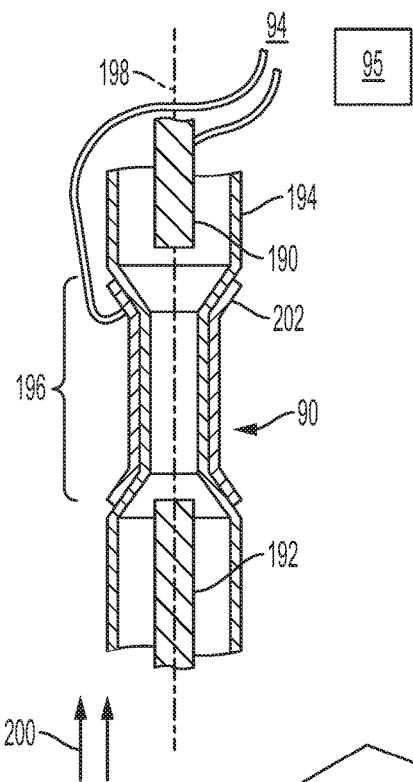
FIG. 9 is a cross-sectional view of an example ion source.

As shown in FIGS. 3 and 9, the synchrocyclotron includes a particle source 90 of a Penning ion gauge geometry located near the geometric center 92 of the magnet structure 82. The particle source may be as described below, or the particle source may be of the type described in U.S. Pat. No. 8,581,523, entitled "Interrupted Particle Source", the contents of which are incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In some implementations, the gas in gas tube 101 may include a mixture of hydrogen and one or more other gases. For example, the mixture may contain hydrogen and one or more of the noble gases, e.g., helium, neon, argon, krypton, xenon and/or radon (although the mixture is not limited to use with the noble gases). In some implementations, the mixture may be a mixture of hydrogen and helium. For example, the mixture may contain about 75% or more of hydrogen and about 25% or less of helium (with possible trace gases included). In another example, the mixture may contain about 90% or more of hydrogen and about 10% or less of helium (with possible trace gases included). In examples, the hydrogen/helium mixture may be any of the following: >95%/<5%, >90%/<10%, >85%/<15%, >80%/<20%, >75%/<20%, and so forth.

Possible advantages of using a noble (or other) gas in combination with hydrogen in the particle source may include: increased beam intensity, increased cathode longevity, and increased consistency of beam output.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. Pat. No. 8,581,523), all (or a substantial part) of the tube containing plasma is removed at the acceleration region, thereby allowing ions to be more rapidly accelerated in a relatively high magnetic field.

Figure 10:
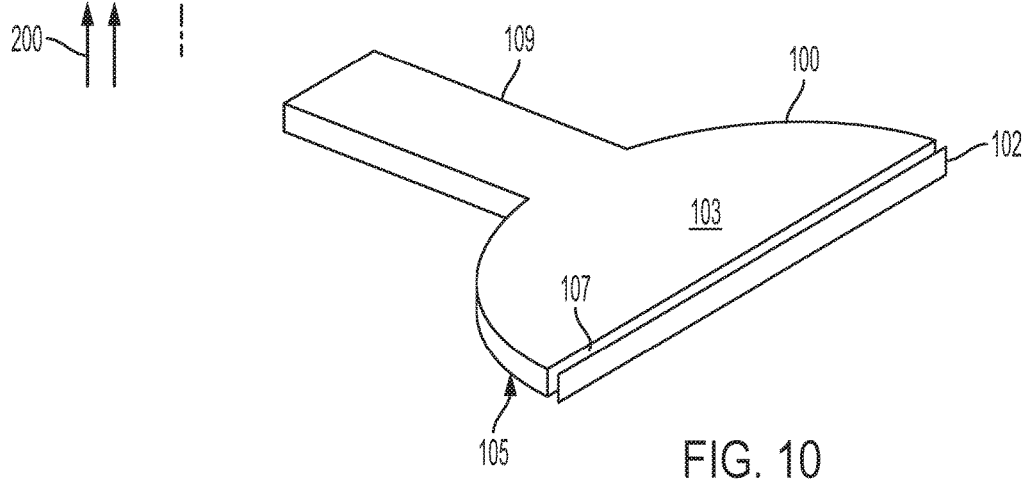
FIG. 10 is a perspective view of an example dee plate and an example dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. The radio frequency electric field may be controlled in the manner described in U.S. Pat. No. 8,933,650, entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, in some implementations, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

In some implementations, the vacuum chamber 119 in which the acceleration occurs is a generally cylindrical container that is thinner in the center and thicker at the rim. The vacuum chamber encloses the RF plates and the particle source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

In some implementations, the magnetic field within the pole gap needs to have certain properties to maintain the beam within the evacuated chamber as it accelerates. The magnetic field index n, which is shown below, $$n=-(r/B)dB/dr,$$

should be kept positive to maintain this "weak" focusing. Here r is the radius of the beam and B is the magnetic field. Additionally, in some implementations, the field index needs to be maintained below 0.2, because at this value the periodicity of radial oscillations and vertical oscillations of the beam coincide in a vr=2 $v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5)—e.g., a scanning system or a scattering system—that can be programmably controlled to create a desired combination of scattering angle and range modulation for the beam. Beam formation system 125 may be used in conjunction with an inner gantry 601 (FIG. 14) to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements, as described herein (see, e.g., FIGS. 42 to 45).

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more computers programmed with appropriate programs to effect control.

The control of the gantry, the patient support, the active beam shaping elements, and the synchrocyclotron to perform a therapy session is achieved by appropriate therapy control electronics (not shown).

Figure 11:
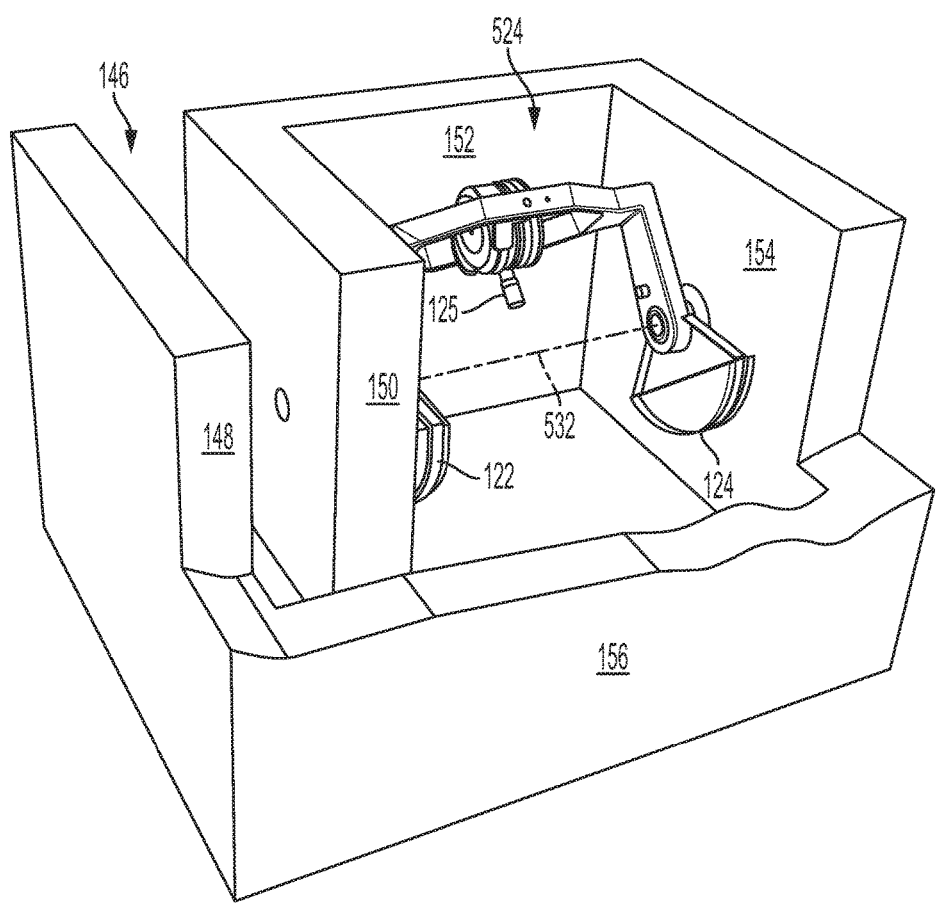
FIG. 11 is a perspective view of an example vault.
Figure 12:
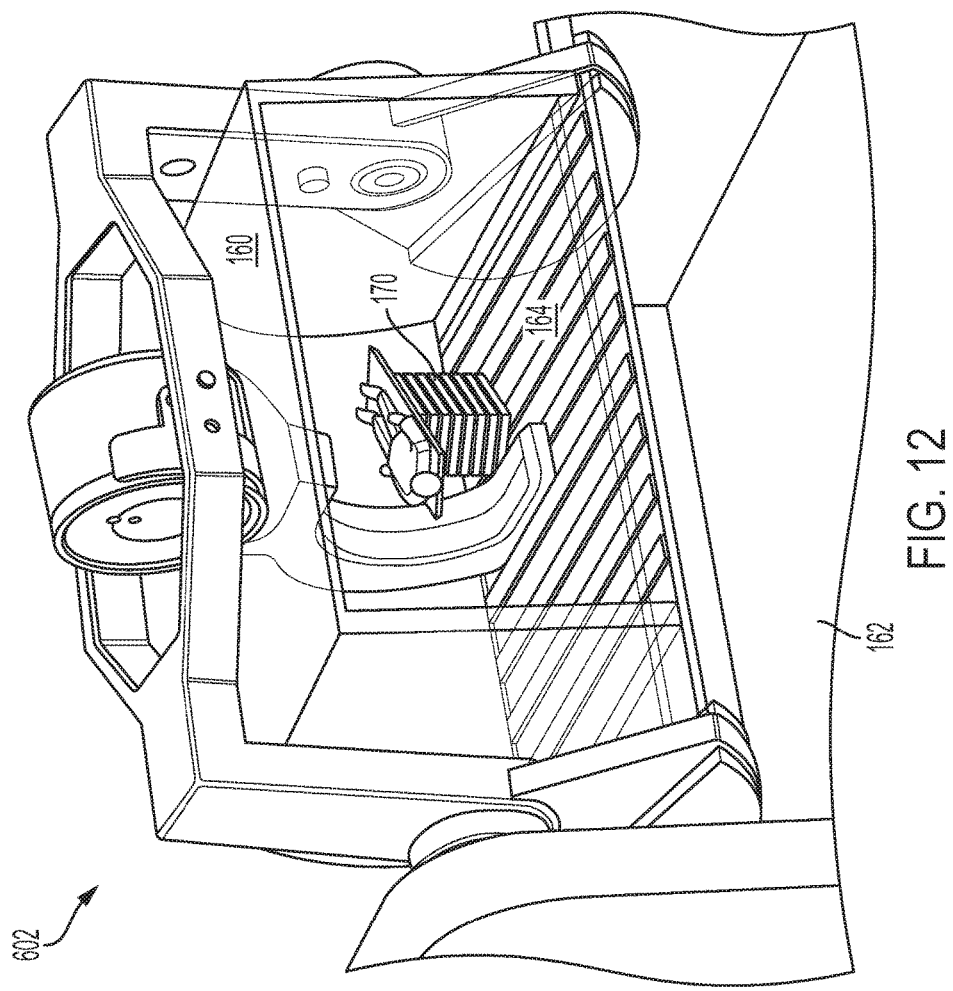
FIG. 12 is a perspective view of an example treatment room with a vault.

As shown in FIGS. 1, 11, and 12, the gantry bearings are supported by the walls of a cyclotron vault 524. The gantry enables the accelerator to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is not in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
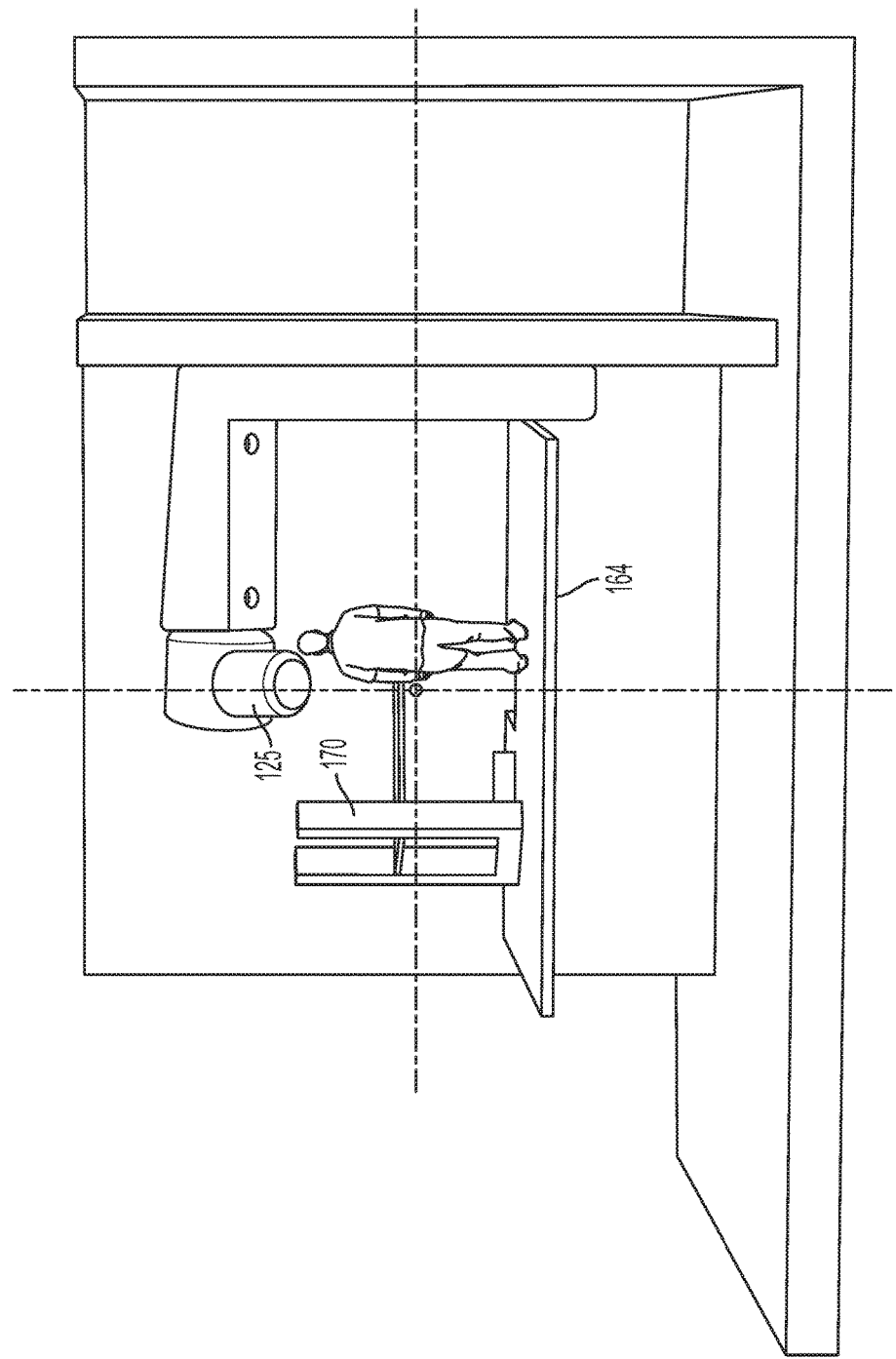
FIG. 13 shows an example of a patient relative to an accelerator.

Referring to FIGS. 11, 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

Figure 14:
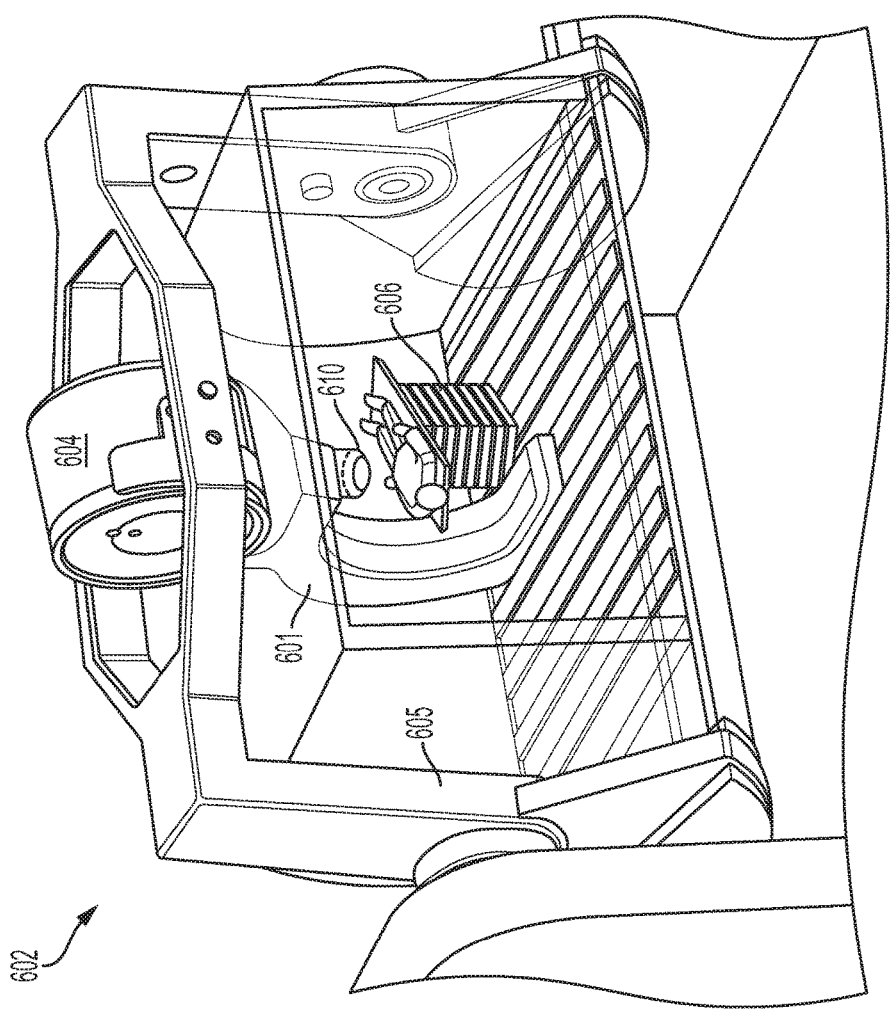
FIG. 14 shows a patient positioned within an example inner gantry in a treatment room.

In system 602 of FIG. 14, a beam-producing particle accelerator of the type described herein, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Further details regarding an example implementation of the foregoing system may be found in U.S. Pat. No. 7,728,311 entitled "Charged Particle Radiation Therapy", and in U.S. Pat. No. 8,344,340 entitled "Inner Gantry". The contents of U.S. Pat. No. 7,728,311 and of U.S. Pat. No. 8,344,340 are hereby incorporated by reference into this disclosure. In some implementations, the synchrocyclotron may be a variable-energy device, such as that described in U.S. Patent Publication No. 2014/0371511, entitled "Particle Accelerator That Produces Charged Particles Having Variable Energies", the contents of which are incorporated herein by reference.

Figure 15:
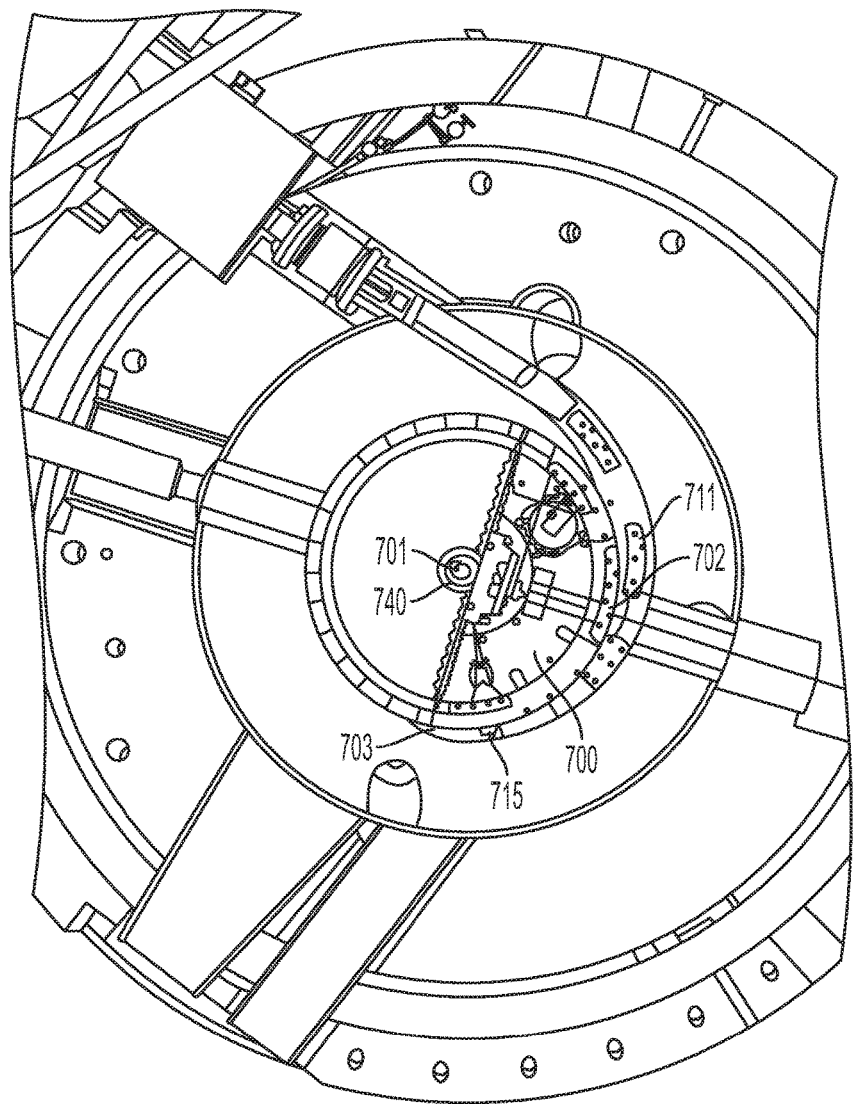
FIG. 15 is a cut-away, top view of an example acceleration cavity and extraction channel.

FIG. 15 shows a top view of a portion of a cavity 700 in which particles are accelerated orbitally (e.g., in outward spiral orbits). A particle source 701, examples of which are described above, is disposed at about the center of the cavity. Charged particles (e.g., protons or ions) are extracted from a plasma column generated by particle source 701. The charged particles accelerate outwardly in orbits 740 toward, and eventually reaching, magnetic regenerator 702. In this example implementation, regenerator 702 is a ferromagnetic structure made, e.g., of steel, iron, or any other type of ferromagnetic material. Regenerator 702 alters the background magnetic field that causes the outward orbital acceleration. In this example, regenerator 702 augments that magnetic field (e.g., it provides a bump in the field). The bump in the background magnetic field affects the particle orbits in a way that causes the orbits to move outwardly towards extraction channel 703. Eventually, the orbits enter extraction channel 703, from which they exit.

Figure 16:
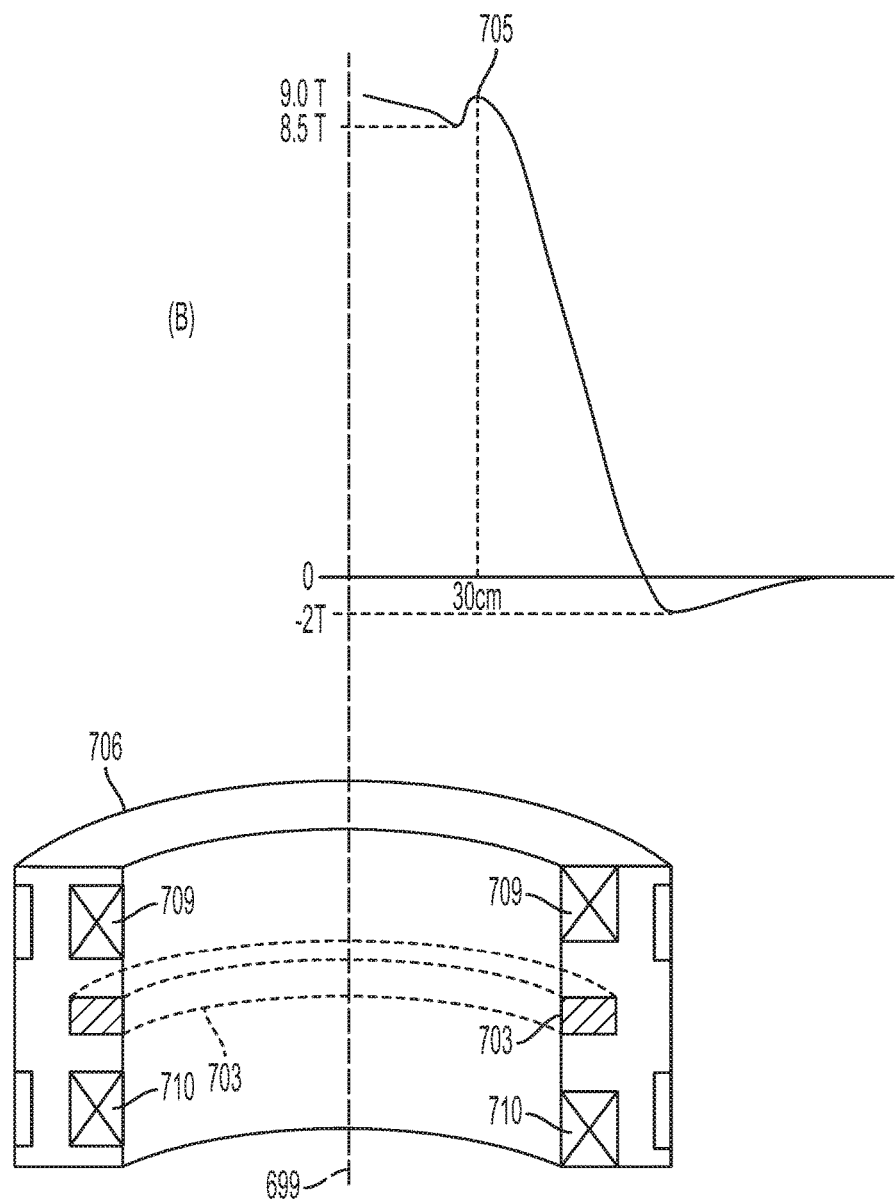
FIG. 16 is a graph showing magnetic field strength versus radial distance from a plasma column, along with a cross-section of an example part of a cryostat of a superconducting magnet.

In more detail, a particle beam orbit approaches and interacts with regenerator 702. As a result of the increased magnetic field, the particle beam turns a bit more there and, instead of being circular, it precesses to the extraction channel. FIG. 16 shows the magnetic field (B) plotted against the radius (r) relative to the particle source 702. As shown in FIG. 16, in this example, B varies from about 9 Tesla (T) to about −2 T. The 9 T occurs at about the center 699 of cavity 700. The polarity of the magnetic field changes after the magnetic field crosses the superconducting coil, resulting in about −2 T on the exterior of the coil, eventually fading to about zero. The magnetic field bump 705 occurs at the point of the regenerator. FIG. 16 also shows the magnetic field plot relative to a cross-section 706 of a reverse bobbin 706 having extraction channel 703 between two superconducting coils 709, 710.

Figure 17:
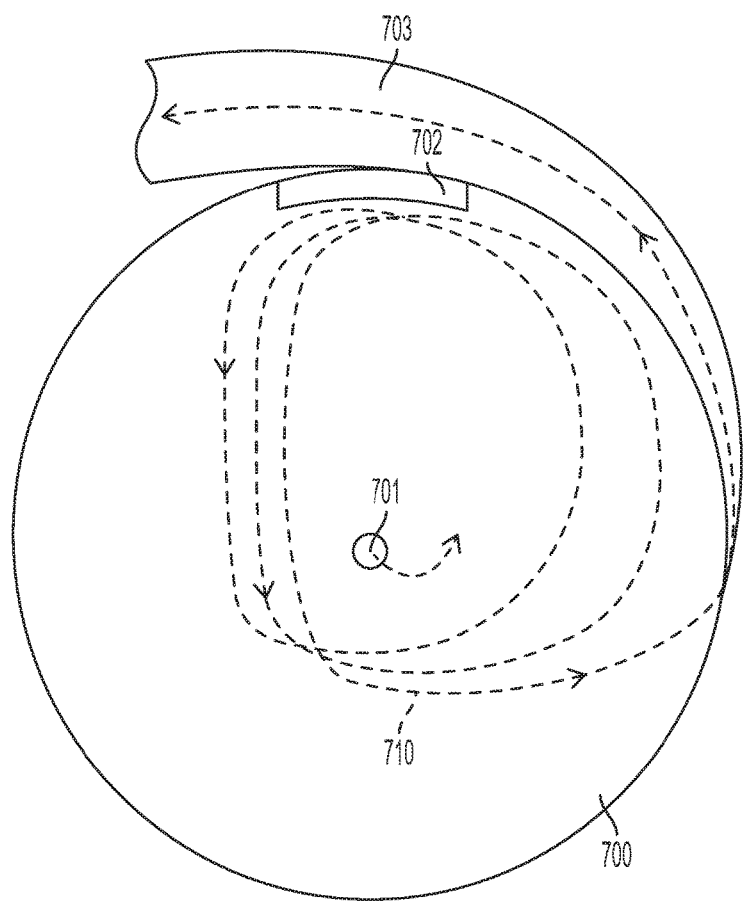
FIG. 17 is a top view of an example acceleration cavity and extraction channel, which depicts orbits moving to enter the extraction channel.

Referring to FIG. 17, regenerator 702 causes changes in the angle and pitch of orbits 710 so that they move toward extraction channel 703. At the point of the extraction channel, the magnetic field strength is sufficiently low to enable the particle beam to enter the extraction channel and to proceed therethrough. Referring back to FIG. 15, extraction channel 703 contains various magnetic structures 711 for adding and/or subtracting dipole fields to direct the entering particle beam through extraction channel 703, to beam shaping elements. Other examples of magnetic structures in the extraction channel include, but are not limited to, structures 107, 109 of FIG. 5.

In order to reach the exit point, the particle beam should have the appropriate amount of energy. The amount of energy required to reach that point may vary based, e.g., on the size of the accelerator and the length of the extraction channel (in this example, the extraction channel is about 1.7 or 2 meters in length). In this regard, at least part of extraction channel 703 is above the superconducting coil. As such, the magnetic field in the extraction channel may change little in response to accelerator rotation. Accordingly, the amount of energy needed for a particle beam to traverse the extraction channel may not change appreciably in response to the rotation of the particle accelerator.

Figure 18:
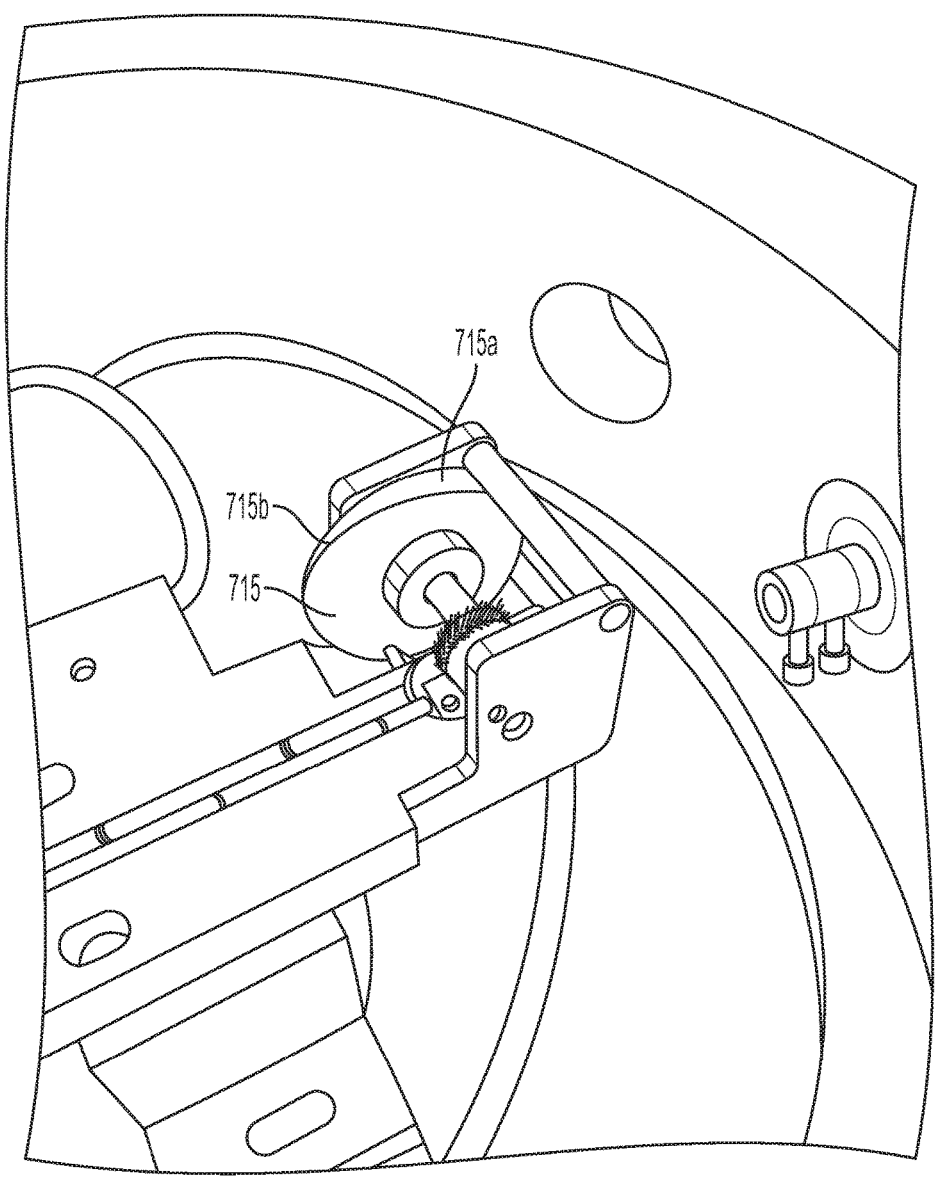
FIG. 18 is a perspective view of an example structure used to change the energy of a particle beam in the extraction channel.
Figure 18A:
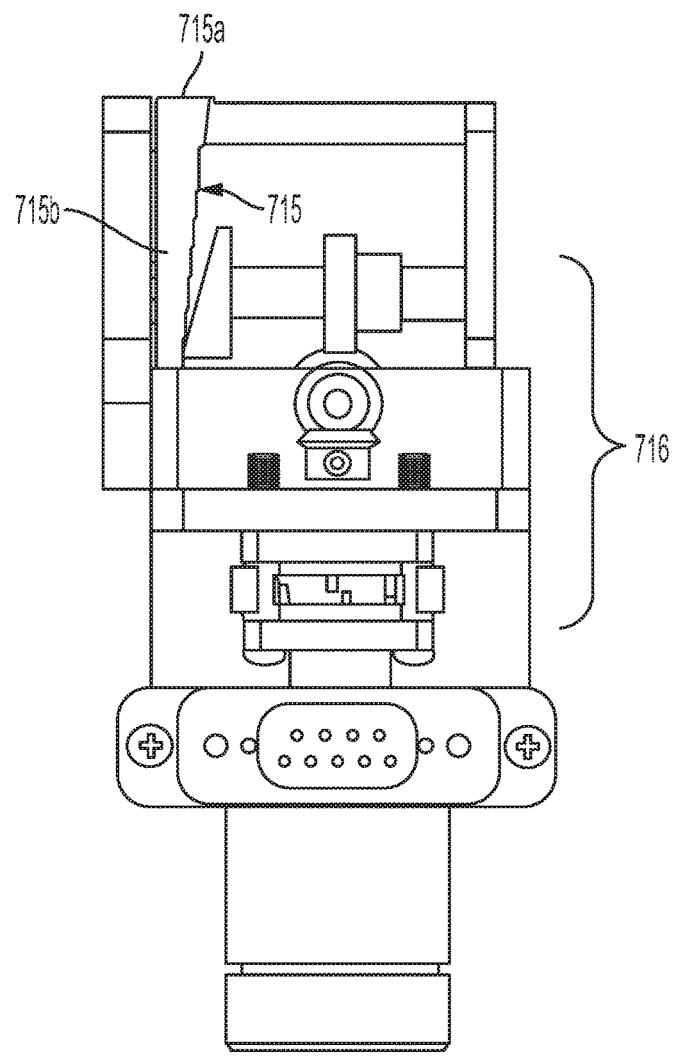
FIG. 18A is a side view of the structure of FIG. 18.

As explained above, as the superconducting coil moves during rotation, orbits that are affected by regenerator 702 change due to gravitational movement of the coil. As noted, this movement can be as little as tenths of millimeters. Nevertheless, as a result, the energy of the particle beam that enters the extraction channel may be different from the energy required to traverse the entire channel. To adjust for this change in the energy of particles entering the extraction channel, a structure 715 may be placed inside, or at the entry point to, extraction channel 703. The structure may be used to absorb excess energy in the particle beam. In this example, structure 715 is a rotatable, variable-thickness wedge, which may have a wheel-like shape. An example of structure 715 is shown in FIGS. 18 and 18A. As shown in these figures, structure 715 may have continuously varying thickness. Alternatively, the thicknesses may vary step-wise.

The structure may be moved (e.g., rotated) to absorb an appropriate amount of energy from a particle beam in/entering the extraction channel. In this implementation, thicker parts 715a of the structure absorb more energy than thinner parts 715b. Accordingly, the structure may be moved (e.g., rotated) to absorb different amounts of energy in a particle beam. In some implementations, the structure may have a part containing no material (e.g., a "zero" thickness), which allows the particle beam to pass unaltered. Alternatively, in such cases, the structure may be moved entirely or partly out of the beam path. In some implementations, the maximum thickness may be on the order of centimeters; however, the maximum thickness will vary from system-to-system based, e.g., on energy absorbing requirements. FIG. 18A also shows a motor 716 that controls an axle to rotate structure 715, e.g., in response to a detected gantry position.

The structure may be made of any appropriate material that is capable of absorbing energy in a particle beam. As noted above, ideally, the structure minimizes scattering of the particle beam in the extraction channel; however, in practice, there may be amounts of scatter that are present and that are tolerable. Examples of materials that may be used for the structure include, but are not limited to, beryllium, plastic containing hydrogen, and carbon. These materials may be used alone, in combination, or in combination with other materials.

The movement (e.g., rotation) of the structure may be computer-controlled using a control system that is part of the broader particle therapy system. Computer control may include generating one or more control signals to control movement of mechanical devices, such as actuators and motors that produce the motion. The rotation of structure 715 may be controlled based on a rotational position of the particle accelerator, as measured by the rotational position of the gantry (see, e.g., FIGS. 1, 11 and 12 showing gantry rotation) on which the particle accelerator is mounted. The various parameters used to set the rotational position of the structure vis-à-vis the position of the gantry may be measured empirically, and programmed into the control system computer.

As noted above, in some implementations, the magnetic field in the extraction channel may change, albeit very little, in response to accelerator rotation. The amount of the change may be, e.g., a few tenths of a percent. In a specific example, this is reflected by a change of about six amperes (amps) of current out of a normal ~2000 amps running through the superconducting coil. This can affect the energy required for a particle beam to traverse the extraction channel. This small change in magnetic field may be adjusted by controlling the current through the superconducting coil or by controlling the rotation of structure 715.

In other implementations, adjusting the energy of particle beams reaching the extraction channel may be achieved by physically moving regenerator 702 so that, at different rotational positions, the regenerator affects different particle orbits. As above, the movement or regenerator 702 may be computer-controlled through a control system that is part of the particle therapy system. For example, the movement of regenerator 702 may be controlled based on a rotational position of the particle accelerator, as measured by the rotational position of the gantry on which the particle accelerator is mounted. The various parameters used to set the location of the regenerator vis-à-vis the rotational position of the gantry may be measured empirically, and programmed into the control system computer. One or more computer-controlled actuators may effect actual movement of the regenerator.

Figure 19:
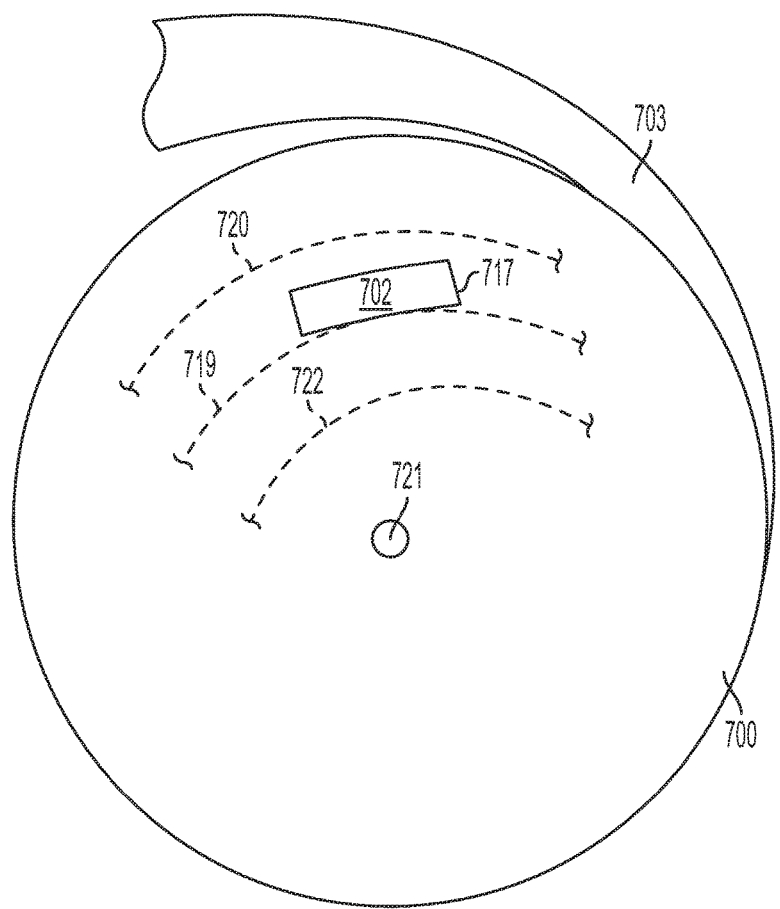
FIGS. 19, 20, and 21 are top views of an example acceleration cavity and extraction channel, which depict moving the regenerator to primarily impact certain orbits of particles in the cavity.
Figure 20:
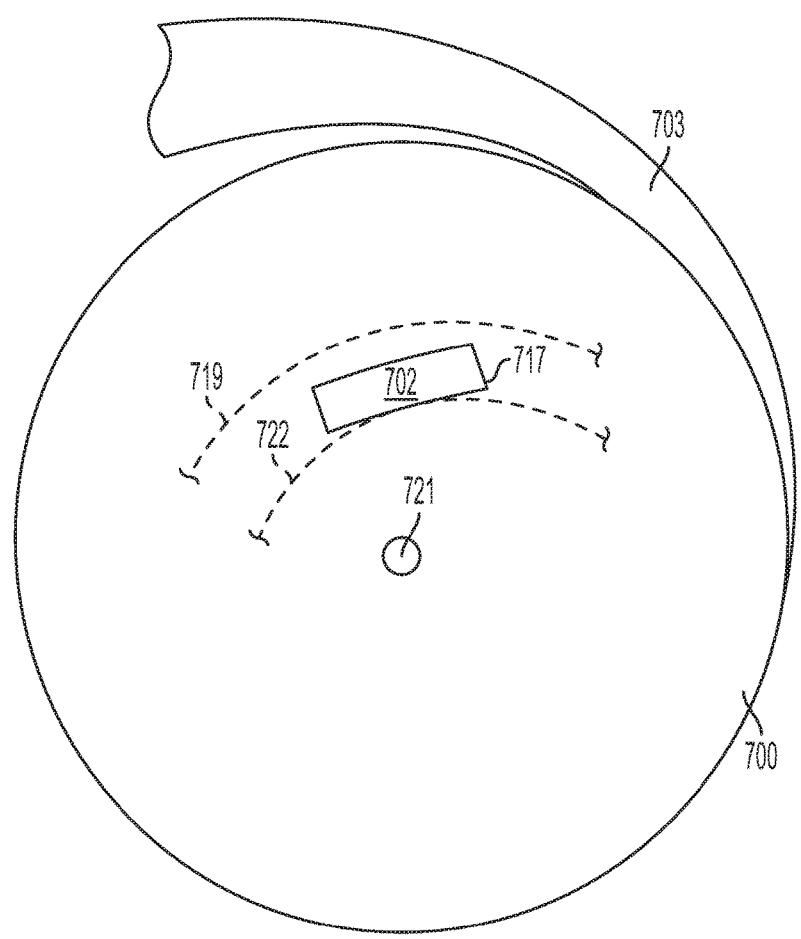
Figure 21:
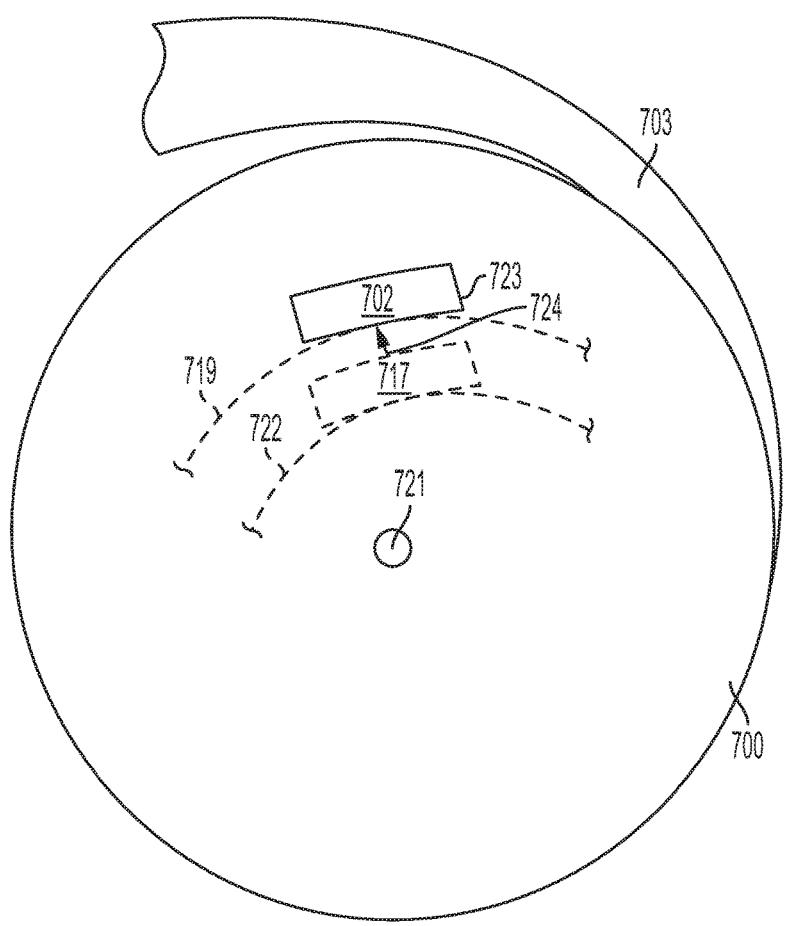

Referring to FIG. 19 for example, regenerator 702 may be positioned at location 717 initially, e.g., at a predefined initial position of the accelerator. In this position, the magnetic field bump produced by the regenerator has a primary impact on orbit 719 (to direct particles at that orbital position to the extraction channel). Orbit 720 is further from the location 721 of the plasma column than orbit 719. Consequently, orbit 720 has higher energy than orbit 719. Orbit 722 is closer to the location 721 of the plasma column than orbit 719. Consequently, orbit 722 has lower energy than orbit 719. As shown in FIG. 20, movement of the superconducting coil as a result of rotation can cause lower-energy orbit 722 to move into the path of regenerator 702 such that regenerator 702 primarily affects orbit 722. However, because orbit 722 is lower energy, it may not be capable of traversing the extraction channel and may impact the inner wall of the extraction channel before exiting. Accordingly, regenerator 702 may be moved from location 717 to location 723 (as depicted by arrow 724 of FIG. 21) so that regenerator 702 again primarily impacts orbit 719. The converse may be true as well. That is, if the superconducting coil moves such that an overly high-energy orbit 720 is primarily impacted by regenerator 702, regenerator 702 may be moved in the other direction (e.g., towards location 721) so that it primarily impacts the lower-energy orbit 719 (which has also moved). Although the figures depict movement of the regenerator in one dimension (radially), the regenerator may be moved in two or three dimensions, e.g., it may be moved in the Cartesian X, Y and/or Z directions.

In other implementations, the orbit that is affected primarily by the regenerator may be changed by altering the magnetic field (the magnetic field bump). This may be done, e.g., by changing the amount of ferromagnetic material in proximity to the regenerator. In an implementation, one or more magnetic shims may be used to alter the shape and/or strength of the magnetic field produced by the regenerator. In this regard, the regenerator may be made of a ferromagnetic material, such as steel (although other materials may be used in place of, or in addition to, steel). The magnetic shims may be a ferromagnetic material that is different from, or the same as, the material of which the regenerator is made.

Figure 22:
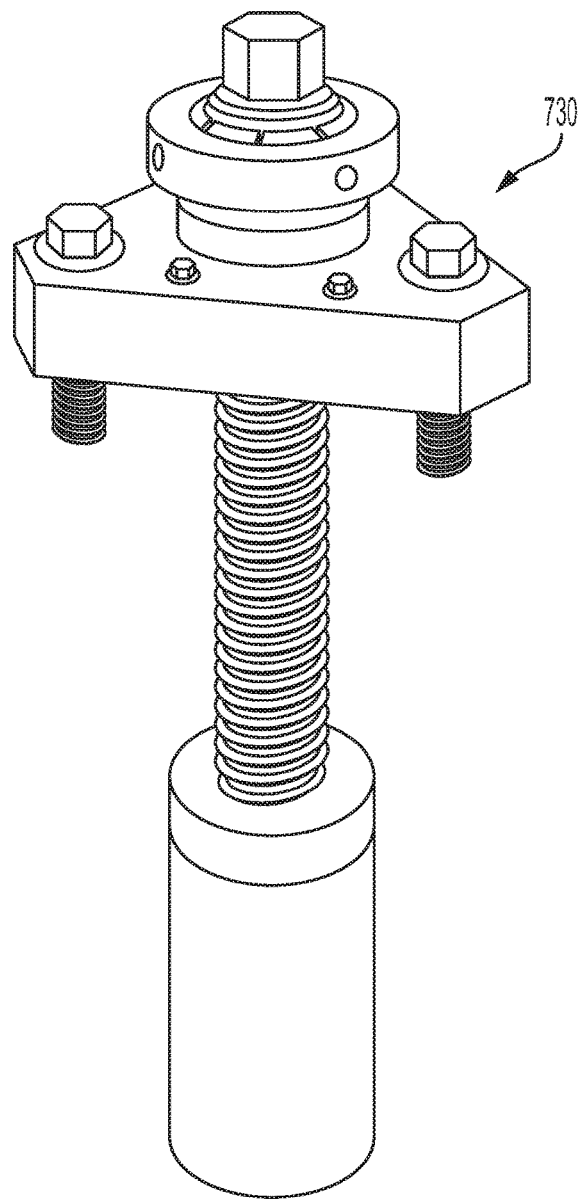
FIG. 22 is a perspective view of an example magnetic shim.
Figure 23:
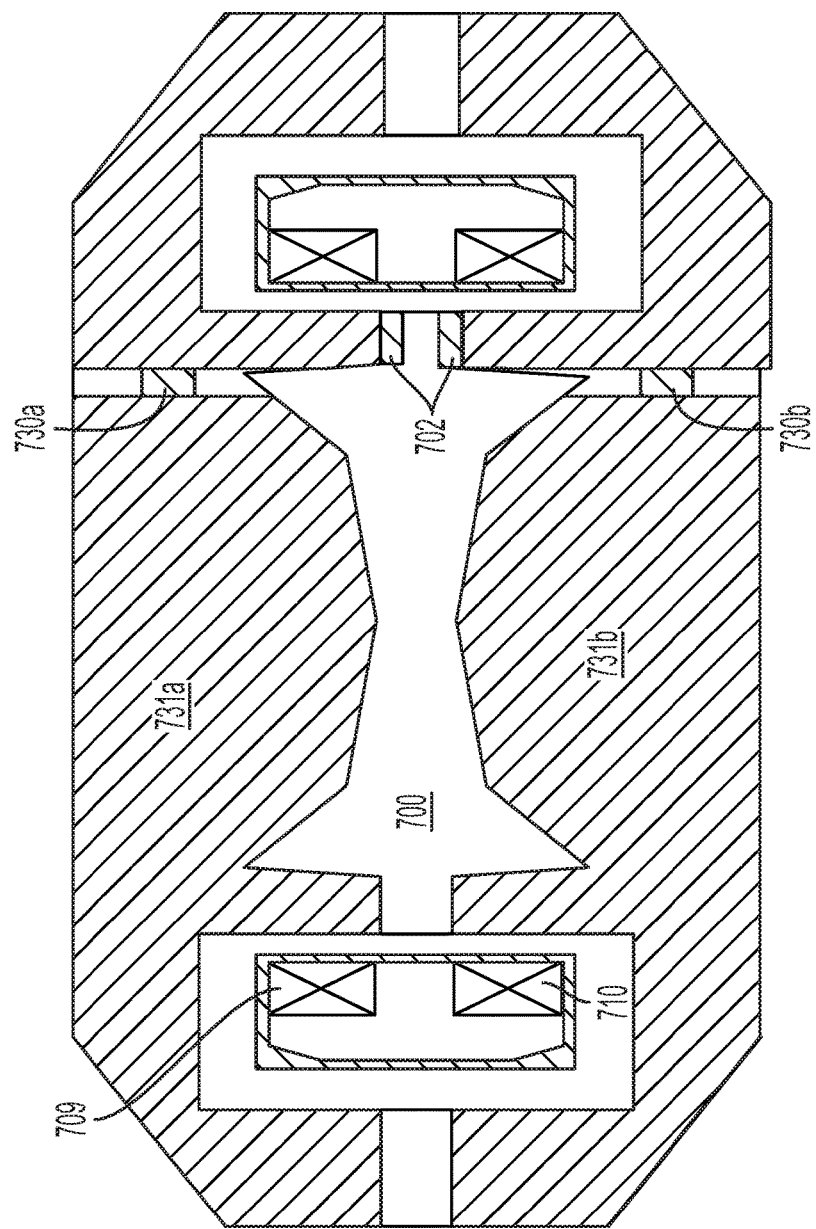
FIG. 23 is cut-away side view of magnetic yokes, an acceleration cavity and a cold mass, which includes magnetic shims.

In this implementation, the magnetic shims includes one or iron or steel magnetic shims. An example is magnetic shim 730 is shown in FIG. 22; however, any appropriate shape may be used. For example, magnetic shim 730 may be in the shape of a rod or may have other appropriate shapes. Referring to FIG. 23, magnetic shims 730a, 730b may be placed in a slot of the corresponding yoke 731a, 731b near to the regenerator 702 or in the regenerator itself. Moving the magnetic shim downward, further inside a slot in the yoke increases the amount of ferromagnetic material near to the regenerator and thereby alters the location and size of the magnetic field bump produced by the regenerator. By contrast, moving a magnetic shim upward and out of the yoke decreases the amount of ferromagnetic material near to the regenerator and thereby alters the location and size of the magnetic field bump produced by the regenerator. Increasing the amount of ferromagnetic material causes the magnetic field bump to be moved inward (towards the plasma column—see, e.g., FIGS. 19 to 21) to thereby primarily affect lower-energy particle orbits. Decreasing the amount of ferromagnetic material causes the magnetic field bump to be moved outward (away the plasma column) to thereby primarily affect higher-energy particle orbits.

The magnetic shims may be permanently screwed into the yoke and held in place there using screws or they may be controlled in real-time. In this regard, movement or the magnetic shim(s) may be computer-controlled through a control system that is part of the particle therapy system. For example, the movement of each magnetic shim 730a, 730b may be controlled based on a rotational position of the particle accelerator, as measured by the rotation position of the gantry on which the particle accelerator is mounted. The various parameters used to set the magnetic shim location vis-à-vis the rotational position of the accelerator may be measured empirically, and programmed into the control system computer. One or more computer-controlled actuators may effect actual movement of the magnetic shim(s). Although only two magnetic shims are depicted, any number of magnetic shims may be used (e.g., one or more).

In some implementations, the magnetic shim(s) (e.g., the magnetic shim(s) described above) may instead be, or include, one or more miniature electromagnets, the current through which is controlled to affect the magnetic field produced by the regenerator in the manner described above. The current through the one or more electromagnets may be computer-controlled through a control system that is part of the particle therapy system. For example, the current may be controlled based on a rotational position of the particle accelerator, as measured by the rotation position of the gantry on which the particle accelerator is mounted. The various parameters used to set the current vis-à-vis the rotational position of the accelerator may be measured empirically, and programmed into the control system computer.

In other implementations, adjusting the energy of particle beams reaching the extraction channel may be achieved by physically moving the cryostat to compensate for movement of the coil as a result of rotation. For example, the cryostat may be moved in a direction opposite to the direction that the coil moves. As above, the movement of the cryostat may be computer-controlled through a control system that is part of the particle therapy system. For example, the movement of cryostat may be controlled based on a rotational position of the particle accelerator, as measured by the rotation position of the gantry on which the particle accelerator is mounted. The various parameters used to set the movement of the cryostat vis-à-vis the rotational position of the gantry may be measured empirically, and programmed into the control system computer. One or more computer-controlled actuators may effect actual movement of the cryostat. Examples of actuators that may be used to move the cryostat, and thus the coils contained therein, are described with respect to FIGS. 34 and 35 below.

Figure 24:
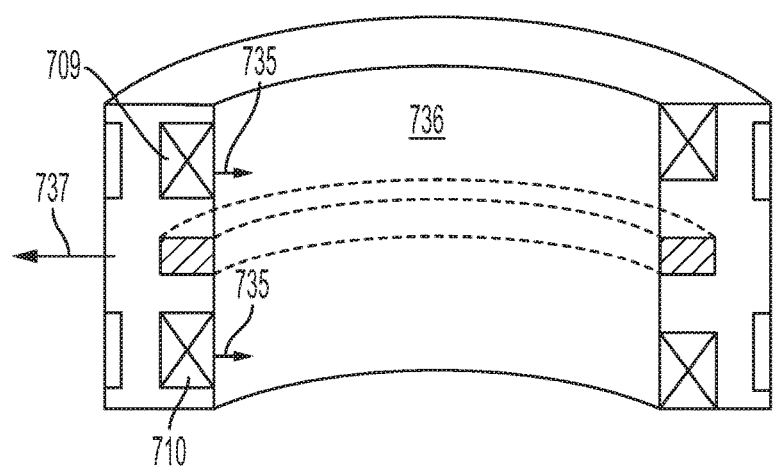
FIG. 24 is a cut-away perspective view of an example part of a cryostat.

Referring to FIG. 24, for example, rotation of the accelerator may cause coils 709, 710 to move in the direction of arrow 735 within their respective chambers. In response, the position of cryostat 736 may be changed, e.g., cryostat 736 may be moved, e.g., in the direction of arrow 737 (e.g., in the opposite direction by an opposite amount). This movement causes a corresponding movement of coil 709, 710, thereby bringing coils 709, 710 back into their original position in proper alignment relative to the regenerator.

The particle accelerator used in the example particle therapy systems described herein may be a variable-energy particle accelerator.

Figure 25:
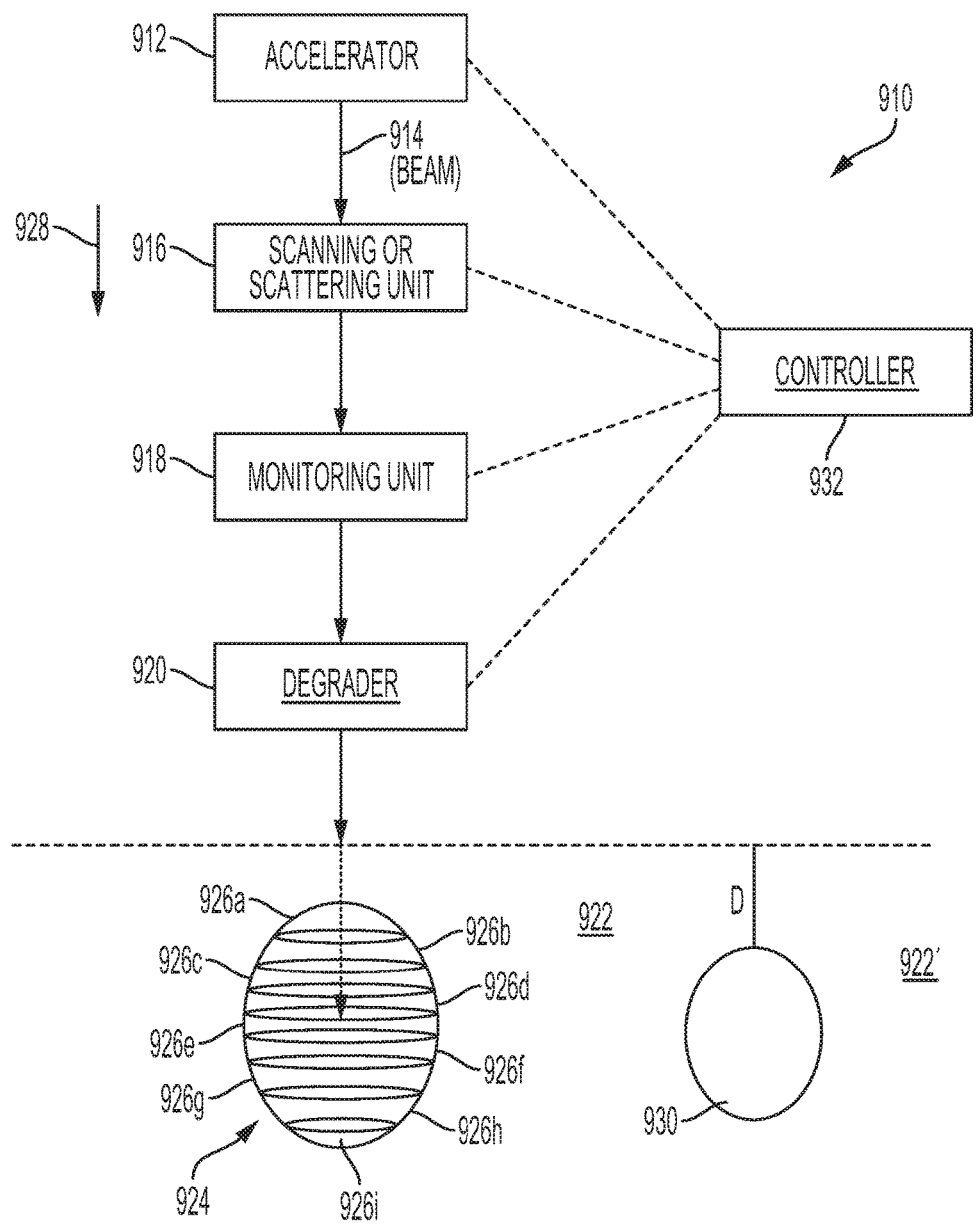
FIG. 25 is a conceptual view of an example particle therapy system that may use a variable-energy particle accelerator.

The energy of the extracted particle beam (the particle beam output from the accelerator) can affect the use of the particle beam during treatment. In some machines, the energy of the particle beam (or particles in the particle beam) does not increase after extraction. However, the energy may be reduced based on treatment needs after the extraction and before the treatment. Referring to FIG. 25, an example treatment system 910 includes an accelerator 912, e.g., a synchrocyclotron, from which a particle (e.g., proton) beam 914 having a variable energy is extracted to irradiate a target volume 924 of a body 922. Optionally, one or more additional devices, such as a scanning unit 916 or a scattering unit 916, one or more monitoring units 918, and an energy degrader 920, are placed along the irradiation direction 928. The devices intercept the cross-section of the extracted beam 914 and alter one or more properties of the extracted beam for the treatment.

A target volume to be irradiated (an irradiation target) by a particle beam for treatment typically has a three-dimensional configuration. In some examples, to carry-out the treatment, the target volume is divided into layers along the irradiation direction of the particle beam so that the irradiation can be done on a layer-by-layer basis. For certain types of particles, such as protons, the penetration depth (or which layer the beam reaches) within the target volume is largely determined by the energy of the particle beam. A particle beam of a given energy does not reach substantially beyond a corresponding penetration depth for that energy. To move the beam irradiation from one layer to another layer of the target volume, the energy of the particle beam is changed.

In the example shown in FIG. 25, the target volume 924 is divided into nine layers 926a-926i along the irradiation direction 928. In an example process, the irradiation starts from the deepest layer 926i, one layer at a time, gradually to the shallower layers and finishes with the shallowest layer 926a. Before application to the body 922, the energy of the particle beam 914 is controlled to be at a level to allow the particle beam to stop at a desired layer, e.g., the layer 926d, without substantially penetrating further into the body or the target volume, e.g., the layers 926e-926i or deeper into the body. In some examples, the desired energy of the particle beam 914 decreases as the treatment layer becomes shallower relative to the particle acceleration. In some examples, the beam energy difference for treating adjacent layers of the target volume 924 is about 3 MeV to about 100 MeV, e.g., about 10 MeV to about 80 MeV, although other differences may also be possible, depending on, e.g., the thickness of the layers and the properties of the beam.

The energy variation for treating different layers of the target volume 924 can be performed at the accelerator 912 (e.g., the accelerator can vary the energy) so that, in some implementations, no additional energy variation is required after the particle beam is extracted from the accelerator 912. So, the optional energy degrader 920 in the treatment system 10 may be eliminated from the system. In some implementations, the accelerator 912 can output particle beams having an energy that varies between about 100 MeV and about 300 MeV, e.g., between about 115 MeV and about 250 MeV. The variation can be continuous or non-continuous, e.g., one step at a time. In some implementations, the variation, continuous or non-continuous, can take place at a relatively high rate, e.g., up to about 50 MeV per second or up to about 20 MeV per second. Non-continuous variation can take place one step at a time with a step size of about 10 MeV to about 90 MeV.

When irradiation is complete in one layer, the accelerator 912 can vary the energy of the particle beam for irradiating a next layer, e.g., within several seconds or within less than one second. In some implementations, the treatment of the target volume 924 can be continued without substantial interruption or even without any interruption. In some situations, the step size of the non-continuous energy variation is selected to correspond to the energy difference needed for irradiating two adjacent layers of the target volume 924. For example, the step size can be the same as, or a fraction of, the energy difference.

In some implementations, the accelerator 912 and the degrader 920 collectively vary the energy of the beam 914. For example, the accelerator 912 provides a coarse adjustment and the degrader 920 provides a fine adjustment or vice versa. In this example, the accelerator 912 can output the particle beam that varies energy with a variation step of about 10-80 MeV, and the degrader 920 adjusts (e.g., reduces) the energy of the beam at a variation step of about 2-10 MeV.

The reduced use (or absence) of the energy degrader, which can include range shifters, helps to maintain properties and quality of the output beam from the accelerator, e.g., beam intensity. The control of the particle beam can be performed at the accelerator. Side effects, e.g., from neutrons generated when the particle beam passes the degrader 920 can be reduced or eliminated.

The energy of the particle beam 914 may be adjusted to treat another target volume 930 in another body or body part 922' after completing treatment in target volume 924. The target volumes 924, 930 may be in the same body (or patient), or may belong to different patients. It is possible that the depth D of the target volume 930 from a surface of body 922' is different from that of the target volume 924. Although some energy adjustment may be performed by the degrader 920, the degrader 920 may only reduce the beam energy and not increase the beam energy.

In this regard, in some cases, the beam energy required for treating target volume 930 is greater than the beam energy required to treat target volume 924. In such cases, the accelerator 912 may increase the output beam energy after treating the target volume 924 and before treating the target volume 930. In other cases, the beam energy required for treating target volume 930 is less than the beam energy required to treat target volume 924. Although the degrader 920 can reduce the energy, the accelerator 912 can be adjusted to output a lower beam energy to reduce or eliminate the use of the degrader 920. The division of the target volumes 924, 930 into layers can be different or the same. And the target volume 930 can be treated similarly on a layer by layer basis to the treatment of the target volume 924.

The treatment of the different target volumes 924, 930 on the same patient may be substantially continuous, e.g., with the stop time between the two volumes being no longer than about 30 minutes or less, e.g., 25 minutes or less, 20 minutes or less, 15 minutes or less, 10 minutes or less, 5 minutes or less, or 1 minute or less. As is explained herein, the accelerator 912 can be mounted on a movable gantry and the movement of the gantry can move the accelerator to aim at different target volumes. In some situations, the accelerator 912 can complete the energy adjustment of the output beam 914 during the time the treatment system makes adjustment (such as moving the gantry) after completing the treatment of the target volume 924 and before starting treating the target volume 930. After the alignment of the accelerator and the target volume 930 is done, the treatment can begin with the adjusted, desired beam energy. Beam energy adjustment for different patients can also be completed relatively efficiently. In some examples, all adjustments, including increasing/reducing beam energy and/or moving the gantry are done within about 30 minutes, e.g., within about 25 minutes, within about 20 minutes, within about 15 minutes, within about 10 minutes or within about 5 minutes.

In the same layer of a target volume, an irradiation dose is applied by moving the beam across the two-dimensional surface of the layer (which is sometimes called scanning beam) using a scanning unit 916. Alternatively, the layer can be irradiated by passing the extracted beam through one or more scatterers of the scattering unit 16 (which is sometimes called scattering beam).

Beam properties, such as energy and intensity, can be selected before a treatment or can be adjusted during the treatment by controlling the accelerator 912 and/or other devices, such as the scanning unit/scatterer(s) 916, the degrader 920, and others not shown in the figures. In this example implementation, as in the example implementations described above, system 910 includes a controller 932, such as a computer, in communication with one or more devices in the system. Control can be based on results of the monitoring performed by the one or more monitors 918, e.g., monitoring of the beam intensity, dose, beam location in the target volume, etc. Although the monitors 918 are shown to be between the device 916 and the degrader 920, one or more monitors can be placed at other appropriate locations along the beam irradiation path. Controller 932 can also store a treatment plan for one or more target volumes (for the same patient and/or different patients). The treatment plan can be determined before the treatment starts and can include parameters, such as the shape of the target volume, the number of irradiation layers, the irradiation dose for each layer, the number of times each layer is irradiated, etc. The adjustment of a beam property within the system 910 can be performed based on the treatment plan. Additional adjustment can be made during the treatment, e.g., when deviation from the treatment plan is detected.

In some implementations, the accelerator 912 is configured to vary the energy of the output particle beam by varying the magnetic field in which the particle beam is accelerated. In an example implementation, one or more sets of coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In other implementations, some sets of coils, such as the set for the fixed electrical current, are superconducting, while other sets of coils, such as the one or more sets for the variable current, are non-superconducting. In some examples, all sets of coils are non-superconducting.

Generally, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The scaling of the magnetic field to the current can allow the variation of the beam energy to be carried out relatively precisely, although sometimes minor adjustment other than the input current may be performed.

In some implementations, to output particle beams having a variable energy, the accelerator 912 is configured to apply RF voltages that sweep over different ranges of frequencies, with each range corresponding to a different output beam energy. For example, if the accelerator 912 is configured to produce three different output beam energies, the RF voltage is capable of sweeping over three different ranges of frequencies. In another example, corresponding to continuous beam energy variations, the RF voltage sweeps over frequency ranges that continuously change. The different frequency ranges may have different lower frequency and/or upper frequency boundaries.

The extraction channel may be configured to accommodate the range of different energies produced by the variable-energy particle accelerator. Particle beams having different energies can be extracted from the accelerator 912 without altering the features of the regenerator that is used for extracting particle beams having a single energy. In other implementations, to accommodate the variable particle energy, the regenerator can be moved to disturb (e.g., change) different particle orbits in the manner described above and/or iron rods (magnetic shims) can be added or removed to change the magnetic field bump provided by the regenerator. More specifically, different particle energies will typically be at different particle orbits within the cavity. By moving the regenerator in the manner described herein, it is possible to intercept a particle orbit at a specified energy and thereby provide the correct perturbation of that orbit so that particles at the specified energy reach the extraction channel. In some implementations, movement of the regenerator (and/or addition/removal of magnetic shims) is performed in real-time to match real-time changes in the particle beam energy output by the accelerator. In other implementations, particle energy is adjusted on a per-treatment basis, and movement of the regenerator (and/or addition/removal of magnetic shims) is performed in advance of the treatment. In either case, movement of the regenerator (and/or addition/removal of magnetic shims) may be computer controlled. For example, a computer may control one or more motors that effect movement of the regenerator and/or magnetic shims.

In some implementations, the regenerator is implemented using one or more magnetic shims that are controllable to move to the appropriate location(s).

In some implementations, structure 715 (described above) is controlled to accommodate the different energies produced by the particle accelerator. For example, structure 715 may be rotated so that an appropriate thickness intercepts a particle beam having a particular energy. Structure 715 thus absorbs at least some of the energy in the particle beam, enabling the particle beam to traverse the extraction channel, as described above.

As an example, table 1 shows three example energy levels at which example accelerator 912 can output particle beams. The corresponding parameters for producing the three energy levels are also listed. In this regard, the magnet current refers to the total electrical current applied to the one or more coil sets in the accelerator 912; the maximum and minimum frequencies define the ranges in which the RF voltage sweeps; and "r" is the radial distance of a location to a center of the cavity in which the particles are accelerated.

TABLE 1

Examples of beam energies and respective parameters.

| Beam Energy (MeV) | Magnet Current (Amps) | Maximum Frequency (MHz) | Minimum Frequency (MHz) | Magnetic Field at r = 0 mm (Tesla) | Magnetic Field at r = 298 mm (Tesla) |
|---|---|---|---|---|---|
| 250 | 1990 | 132 | 99 | 8.7 | 8.2 |
| 235 | 1920 | 128 | 97 | 8.4 | 8.0 |
| 211 | 1760 | 120 | 93 | 7.9 | 7.5 |

Details that may be included in an example particle accelerator that produces charged particles having variable energies are described below. The accelerator can be a synchrocyclotron and the particles may be protons. The particles may be output as pulsed beams. The energy of the beam output from the particle accelerator can be varied during the treatment of one target volume in a patient, or between treatments of different target volumes of the same patient or different patients. In some implementations, settings of the accelerator are changed to vary the beam energy when no beam (or particles) is output from the accelerator. The energy variation can be continuous or non-continuous over a desired range.

Referring to the example shown in FIG. 1, the particle accelerator (synchrocyclotron 502), which may be a variable-energy particle accelerator like accelerator 912 described above, may be configured to particle beams that have a variable energy. The range of the variable energy can have an upper boundary that is about 200 MeV to about 300 MeV or higher, e.g., 200 MeV, about 205 MeV, about 210 MeV, about 215 MeV, about 220 MeV, about 225 MeV, about 230 MeV, about 235 MeV, about 240 MeV, about 245 MeV, about 250 MeV, about 255 MeV, about 260 MeV, about 265 MeV, about 270 MeV, about 275 MeV, about 280 MeV, about 285 MeV, about 290 MeV, about 295 MeV, or about 300 MeV or higher. The range can also have a lower boundary that is about 100 MeV or lower to about 200 MeV, e.g., about 100 MeV or lower, about 105 MeV, about 110 MeV, about 115 MeV, about 120 MeV, about 125 MeV, about 130 MeV, about 135 MeV, about 140 MeV, about 145 MeV, about 150 MeV, about 155 MeV, about 160 MeV, about 165 MeV, about 170 MeV, about 175 MeV, about 180 MeV, about 185 MeV, about 190 MeV, about 195 MeV, about 200 MeV.

In some examples, the variation is non-continuous and the variation step can have a size of about 10 MeV or lower, about 15 MeV, about 20 MeV, about 25 MeV, about 30 MeV, about 35 MeV, about 40 MeV, about 45 MeV, about 50 MeV, about 55 MeV, about 60 MeV, about 65 MeV, about 70 MeV, about 75 MeV, or about 80 MeV or higher. Varying the energy by one step size can take no more than 30 minutes, e.g., about 25 minutes or less, about 20 minutes or less, about 15 minutes or less, about 10 minutes or less, about 5 minutes or less, about 1 minute or less, or about 30 seconds or less. In other examples, the variation is continuous and the accelerator can adjust the energy of the particle beam at a relatively high rate, e.g., up to about 50 MeV per second, up to about 45 MeV per second, up to about 40 MeV per second, up to about 35 MeV per second, up to about 30 MeV per second, up to about 25 MeV per second, up to about 20 MeV per second, up to about 15 MeV per second, or up to about 10 MeV per second. The accelerator can be configured to adjust the particle energy both continuously and non-continuously. For example, a combination of the continuous and non-continuous variation can be used in a treatment of one target volume or in treatments of different target volumes. Flexible treatment planning and flexible treatment can be achieved.

A particle accelerator that outputs a particle beam having a variable energy can provide accuracy in irradiation treatment and reduce the number of additional devices (other than the accelerator) used for the treatment. For example, the use of degraders for changing the energy of an output particle beam may be reduced or eliminated. The properties of the particle beam, such as intensity, focus, etc. can be controlled at the particle accelerator and the particle beam can reach the target volume without substantial disturbance from the additional devices. The relatively high variation rate of the beam energy can reduce treatment time and allow for efficient use of the treatment system.

Figure 28:
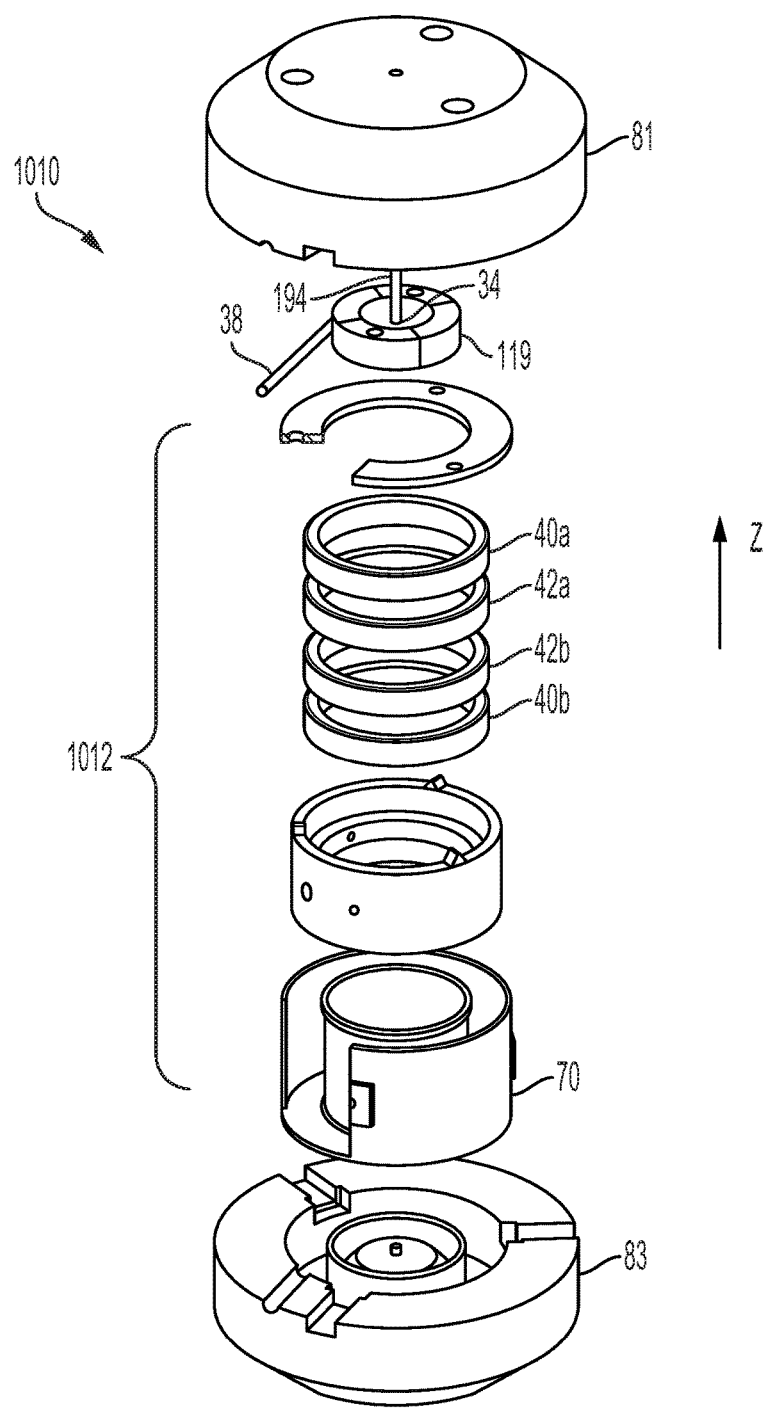
FIG. 28 is a perspective, exploded view of an example magnet system that may be used in a variable-energy particle accelerator.

In some implementations, the accelerator, such as the synchrocyclotron 502 of FIG. 1, accelerates particles or particle beams to variable energy levels by varying the magnetic field in the accelerator, which can be achieved by varying the electrical current applied to coils for generating the magnetic field. As shown in FIGS. 3, 4, 5, 6, and 7, example synchrocyclotron 10 (502 in FIG. 1) includes a magnet system that contains a particle source 90, a radiofrequency drive system 91, and a beam extraction system 38. FIG. 28 shows an example of a magnet system that may be used in a variable-energy accelerator. In this example implementation, the magnetic field established by the magnet system 1012 can vary by about 5% to about 35% of a maximum value of the magnetic field that two sets of coils 40a and 40b, and 42a and 42b are capable of generating. The magnetic field established by the magnet system has a shape appropriate to maintain focus of a contained proton beam using a combination of the two sets of coils and a pair of shaped ferromagnetic (e.g., low carbon steel) structures, examples of which are provided above.

Each set of coils may be a split pair of annular coils to receive electrical current. In some situations, both sets of coils are superconducting. In other situations, only one set of the coils is superconducting and the other set is non-superconducting or normal conducting (also discussed further below). It is also possible that both sets of coils are non-superconducting. Suitable superconducting materials for use in the coils include niobium-3 tin (Nb3Sn) and/or niobium-titanium. Other normal conducting materials can include copper. Examples of the coil set constructions are described further below.

The two sets of coils can be electrically connected serially or in parallel. In some implementations, the total electrical current received by the two sets of coils can include about 2 million ampere turns to about 10 million ampere turns, e.g., about 2.5 to about 7.5 million ampere turns or about 3.75 million ampere turns to about 5 million ampere turns. In some examples, one set of coils is configured to receive a fixed (or constant) portion of the total variable electrical current, while the other set of coils is configured to receive a variable portion of the total electrical current. The total electrical current of the two coil sets varies with the variation of the current in one coil set. In other situations, the electrical current applied to both sets of coils can vary. The variable total current in the two sets of coils can generate a magnetic field having a variable magnitude, which in turn varies the acceleration pathways of the particles and produces particles having variable energies.

Generally, the magnitude of the magnetic field generated by the coil(s) is scalable to the magnitude of the total electrical current applied to the coil(s). Based on the scalability, in some implementations, linear variation of the magnetic field strength can be achieved by linearly changing the total current of the coil sets. The total current can be adjusted at a relatively high rate that leads to a relatively high-rate adjustment of the magnetic field and the beam energy.

In the example reflected in Table 1 above, the ratio between values of the current and the magnetic field at the geometric center of the coil rings is: 1990:8.7 (approximately 228.7:1); 1920:8.4 (approximately 228.6:1); 1760:7.9 (approximately 222.8:1). Accordingly, adjusting the magnitude of the total current applied to a superconducting coil(s) can proportionally (based on the ratio) adjust the magnitude of the magnetic field.

Figure 26:
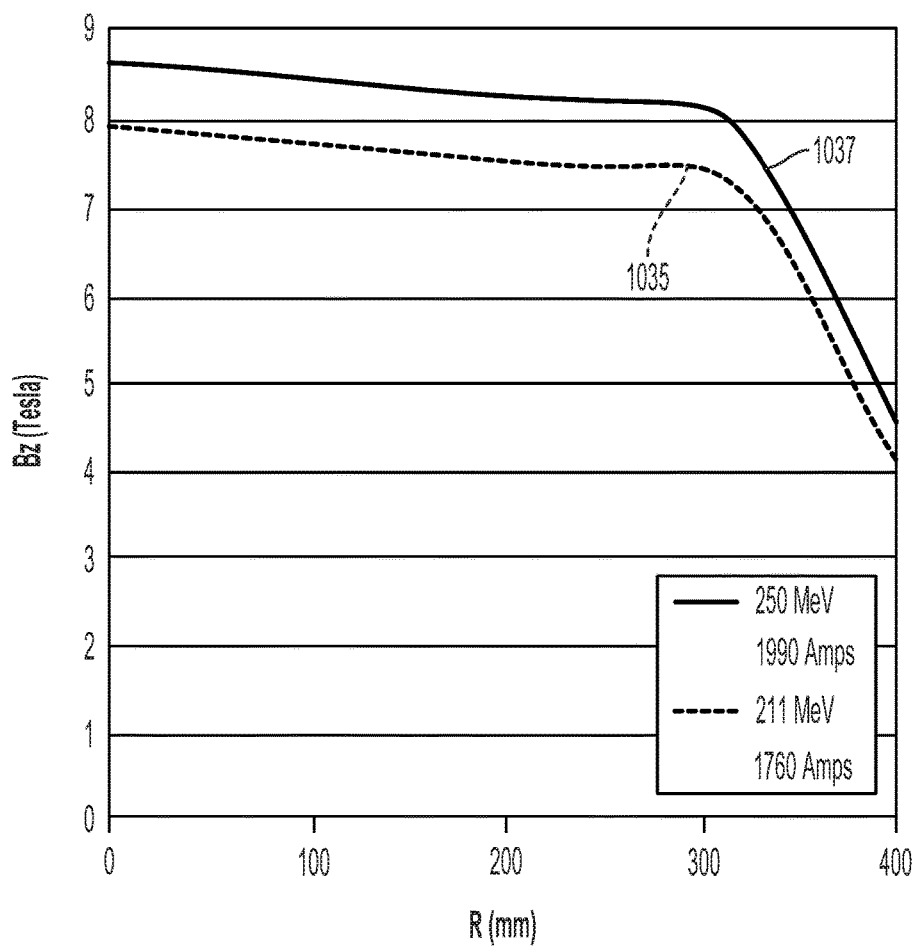
FIG. 26 is an example graph showing energy and current for variations in magnetic field and distance in a particle accelerator.

The scalability of the magnetic field to the total electrical current in the example of Table 1 is also shown in the plot of FIG. 26, where BZ is the magnetic field along the Z direction; and R is the radial distance measured from a geometric center of the coil rings along a direction perpendicular to the Z direction. The magnetic field has the highest value at the geometric center, and decreases as the distance R increases. The curves 1035, 1037 represent the magnetic field generated by the same coil sets receiving different total electrical current: 1760 Amperes and 1990 Amperes, respectively. The corresponding energies of the extracted particles are 211 MeV and 250 MeV, respectively. The two curves 1035, 1037 have substantially the same shape and the different parts of the curves 1035, 1037 are substantially parallel. As a result, either the curve 1035 or the curve 1037 can be linearly shifted to substantially match the other curve, indicating that the magnetic field is scalable to the total electrical current applied to the coil sets.

In some implementations, the scalability of the magnetic field to the total electrical current may not be perfect. For example, the ratio between the magnetic field and the current calculated based on the example shown in Table 1 is not constant. Also, as shown in FIG. 26, the linear shift of one curve may not perfectly match the other curve. In some implementations, the total current is applied to the coil sets under the assumption of perfect scalability. The target magnetic field (under the assumption of perfect scalability) can be generated by additionally altering the features, e.g., geometry, of the coils to counteract the imperfection in the scalability. As one example, ferromagnetic (e.g., iron) rods (magnetic shims) can be inserted or removed from one or both of the magnetic structures. The features of the coils can be altered at a relatively high rate so that the rate of the magnetic field adjustment is not substantially affected as compared to the situation in which the scalability is perfect and only the electrical current needs to be adjusted. In the example of iron rods, the rods can be added or removed at the time scale of seconds or minutes, e.g., within 5 minutes, within 1 minute, less than 30 seconds, or less than 1 second.

In some implementations, settings of the accelerator, such as the current applied to the coil sets, can be chosen based on the substantial scalability of the magnetic field to the total electrical current in the coil sets.

Generally, to produce the total current that varies within a desired range, any combination of current applied to the two coil sets can be used. In an example, the coil set 42a, 42b can be configured to receive a fixed electrical current corresponding to a lower boundary of a desired range of the magnetic field. In the example shown in table 1, the fixed electrical current is 1760 Amperes. In addition, the coil set 40a, 40b can be configured to receive a variable electrical current having an upper boundary corresponding to a difference between an upper boundary and a lower boundary of the desired range of the magnetic field. In the example shown in table 1, the coil set 40a, 40b is configured to receive electrical current that varies between 0 Ampere and 230 Amperes.

In another example, the coil set 42a, 42b can be configured to receive a fixed electrical current corresponding to an upper boundary of a desired range of the magnetic field. In the example shown in table 1, the fixed current is 1990 Amperes. In addition, the coil set 40a, 40b can be configured to receive a variable electrical current having an upper boundary corresponding to a difference between a lower boundary and an upper boundary of the desired range of the magnetic field. In the example shown in table 1, the coil set 40a, 40b is configured to receive electrical current that varies between −230 Ampere and 0 Ampere.

The total variable magnetic field generated by the variable total current for accelerating the particles can have a maximum magnitude greater than 4 Tesla, e.g., greater than 5 Tesla, greater than 6 Tesla, greater than 7 Tesla, greater than 8 Tesla, greater than 9 Tesla, or greater than 10 Tesla, and up to about 20 Tesla or higher, e.g., up to about 18 Tesla, up to about 15 Tesla, or up to about 12 Tesla. In some implementations, variation of the total current in the coil sets can vary the magnetic field by about 0.2 Tesla to about 4.2 Tesla or more, e.g., about 0.2 Tesla to about 1.4 Tesla or about 0.6 Tesla to about 4.2 Tesla. In some situations, the amount of variation of the magnetic field can be proportional to the maximum magnitude.

Figure 27:
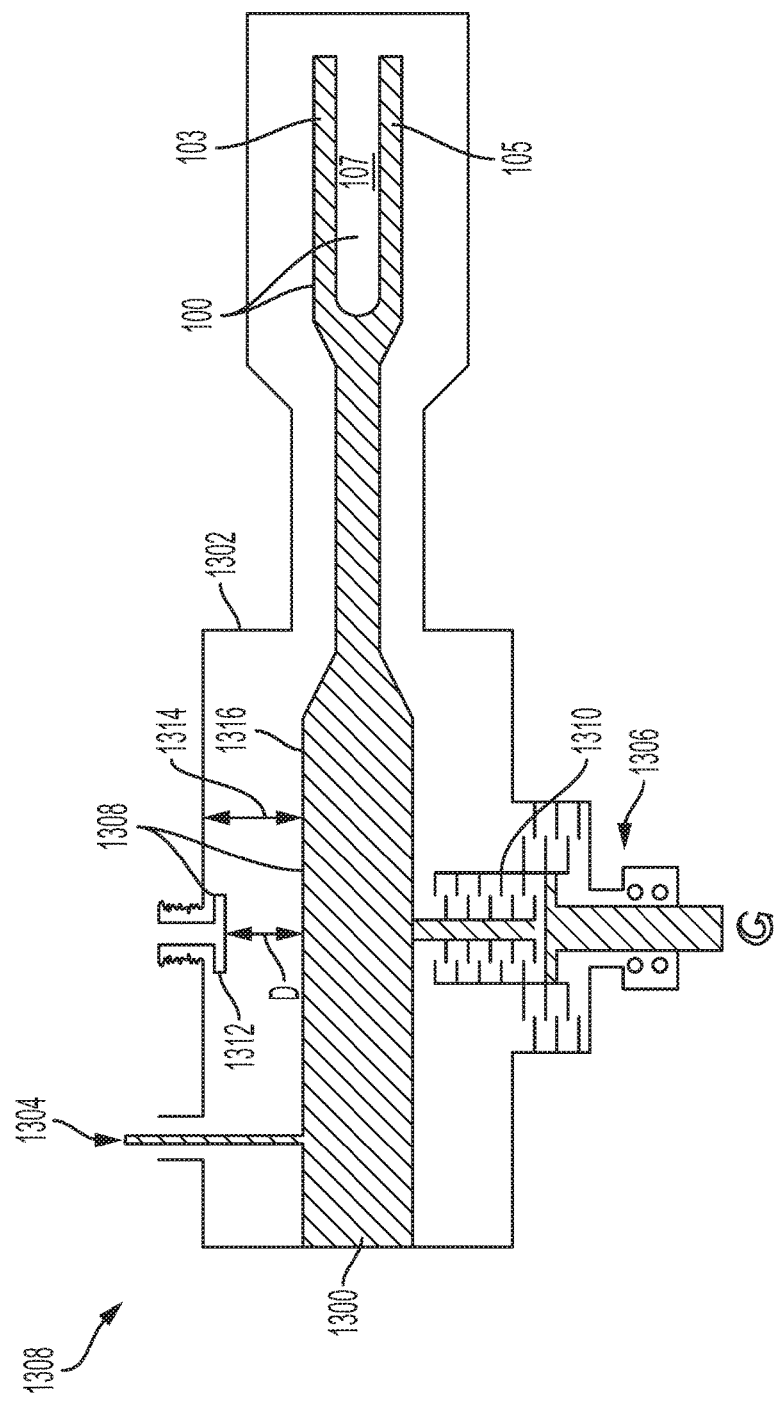
FIG. 27 is a side view of an example structure for sweeping voltage on a dee plate over a frequency range for each energy level of a particle beam, and for varying the frequency range when the particle beam energy is varied.

FIG. 27 shows an example RF structure for sweeping the voltage on the dee plate 100 over an RF frequency range for each energy level of the particle beam, and for varying the frequency range when the particle beam energy is varied. The semicircular surfaces 103, 105 of the dee plate 100 are connected to an inner conductor 1300 and housed in an outer conductor 1302. The high voltage is applied to the dee plate 100 from a power source (not shown, e.g., an oscillating voltage input) through a power coupling device 1304 that couples the power source to the inner conductor. In some implementations, the coupling device 1304 is positioned on the inner conductor 1300 to provide power transfer from the power source to the dee plate 100. In addition, the dee plate 100 is coupled to variable reactive elements 1306, 1308 to perform the RF frequency sweep for each particle energy level, and to change the RF frequency range for different particle energy levels.

The variable reactive element 1306 can be a rotating capacitor that has multiple blades 1310 rotatable by a motor (not shown). By meshing or unmeshing the blades 1310 during each cycle of RF sweeping, the capacitance of the RF structure changes, which in turn changes the resonant frequency of the RF structure. In some implementations, during each quarter cycle of the motor, the blades 1310 mesh with the each other. The capacitance of the RF structure increases and the resonant frequency decreases. The process reverses as the blades 1310 unmesh. As a result, the power required to generate the high voltage applied to the dee plate 103 and necessary to accelerate the beam can be reduced by a large factor. In some implementations, the shape of the blades 1310 is machined to form the required dependence of resonant frequency on time.

The RF frequency generation is synchronized with the blade rotation by sensing the phase of the RF voltage in the resonator, keeping the alternating voltage on the dee plates close to the resonant frequency of the RF cavity. (The dummy dee is grounded and is not shown in FIG. 27).

The variable reactive element 1308 can be a capacitor formed by a plate 1312 and a surface 1316 of the inner conductor 1300. The plate 1312 is movable along a direction 1314 towards or away from the surface 1316. The capacitance of the capacitor changes as the distance D between the plate 1312 and the surface 1316 changes. For each frequency range to be swept for one particle energy, the distance D is at a set value, and to change the frequency range, the plate 1312 is moved corresponding to the change in the energy of the output beam.

In some implementations, the inner and outer conductors 1300, 1302 are formed of a metallic material, such as copper, aluminum, or silver. The blades 1310 and the plate 1312 can also be formed of the same or different metallic materials as the conductors 1300, 1302. The coupling device 1304 can be an electrical conductor. The variable reactive elements 1306, 1308 can have other forms and can couple to the dee plate 100 in other ways to perform the RF frequency sweep and the frequency range alteration. In some implementations, a single variable reactive element can be configured to perform the functions of both the variable reactive elements 1306, 1308. In other implementations, more than two variable reactive elements can be used.

Also described herein are examples of systems for controlling positions of magnet coils including, but not limited to, the magnet coils described with respect to the systems of FIGS. 1 to 28. In general, a magnet may include one or more coils that conduct current to generate a magnetic field. Movement, including but not limited to, full or partial rotation of the magnet, may result in unintended displacement of the coils. For example, gravitational forces experienced during motion may cause a coil to move in a way that was neither desired nor predicted. Other factors may also cause undesirable or unpredicted coil displacement as well. For example, the magnet structure may be changed, e.g., components may be substituted or components may become loose or settled. Coil displacement can alter the magnetic field produced by the magnet in unexpected or unwanted ways. In some examples, the shape and/or intensity of the magnetic field produced using displaced coils may be different from those that were intended. An alteration of the magnetic field can adversely impact the operation of a system employing the magnet. As indicated, in some applications, even very small displacements—e.g., in the submillimeter range—can have a consequential impact.

Accordingly, the example systems described herein may be employed to compensate for, e.g., to correct, displacement of one or more magnet coils. The example systems described herein support moving magnet coils to correct for displacement caused by gravitational forces including, but not limited to, those resulting from full or partial rotation of the magnet. However, the coil positioning systems are not limited to use in this context, and may be used in any appropriate context to reposition magnet coils or other electromagnetic structures. The example coil positioning systems may be configured to produce coil movement at any appropriate granularity, e.g., from sub-millimeter movement to movement on the order of millimeters, centimeters, decimeters, meters, and so forth.

In this regard, compensating for, e.g., correcting, displacement of one or more magnet coils may include moving the coils back to their original (e.g., a predefined) position or it may include moving the coils to any appropriate position to produce a desired magnetic field shape and/or magnitude. For example, the ultimate position to which the coils may be moved may, or may not, be their original position relative to a reference point. Rather, movement may be performed in order to adjust the magnetic field distribution of the coils so that the magnetic field distribution is one that is desired for a particular application. In some implementations, the coils(s) may be moved to arrive at a target distribution for the magnetic field (e.g., one that is desired for a particular application). In some implementations, the target distribution includes a distribution that deviates by no more, or no less, than an acceptable predefined amount from the nominal target.

In example implementations, the coil positioning system includes a physical coupling to a coil (or coils) to be moved. This physical coupling can be a direct physical connection between a device configured to move the coil, or an indirect physical connection that includes one or more intervening structures between the coil and the device configured to move the coil. In any case, an example physical coupling is configured and arranged, and connected to the coil, so that appropriate force applied to the physical coupling causes movement of the coil. In some implementations, the force may include pulling on the physical coupling to produce movement. For example, the physical coupling may include one or more straps or other members to which tension may be increased to produce movement of the coils. In some implementations, the force may include pushing on the physical coupling to produce movement. For, example, the physical coupling may include one or more rigid members that respond to applied pressure to produce movement of the coil by pushing the coil. The physical coupling may include any appropriate combination of rigid, semi-rigid, and non-rigid couplings.

Movement of the coil via the physical coupling may be computer-controlled. For example, one or more processing devices (referred to as a "processing device") may execute appropriate instructions to control movement of the coil via the physical coupling. A processing device may receive information about a coil's position before, during, and after movement, and control the physical positioning of the coil so that the coil ends-up in the correct position.

The information about the coil's position may include, or be, measurements indicative of coil position or other information from which the coil's position may be determined or inferred. In some implementations, the coil positioning system may include the one or more displacement sensors, which may be mounted to a housing that holds the magnet or to another appropriate structure, to obtain measurements of positions of the coil(s) (e.g., relative to the housing) before, during, and after movement (e.g., rotation) of the magnet. Examples of displacement sensors include, but are not limited to, optical sensors. The measurements obtained by the sensors may be used by the processing device to determine the position of the coil(s) before, during, and after movement, and thereby to determine if there if there has been unintended movement. The coil positioning system may then control the position of the coil(s) via the physical coupling to move the coil(s) to their intended position(s). For example, the coils may be moved to predefined or other appropriate positions within the housing in order to adjust (e.g., correct) a magnetic field distribution of the coils.

In some implementations, the coil positioning system may include one or more magnetic field sensors mounted to the housing or to another appropriate structure. Examples of magnetic field sensors include, but are not limited to, Hall effect sensors. The magnetic field sensors may be configured to detect a change in the magnetic field generated by the coil(s) relative to the magnetic field sensors. This detected change in the magnetic field may be indicative of the movement of coil(s) (e.g., relative to the housing) or some other unwanted or unintended cause, and may be used to determine the magnitude and direction of that movement. For example, the processing device may have access to data representing the expected magnitude and shape of a magnetic field for a particular orientation of the magnet. The magnetic field detected by the magnetic field sensors may also be represented by data that is accessible to the processing device. The processing device may use the data about the expected magnetic field and the data about the change in the magnetic field detected by the magnetic field sensors to determine how to reposition the coil(s) to produce the intended magnetic field. For example, the coil(s) may have moved from a desired orientation to an undesired orientation. The coil positioning system may control the position of the coil(s) via the physical coupling to move the coil(s) back to the desired orientation, e.g., by moving the coil(s) in a direction opposite to which they were originally moved. In some implementations, the coil positioning system may move the coil(s) not back to their original position, but to any appropriate positon that produces a desired magnetic field distribution.

Controlling positioning of the coil(s) physically—e.g., by applying force to the coil(s) via a physical coupling—may have advantages over other methods of coil positioning. For example, physical positioning provides direct control over coil movement, which may enable more precise positioning of the coil than systems that control coil position without physically contacting the coil(s).

Figure 29:
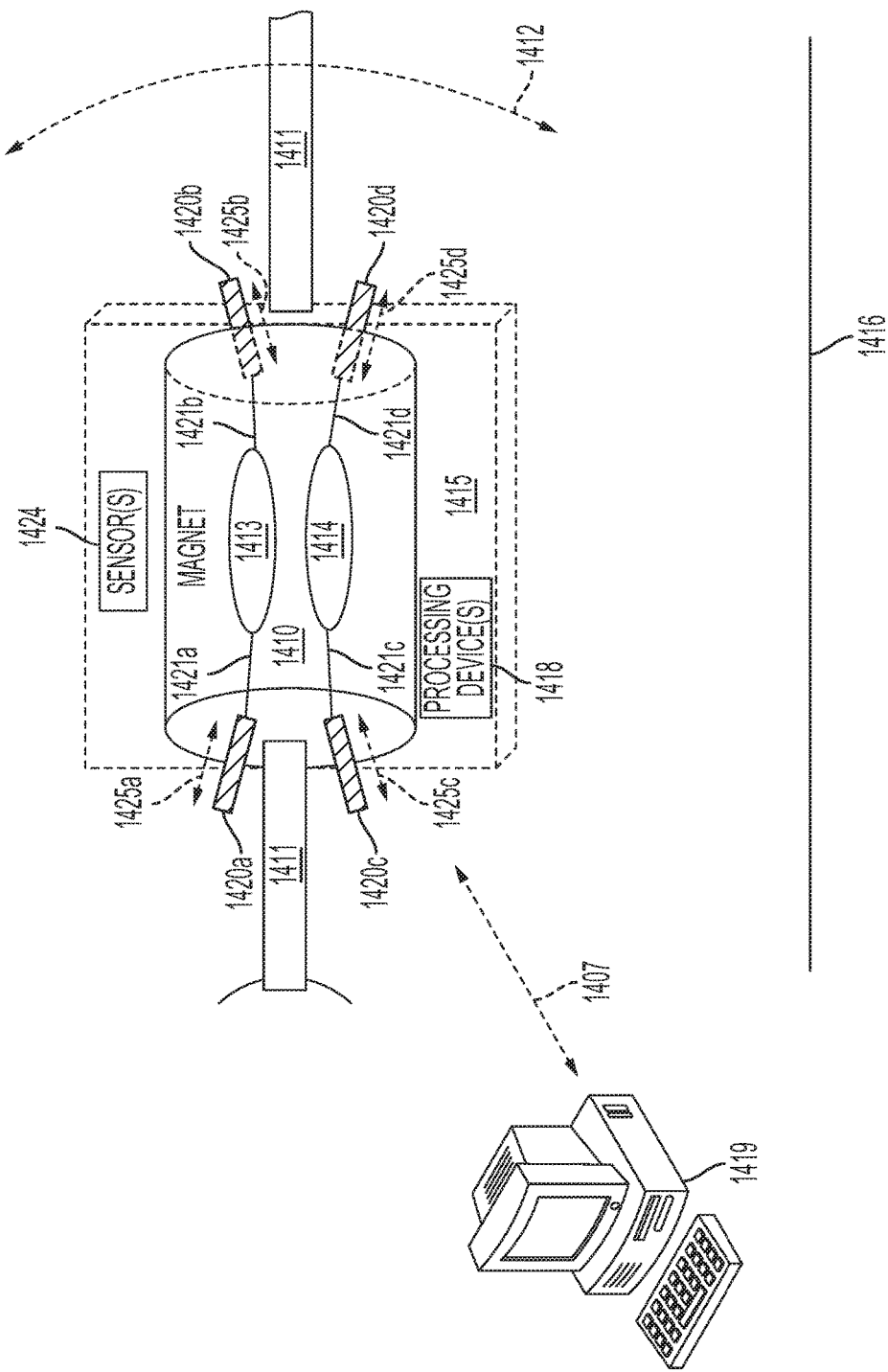
FIG. 29 is a block diagram showing an example of a coil positioning system installed on a moveable magnet.

The coil positioning systems described herein may be used in any appropriate context. FIG. 29 is a block diagram showing a magnet 1410 supported on a mount 1411 for rotation, e.g., in the directions of arrow 1412, relative to ground 1416. Only part of mount 1411 is depicted in FIG. 29. The rotation enabled by the mount may be a 360° rotation or less than a 360° rotation; in other words, a partial rotation. Examples of mounts may include, but are not limited to, a rotatable gantry, robotic arm(s), rotatable axles or shafts, tracks along which the accelerator may move, or other appropriate structures. Magnet 1410 may include coils 1413, 1414 that conduct current to generate a magnetic field. Although two coils are shown, in some implementations, the magnet may have a single coil or more than two coils. The coils may be superconducting or non-superconducting. In the case of superconducting coils, any appropriate superconducting material may be used. For example, the superconducting material may include, but is not limited to, one or more of the following materials, either alone or in combination: niobium-tin/triniobium-tin (Nb3Sn), niobium-titanium (NbTi), vanadium-gallium (V3Ga), bismuth strontium calcium copper oxide (BSCCO), yttrium barium copper oxide (YBCO), or magnesium diboride (MgB2). For non-superconducting coils, the material may be, or include, copper or any other appropriate conductor.

In the example of FIG. 29, magnet 1410 may include one or more pole pieces (e.g., magnetic yokes) that shape the magnetic field generated by the coils. In some implementations, the pole piece(s) may be omitted. In the example of FIG. 29, magnet 1410 includes a housing 1415 that holds magnet 1410 during movement, such as rotation relative to a reference point, such as ground 1416. Housing 1415 may be, or include, a vacuum enclosure, magnetic yoke(s), the pole piece(s), any appropriate combination(s) thereof, or any other appropriate structure alone or in combination with the vacuum enclosure, the magnetic yoke(s), or the pole piece(s). In implementations that include a housing, supports may hold (e.g., suspend) the magnet inside the housing. Any appropriate number of supports may be used. In this example, housing 1415 is depicted in dashed outline form to enable the magnet inside the housing to be viewed, and to indicate that the housing is exterior to the magnet. In this example, the housing substantially encloses the magnet; however, in other examples, the housing may be adjacent to the magnet, border the magnet, surround the magnet, or partly enclose the magnet. The housing may be made of a conductive or non-conductive material, and may incorporate magnetic and/or thermal shielding into its structure. In some implementations, the housing may be omitted altogether, and the magnet may be coupled directly to the mount 1411 instead of indirectly coupled via the housing.

Magnet 1410 may be a component of a larger system including, but not limited to, a medical system, such as a patient treatment system or an imaging system. In some implementations, the magnet may be part of a therapeutic radiation system, such as a particle (e.g., proton) therapy system, examples of which are described with respect to FIGS. 1 to 28. For example, magnet 1410 may be an accelerating magnet of a particle accelerator, as described herein. Magnet 1410 may be a bending magnet. For example, magnet 1410 may be configured to direct a particle beam towards, and across, an irradiation target, as is the case in a particle beam scanning system. Magnet 1410 may be a focusing magnet. For example, magnet 1410 may be configured to focus a particle beam prior to output. This listing of example magnet applications is illustrative and not exhaustive.

Forces (e.g., gravity) resulting from movement of the magnet including, but not limited to, a change in orientation of the magnet, may cause an undesired displacement of the coils. For example, the coils may be displaced relative to the housing or simply relative to an expected, target position of the coils. This displacement may affect the magnitude and/or the shape of the magnetic field produced by the magnet, thereby affecting operation of the system of which the magnet is part. For example, in the case of a particle therapy system, undesired displacement of the coils can affect the energy of the particles output by the particle accelerator, the targeting of a particle beam during scanning of a tumor, and/or the definition or integrity of the particle beam if focusing is not performed correctly.

Accordingly, magnet 1410 is equipped with an implementation of the coil positioning system described herein. In this example, the coil positioning system is computer-controlled; that is, the coil positioning system is controlled by one or more processing device(s) executing appropriate instructions (e.g., computer programs). In some implementations, the magnet, housing, or other connected structure includes one or more embedded processing devices 1418 that control operation of the coil positioning system either independently or in coordination with a computing system 1419. In some implementations, the magnet does not include on-board intelligence, and the coil positioning system is controlled by command and/or control signals 1407 provided by computing system 1419 directly to electronics that operate the coil positioning system. In this specification, reference to "a processing device" may include more than one processing device, and reference to "a computing system" or "a computer system" may include one or more processing devices.

In this example, the coil positioning system includes one or more actuators 1420a to 1420d that are mounted onto, or otherwise connected to, the magnet or associated structure (e.g., a magnet housing). In the example of FIG. 29, there are four actuators; however, as described herein, any appropriate number of actuators may be used. In some implementations, each actuator is configured to reproduce calibrated coil positions determined by testing in order to improve beam performance for at least some rotation angles. In some implementations, each actuator may be a servo-controlled actuator that is configured to actively maintain to a control parameter, such as beam direction or read-outs from a sensor used to measure a magnetic field produced by the coil that varies with coil position.

Each actuator is connected to a coil via a respective physical coupling 1421a to 1421d. Each physical coupling may be, or include, any appropriate physical structure or combination of physical structures that enables transfer of force between the actuator and the coils. Thus, the physical coupling between the actuator and the coils may be a direct physical connection, or may be a physical connection that includes one or more intervening components. Despite the presence of these intervening components, in some implementations, the physical coupling may be configured so that force can be directed from the actuator either towards, or away from, the coils to control movement, and thus positions, of the coils. Positioning and repositioning of the coils may be performed in real-time, or positioning of the coils may be performed after coil movement. In some examples, real-time control includes positioning and repositioning the coils incrementally to correct for unwanted coil movement while the coils are still moving.

In some implementations, a single actuator may be connected to multiple coils via respective physical couplings. For example, in some implementations, the single actuator may be configured to control selected one(s) of the multiple coils to which the single actuator is connected. In some implementations, the single actuator may be configured to control, concurrently, all coils to which the single actuator is connected.

In some implementations, each physical coupling includes one or more members connected at one end either directly or indirectly to the magnet coil and connected at another end either directly or indirectly to the actuator. The physical coupling may be a rigid coupling, a non-rigid coupling, or a semi-rigid coupling. A coupling that is rigid may include a coupling that has little or no elasticity even in the presence of weights on the order of tens of tons. A coupling that is semi-rigid may include a coupling that has elasticity in the presence of higher weights, e.g., on the order of tens of tons. A coupling that is non-rigid may include a coupling that has elasticity even at example weights less than those described.

A rigid coupling may enable control of coil position through application of force in a direction towards the coils, that is, by pushing the coils via the rigid coupling. A rigid coupling may also enable control of coil position to be implemented by applying force in a direction away from the coils, that is, by pulling the coils via the rigid coupling. In some cases, depending upon the weight of the coils and associated structure to be moved, a semi-rigid physical coupling may also be used to control coil position through application of force towards, or away from, the coils. A semi-rigid or non-rigid coupling may enable control of coil position to be implemented by applying force in a direction away from the coils, that is, by pulling the coils. In other words, tension on the coupling may be increased to pull the coils to force movement. Material(s) to implement a semi-rigid or non-rigid physical coupling will have sufficient tensile strength to withstand breakage under loads to which they are subjected. For example, in the case of a load measured in tens of tons (e.g., 30 tons), materials such as carbon fiber and fiberglass as described with respect to FIG. 5, may be used to implement a physical coupling under tensile stress. An example of part of a physical coupling is a strap 402, 404, 406 described with respect to FIG. 5. This strap may be used in the physical couplings of FIG. 29; however, other configurations for the physical couplings may also be used in the system of FIG. 29 in addition to, or instead of, that strap.

FIG. 29 shows four actuators mounted proximate to magnet 1415 to control positioning of coils 1413, 1414—two actuators per coil. In this regard, in some implementations, the actuators may be mounted on components of the magnet, and in some implementations the actuators may be mounted elsewhere (e.g., to the housing) but with physical couplings to the coils. Although four actuators are shown in FIG. 29, any appropriate number of actuators may be used. For example, there may be only one actuator or there may be two or more actuators. In some implementations, as described below, there may be four actuators on each side of a magnet. For example, as described herein, there may be eight actuators arranged symmetrically—four on each side of the housing of a magnet. In this regard, in some implementations, the actuators may be arranged symmetrically relative to the magnet to balance the load on each actuator evenly and/or to provide more flexibility in determining how to position the coils. In an example, one actuator may be located on each magnet pole face, two actuators may be located on opposite sides of a single magnet pole face, and so forth. The number of actuators used, and their locations, may be dependent on a number of factors, such as the size of the load (the magnet), anticipated direction of movement, and so forth. In operation, any one, two, or more of the actuators may be controllable to act in concert to move the coils in order to correct unwanted coil displacement.

In some implementations, magnet 1415 includes a support structure to hold coils 1413, 1414. Examples of such a support structure is, or includes, a reverse bobbin, such as those shown in FIGS. 16 and 24; however, other types of support structures may be used. In this example, the physical coupling to coils 1413, 1414 may include support structure/reverse bobbin, one or more members such as strap the straps of FIG. 5, and actuators 1420a to 1420d. In some implementations, the physical coupling to each coil may include the support structure/reverse bobbin and an actuator, but not the strap. In some implementations, the physical coupling to each coil may include a strap and an actuator, but not the support structure/reverse bobbin. Actuators 1420a to 1420d are controllable, either individually or two or more in combination, to move the coils by imparting force in either direction of respective arrows 1425a to 1425d. Not all actuators need operate to move the magnet coils. For example, any one, two, or other appropriate subset may impart force, while the other actuators remain inactive. As described herein, the actuators may be computer-controlled based on outputs of one or more sensors 1424 to correct for displacement of the coils relative to a reference caused by movement (e.g., rotation) of the magnet.

Figure 34:
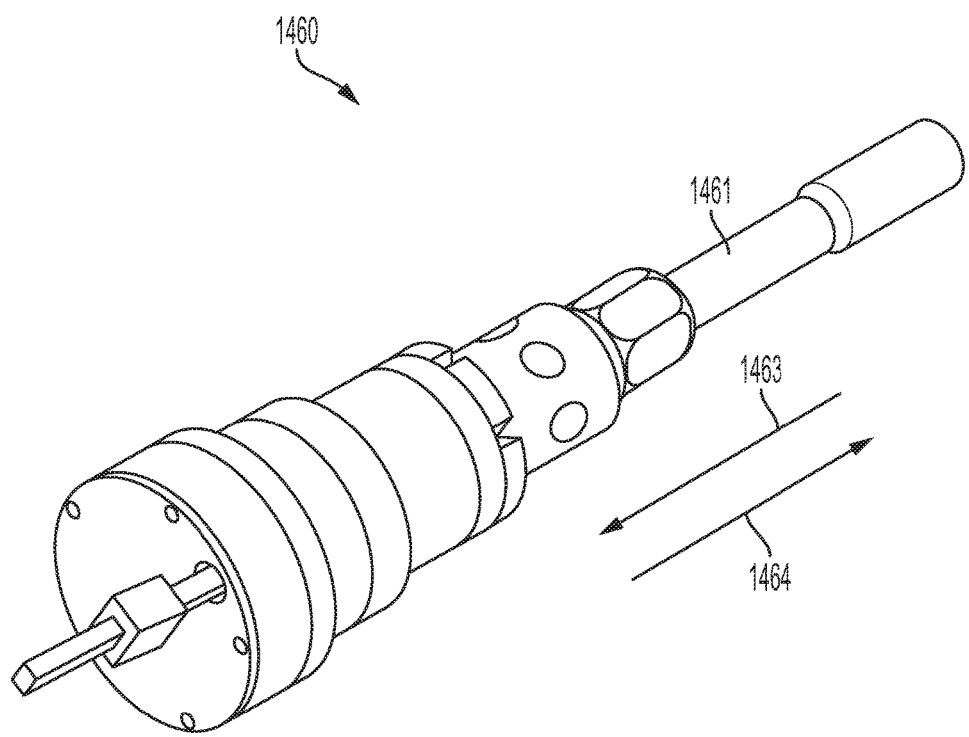
FIG. 34 is a perspective view of an example coil positioning actuator.

FIGS. 34 and 35 show an example of an actuator 1460 that may be used in the coil positioning system. FIG. 34 shows a perspective view of the actuator; FIG. 35A shows a side view of the actuator; and FIG. 35B shows a cut-away, side view of the actuator of FIG. 35A along lines A-A. As explained, actuator 1460 connects to, and is part of, a physical coupling (e.g., 1421*a*, 1421*b*, 1421*c*, or 1421*d* of FIG. 29) to a coil (e.g., coil 1413 or 1414 of FIG. 29). As such, actuator 1460 is controllable to reposition one or more of the coils physically, rather than through indirect means like magnetic field control. In this example, actuator 1460 includes a body 1461 and a high-gear ratio actuator called a differential screw 1462 that is included within, and that moves through and relative to, a shaft that passes through the body.

In the example of FIGS. 34 and 35, body 1461 of actuator 1460 may mount to the magnet or a magnet housing. For example, the body and housing may be welded together or mated in other any other appropriate manner. In some implementations, the housing is, or includes, a vacuum enclosure, which maintains the magnet in a vacuum environment. In examples like this, the connection between the actuator and the magnet housing (the vacuum enclosure) is air-tight.

A hole (not shown) through housing aligns substantially with differential screw 1462 and enables the actuator to connect to, and thus become part of, the physical coupling to the coils. In this example, differential screw 1462 connects to members that connect to a support structure holding the coils. By controlling movement of the differential screw through the shaft in body 1461, the physical coupling to the corresponding coil makes it possible to move, and position/reposition, the coil. In this example, differential screw 1462 is movable in the direction of arrow 1463, thereby increasing the tension on the physical coupling to the coil in order to implement movement of the coils. Differential screw 1462 may move in the direction of arrow 1464 to release tension on the physical coupling to the coil in order to enable movement of the coils in a different direction (e.g., to allow another actuator to control movement). In some implementations, differential screw 1462 may move in the direction or arrow 1464 effectively to push the coils.

In examples where differential screw 1462 applies tensile load to the physical coupling to move the coils, body 1461 of the actuator is under compression against the structure to which it is mounted (e.g., a vacuum enclosure housing). More specifically, in an example operation, differential screw 1462 moves in direction 1463, increasing tension on the physical coupling (e.g., by pulling a strap of FIG. 5 or other appropriate structure) in order to move the support structure (e.g., the reverse bobbin of FIGS. 16 and 24) and, thus, move the coils supported thereby. This pulling action forces the actuator body 1461 against the housing. Accordingly, the housing is typically made of metal or other material that is sufficient to resist significant force without damage. A motor (not shown) may be included within, or connected to, the body of the coil positioning actuator 1460 to drive movement of the differential screw towards and away from the magnet. The motor (not shown) is configured to drive the screw in response to commands from an embedded or external processing device. Although four actuators are shown in FIG. 29, any appropriate number of actuators may be used to position the coils, and the actuators may be arranged at any appropriate locations on the housing.

The coil positioning system may be incorporated, as appropriate, into the example particle therapy systems described with respect to FIGS. 1 to 28. FIGS. 30 to 33 and 36 to 45 also depict components of example particle therapy systems that may include implementations of the coil positioning system.

An example of a particle therapy system that may include the coil positioning system is a proton or ion therapy system. The example particle therapy system includes a particle accelerator—in this example, a synchrocyclotron—mounted on a movable device. In some examples, the movable device is a gantry that enables the accelerator to be rotated at least partially, and in some cases completely, around a patient position to allow a particle beam from the synchrocyclotron to hit any arbitrary target in the patient. Any appropriate device, including a gantry, may be used to hold the particle accelerator and to move the particle accelerator in a rotational, translational, and/or pivotal motion relative to the patient. For example, the particle accelerator may be mounted to one or more tracks to enable motion relative to the patient. In another example, the particle accelerator may be mounted to one or more robotic arms to enable motion relative to the patient. Any one or more of rotational, translational, and/or pivotal motion may result in unwanted coil movement that can be corrected by the coil positioning system.

Notably, the particle therapy system is not limited to use with a gantry, to use with a rotational gantry, or to use with the example gantry configurations described herein. In some implementations, the example synchrocyclotron has a high magnetic field superconducting electromagnetic structure. In general, a superconductor is an element or metallic alloy which, when cooled below a threshold temperature, loses most, if not all, electrical resistance. As a result, current flows through the superconductor substantially unimpeded. Superconducting coils, therefore, are capable of conducting much larger currents in their superconducting state than are ordinary wires of the same size. Because of the high current that superconducting coils are capable of conducting, magnets that employ superconducting coils are capable of generating high magnetic (B) fields for particle acceleration. Furthermore, because the bend radius of a charged particle having a given kinetic energy is reduced in direct proportion to an increase in the magnetic field applied to the charged particle, a high magnetic field superconducting electromagnetic structure enables the synchrocyclotron to be made compact, e.g., relatively small and light. More specifically, the higher the magnetic field used, the tighter the particle turn radius may be, thereby allowing for a larger numbers of turns to be made within a relatively small volume (that is, relative to larger, non-superconducting synchrocyclotrons). As a result, a desired particle energy—which increases with an increase in the number of turns—can be achieved using a synchrocyclotron having a relatively small size and weight. In some implementations, the synchrocyclotron is configured to produce a particle beam having sufficient energy to reach any arbitrary target within the patient from any appropriate position in the proton center relative to the patient. Because of the tight turn radius, a compact accelerator can be susceptible to small errors in magnetic field, which can be produced, e.g., by sub-millimeter coil movements.

By way of example, in some implementations, a maximum magnetic field produced in the acceleration cavity of the synchrocyclotron (e.g., at the center of the cavity) may be between 4 Tesla (T) and 20 T. In some implementations, the synchrocyclotron weighs less than 40 Tons. For example, the synchrocyclotron may have a weight that is within a range from 5 tons to 30 tons. In some implementations, the synchrocyclotron occupies a volume of less than 4.5 cubic meters. For example, the synchrocyclotron may occupy a volume in a range from 0.7 cubic meters to 4.5 cubic meters. In some implementations, the synchrocyclotron produces a proton or ion beam having an energy level of at least 150 MeV. For example, the synchrocyclotron may produce a proton or ion beam having an output energy level that is within a range from 150 MeV to 300 MeV, e.g., 230 MeV. Different implementations of the synchrocyclotron may have different values or combinations of values for size, volume, and energy level, including values not stated. Advantageously, the compact nature of the synchrocyclotron described herein allows the treatment to be performed in one room, e.g., in a proton center.

Figure 36:
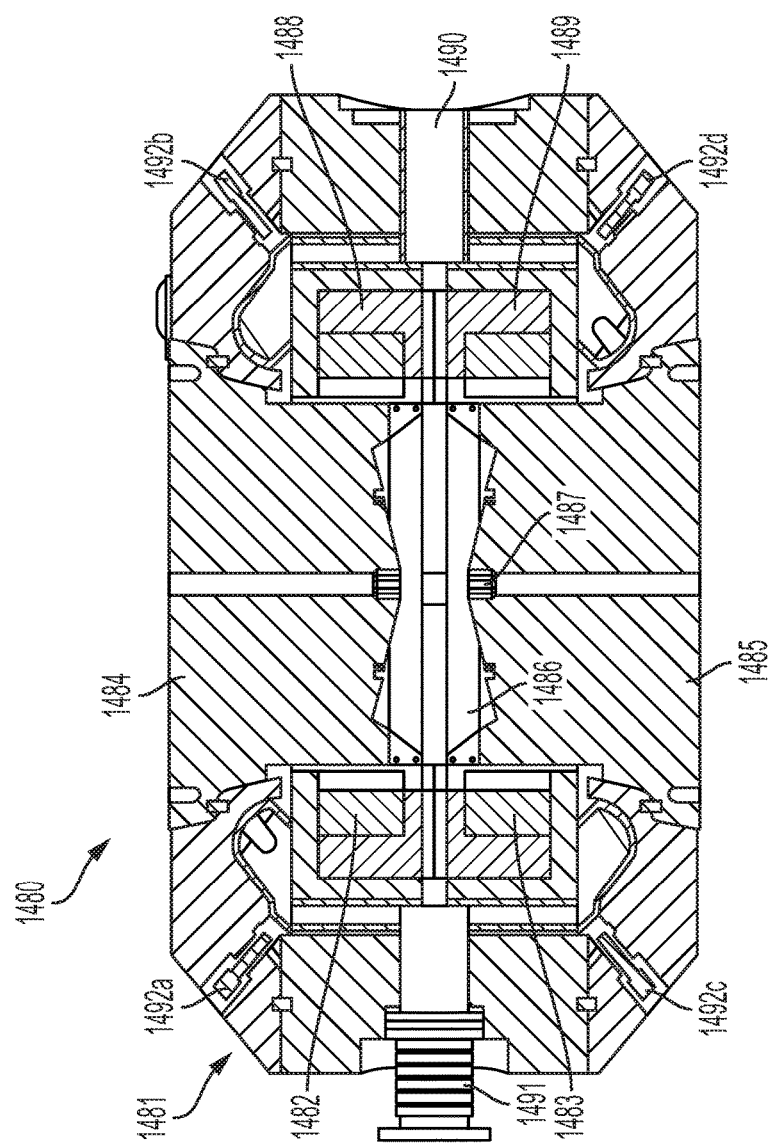
FIG. 36 is a cut-away, side view of components of an example synchrocyclotron that may be used in a particle therapy system, and that may incorporate the coil positioning system described herein.

FIG. 36 shows a cross-section of components 1480 of an example superconducting synchrocyclotron that may be used in a particle therapy system. For example components 1480 may be substituted for corresponding components in the systems described with respect to FIGS. 1 to 28. In this example, components 1480 include a superconducting magnet 1481. The superconducting magnet includes superconducting coils 1482 and 1483. Each superconducting coil 1482 and 1483 is mounted within a reverse bobbin 1488, 1489 which is the type of support structure that is described herein.

The superconducting coils may be formed, e.g., of multiple superconducting strands (e.g., four strands or six strands) wound around a center strand which may itself be superconducting or non-superconducting (e.g., copper). Each of the superconducting coils 1482, 1483 is for conducting a current that generates a magnetic field (B). The resulting magnetic field is shaped by magnetic yokes 1484, 1485. In an example, a cryostat uses liquid helium (He) to maintain each coil at superconducting temperatures, e.g., around 4° Kelvin (K). The magnetic yokes 1484, 1485 (or smaller magnetic pole pieces) define the shape of a cavity 1486 in which particles are accelerated. In some implementations, magnetic shims (not shown) may pass through the magnetic yokes or pole pieces to change the shape and/or magnitude of the magnetic field in the cavity. Changes to the locations of the coils within the cryostat can affect the field shape, and thus the resulting particle beam.

In this example, the superconducting magnet includes one or more support structures, which include reverse bobbins 1488, 1489 that include coil chambers to hold superconducting coils 1482, 1483 (see also FIGS. 16 and 24). Each coil chamber holds a pre-wound superconducting coil. In some implementations, a superconducting coil is not fixed within a reverse bobbin, but rather is simply placed, relatively free-floating, in a corresponding coil chamber. During operation of the superconducting magnet, a hoop force may cause the superconducting coil to expand outwardly, thereby forcing the superconducting coil against the outer inside wall of the coil chamber. This hoop force can keep the coil in place in the reverse bobbin during movement. However, a free-floating mounting can make the coil more susceptible to unwanted movement during accelerator rotation. The assembly that includes the reverse bobbins and the superconducting coil is part of a structure referred to as a cold mass, since at least part of the assembly is maintained at low, e.g., superconducting (4° K), temperatures during operation. The cold mass may be suspended inside the vacuum enclosure by support straps. These support straps may be under constant tension and, as described herein, may be part of a physical coupling (which may also include the reverse bobbin in some implementations) between the coils and the coil positioning actuators that are part of the coil positioning system.

Other features of magnet assembly shown in FIG. 36 include an extraction channel 1490 and an RF (radio frequency) port 1491. Extraction channel 1490 is a pathway through which a particle beam passes. RF port 1491 is a pathway through which RF energy is imparted to the acceleration cavity. In this example, support straps 1492a to 1492d of FIG. 36 may be part of the magnet assembly, and are used to connect the cold mass assembly to the vacuum enclosure, as described in more detail below.

In some implementations, operation of the magnet is particularly susceptible to coil movement relative to the radial direction of RF port 1491. Movement of the coil relative to this direction can affect the magnetic field produced by the coil vis-à-vis the regenerator, as described below.

Figure 37:
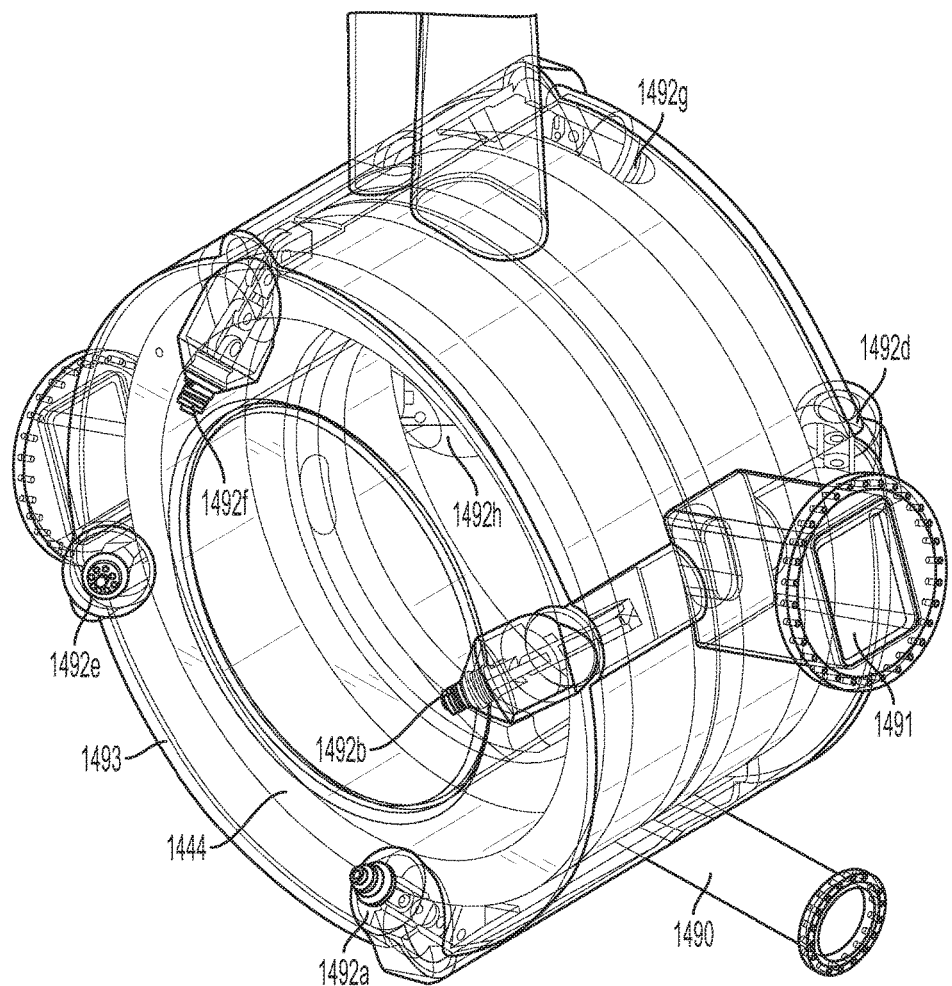
FIG. 37 is a perspective view of components of an example synchrocyclotron, including a cold mass and a vacuum enclosure, with the vacuum enclosure shown in outline to enable the cold mass to be seen.
Figure 38:
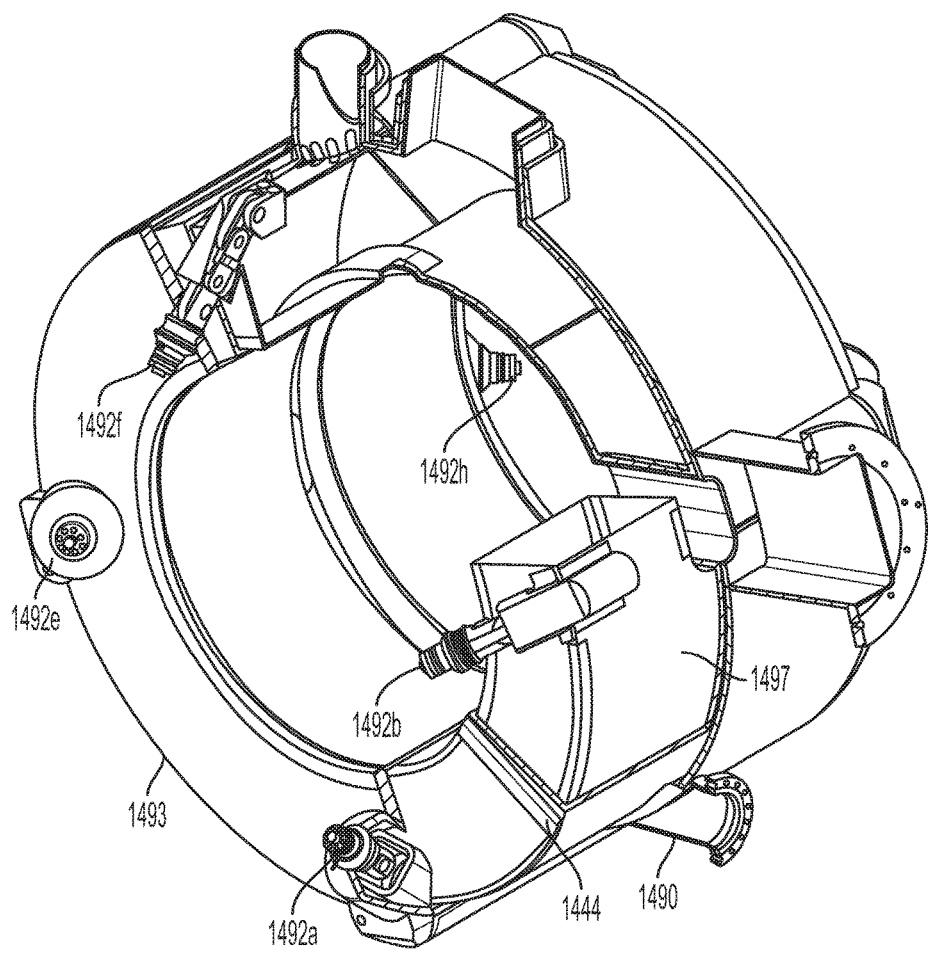
FIG. 38. is a cut-away, perspective view of components of an example synchrocyclotron, including part of the vacuum enclosure cut-away to reveal the cold mass and shielding.
Figure 39:
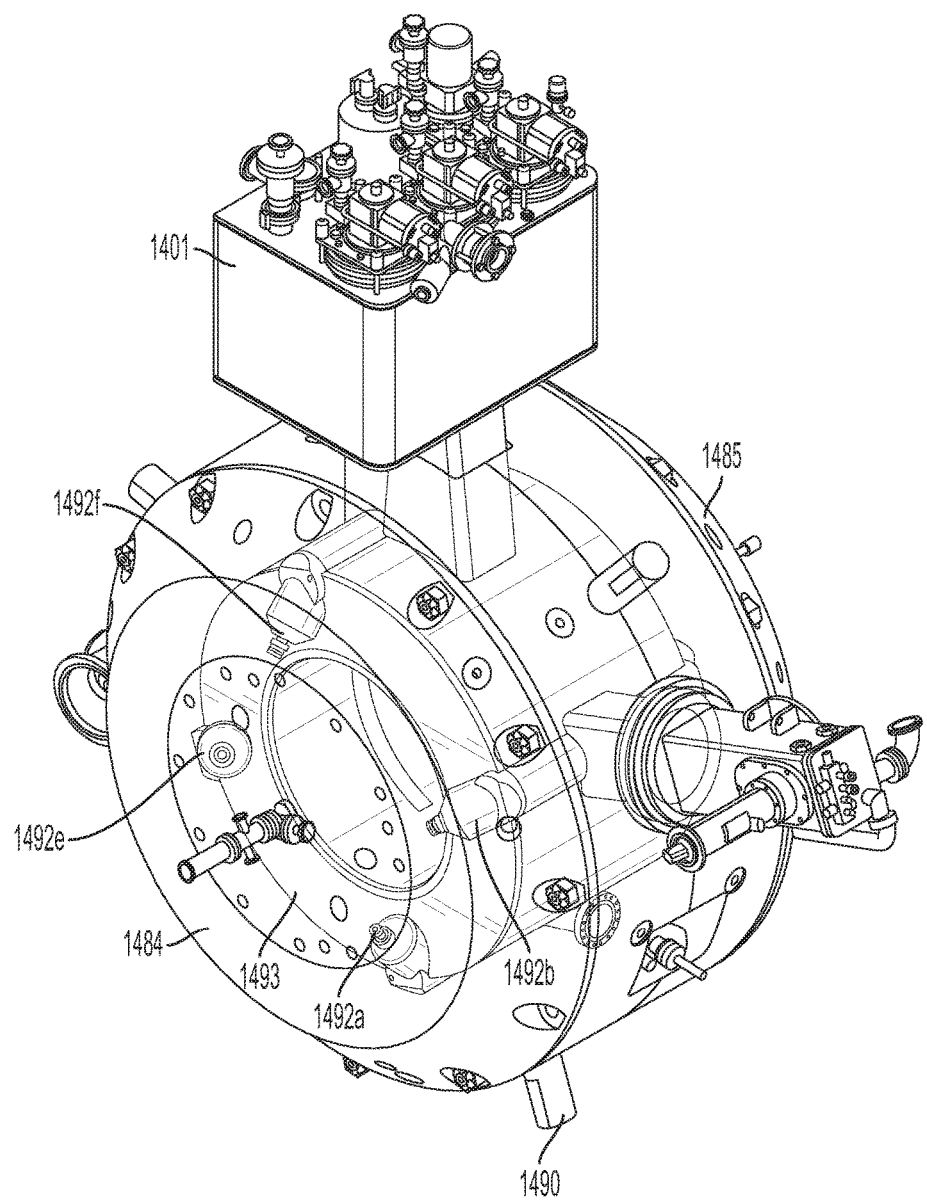
FIG. 39 is a perspective view of components of an example synchrocyclotron, including the vacuum enclosure, magnetic yokes, and a cooling turret, with the magnet yokes shown in outline to enable the vacuum enclosure to be seen.

Referring FIGS. 37, 38, and 39, a superconducting magnet assembly 1444, e.g., the cold mass, is encased in a vacuum enclosure 1493. FIG. 37 shows vacuum enclosure 1493 in outline form enclosing the superconducting magnet assembly. FIG. 38 shows vacuum enclosure 1493 cut-away to expose a part of the superconducting magnet assembly. A thermal shield 1497 around assembly 1444 is also shown. Vacuum enclosure 1493 includes RF port 1491 for introducing frequency-swept RF voltage into the acceleration cavity, and an extraction channel 1490 for outputting the particle beam. The magnetic yokes 1484, 1485, which are shown in outline form in FIG. 39, and which are described with respect to FIG. 36, encase the vacuum enclosure 1493 of FIGS. 37 and 38. For example, there may be a physical connection holding the vacuum enclosure in the yokes. In this example, the superconducting magnet assembly 1444, including the cold mass, is mounted to the vacuum enclosure via eight support straps 1492a, 1492b, 1492c, 1492d, 1492e, 1492f, 1492g, and 1492h although any appropriate number of support straps may be used. Examples of straps are described herein.

Figure 40:
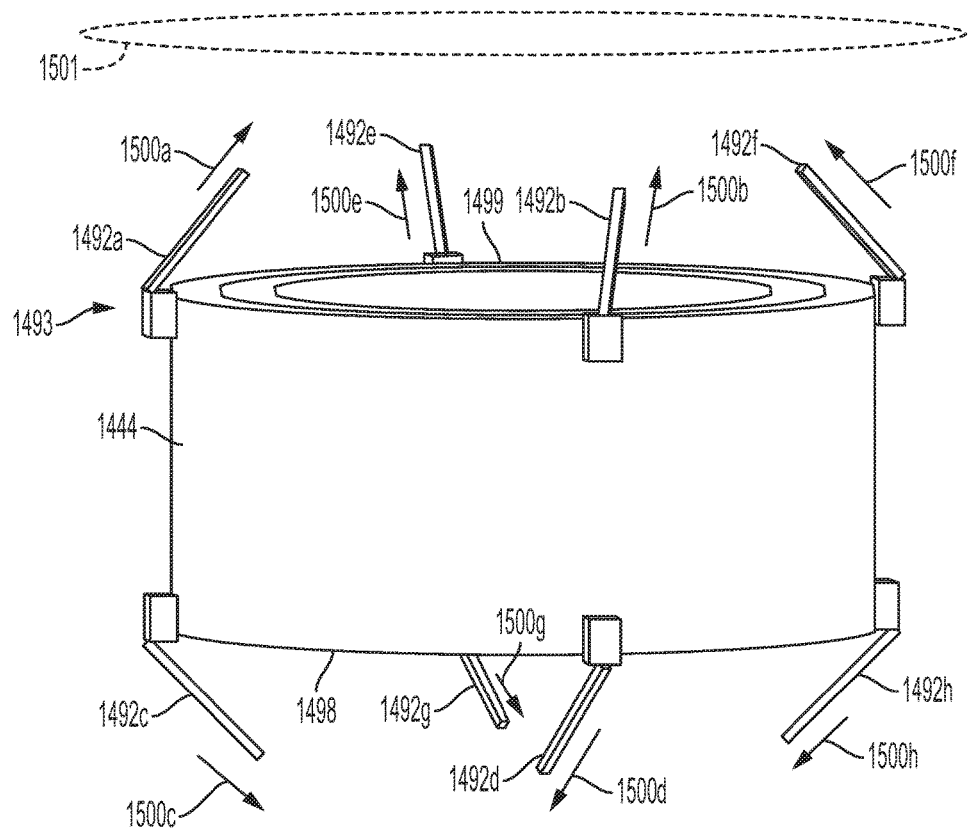
FIG. 40 is a conceptual, perspective view of an example cold mass, showing straps for suspension from a vacuum enclosure.

FIG. 40 shows these straps 1492a to 1492h connected to the cold mass (e.g., 1444). In these examples, there are eight support straps 1492a to 1492h. Not all straps can be seen in each of FIGS. 36 to 39. In these examples, there are four straps on each side 1498, 1499 of the assembly. The straps are under constant outward tension to support the cold mass from the vacuum enclosure. Effectively, the cold mass is suspended within the vacuum enclosure by the straps. In this context, example outward tension of the support straps (that is, away from the cold mass) is represented in FIG. 40 by force vectors 1500a to 1500h from the cold mass directed towards the vacuum enclosure.

Although the straps are under tension to pull the cold mass, in the examples of FIGS. 37 to 40 the straps pull the cold mass inward relative to an exterior perimeter 1501 of the vacuum enclosure 1493 (see FIG. 40). By maintaining inward tension on the straps, e.g., by pulling the straps in the directions of arrows 1500a to 1500h, inclusion of the straps may not significantly increase the overall size of the accelerator. In other implementations (not shown), the straps may pull the cold mass outward relative to the exterior perimeter 1501 of the vacuum enclosure.

As described, there may be multiple straps (e.g., eight straps) that support a single cold mass within a single vacuum enclosure. As described in more detail below, a coil positioning actuator of the type shown in FIGS. 34 and 35 may be connected to one or more of the straps, and may be used to control tension on the strap in order to move the cold mass, and thus the magnet coils, relative to the vacuum enclosure. This may be done to correct or compensate for unwanted movement of the cold mass, and thus the magnet coils, during movement of the accelerator as may occur during treatment of a patient. In some implementations, the vacuum enclosure is connected to, and is inside, the yokes; accordingly, this movement of the cold mass, and thus the magnetic coils, may also constitute movement of the magnet coils with respect to the yokes.

In some implementations, a coil positioning actuator of the type shown in FIGS. 34 and 35 may be connected to one of more of straps 402, 404, 406 of the type shown in FIG. 5, and may be used to control tension on the strap(s) in order to move the cold mass, and thus the magnet coils, for reasons described herein.

Some or all of the multiple straps supporting the cold mass within the vacuum enclosure may have configuration(s) different than those described herein. For example, the support straps may include a single element that acts as the physical coupling between the cold mass and the vacuum enclosure. In general, any appropriate physical coupling may be used to support the cold mass within the vacuum enclosure, and may be used with a coil positioning actuator of the type described herein.

Figure 41:
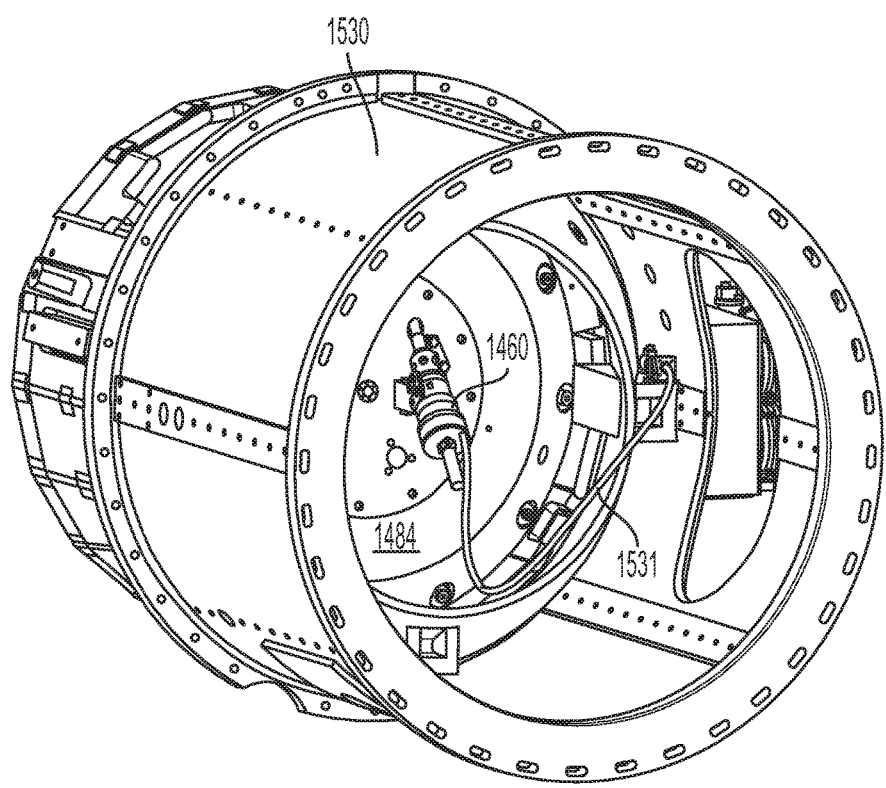
FIG. 41 is a perspective view of part of a particle accelerator, which shows a magnetic yoke and an example coil positioning actuator connected to, and through, the magnetic yoke.

FIG. 41 shows part of a particle accelerator 1530 (e.g., a synchrocyclotron) of a type described herein. In this example, a magnetic yoke, an example which is magnetic yoke 1484, houses the vacuum enclosure. A coil positioning actuator 1460 connects, through a hole in yoke 1484, to a strap (not shown) connected to the vacuum enclosure. The coil positioning actuator may be of the type shown in FIGS. 34 and 35. Referring to those figures, in this example, differential screw 1462 passes through, and into, the structure of a strap. For example, structure of the strap have an interior shaft that is threaded and that, accepts, and mates/connects to, the differential screw of the coil positioning actuator. Movement of the differential screw within the shaft of structure of the strap causes the strap to move which, in turn, causes the cold mass to move which, in turn, causes a coil supported by the cold mass to move. For example, movement of the differential screw within the shaft of structure of the strap causes the strap to become more or less tense, depending on how the differential screw is actuated.

In this regard, the strap is maintained under tension in order to support the cold mass from the vacuum enclosure. The differential screw may be actuated (e.g., in response to instructions from a processing device) to increase this tension and thereby move the coils in a first direction to a desired location. If the strap is already under increased tension by the differential screw, the differential screw may be actuated to decrease the tension and thereby facilitate or enable movement of the coils in a second direction, e.g., that is opposite to the first direction. Notably, in this example, the coil positioning actuators are not used to decrease the tension in a strap below the natural tension needed to keep the cold mass supported within the vacuum enclosure. Any one, two, three, or more coil positioning actuators may be controlled to act in concert to position the cold mass, and thus the superconducting coils, to an appropriate position. For example, the coil positioning actuators may be used to place the coils in their original position relative to some reference.

As explained, the coil positioning actuators may be computer controlled, and operable in real-time to correct coil movement incrementally, or operable following coil movement to reposition the coil to an appropriate position to achieve an intended magnetic field distribution, e.g., to the coil's predefined, intended position. FIG. 41 shows a wired connection 1531 to transmit control signals to the coil positioning actuator to control coil movement as described herein. Alternatively, wireless signals may be used to control the coil positioning actuators.

Referring back to FIG. 36, in some implementations, the particle accelerator includes a particle source 1487 (e.g., a Penning Ion Gauge—PIG source) to provide an ionized plasma column to the cavity 1486. The PIG source may be of the type described above. For example, hydrogen gas, or a combination of hydrogen gas and a noble gas, is ionized to produce the plasma column. A voltage source provides a varying radio frequency (RF) voltage to cavity 1486 to accelerate pulses of particles from the plasma column within the cavity. The magnetic field in the cavity is shaped to cause particles to move orbitally within the cavity. The coil positioning system may be used to ensure that magnetic field within the cavity maintains the proper shape for all accelerator orientations. In some implementations, the maximum magnetic field produced by the superconducting coils may be within the range of 4 Tesla (T) to 20 T, as explained herein. The example synchrocyclotron employs a magnetic field that is uniform in rotation angle and falls off in strength with increasing radius. In some implementations, such a field shape can be achieved regardless of the magnitude of the magnetic field.

As noted, in an example, the particle accelerator is a synchrocyclotron. Accordingly, the RF voltage is swept across a range of frequencies to account for relativistic effects on the particles (e.g., increasing particle mass) when accelerating particles within the acceleration cavity. The magnetic field produced by running current through the superconducting coils, together with the shape of the cavity, causes particles accelerated from the plasma column to accelerate orbitally within the cavity and to increase in energy with an increasing number of turns.

In the example synchrocyclotron, a magnetic field regenerator (example of which are described with respect to FIGS. 15, 17, and 19 to 21) is positioned near the outside of the cavity (e.g., at an interior edge thereof) to adjust the existing magnetic field inside the cavity to thereby change locations, such as the pitch and angle, of successive orbits of the particles accelerated from the plasma column so that, eventually, the particles output to an extraction channel that passes through the cryostat. The regenerator may increase the magnetic field at a point in the cavity (e.g., it may produce a magnetic field "bump" of about 2 Tesla or so at an area of the cavity), thereby causing each successive orbit of particles at that point to proceed outwardly toward the entry point of an extraction channel until the particles reach the extraction channel. The extraction channel receives, from the cavity, particles that have been accelerated within the cavity, and outputs the received particles from the cavity in a pulsed particle beam. The extraction channel may contain magnets and other structures to direct the particle beam out of the particle accelerator and towards a scanning or scattering system. The coil positioning system described herein may be used to reposition magnets and other structures of the extraction channel following magnet movement.

In some implementations, coil movement relative to the regenerator, e.g., in a radial direction, can have a particularly deleterious effect on operation of the accelerator. For example, movement of the coils towards or away from the regenerator can change the magnitude of the magnetic field at locations proximate to the regenerator. This change in magnetic field can affect the shape of the particle orbits at those locations and can affect the required magnetic field bump needed to direct those orbits to the extraction channel. That is, the regenerator may be calibrated based on an expected magnetic field. However, if the magnetic field at or near the regenerator is different than expected, the magnetic field produced by the regenerator may not be enough, or may be too strong, which can cause particles not to be directed as expected into the extraction channel. These types of errors can cause the output particle beam to have the wrong energy. The example coil positioning system described herein may be used with the particle therapy system to correct for displacement of the accelerator coils including, but not limited to, correcting displacement of the accelerating coils relative to the regenerator. Examples of regenerators that the coil positioning system may be used with are described in U.S. Patent Publication No. 2014/0094640 entitled "Magnetic Field Regenerator", the contents of which are incorporated herein by reference.

As noted, the superconducting coils (called the main coils) can produce relatively high magnetic fields. In an example implementation, the maximum magnetic field generated by a main coil (e.g., at the center of the acceleration cavity) may be within a range of 4 T to 20 T or more. For example, the superconducting coils may be used in generating magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, the superconducting coils may be used in generating magnetic fields that are outside the range of 4 T to 20 T or that are within the range of 4 T to 20 T but that are not specifically listed herein.

Figure 4:
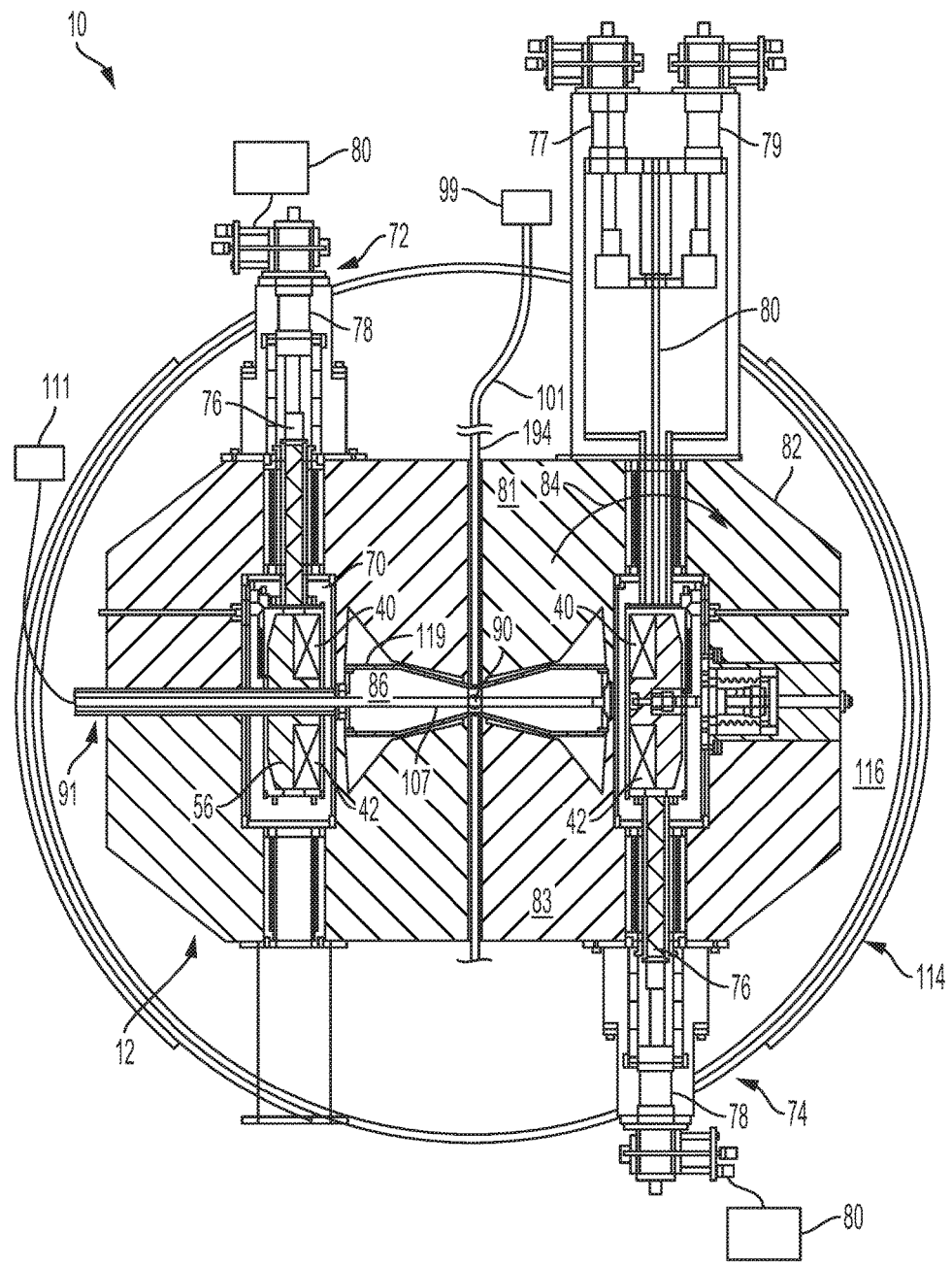

In some implementations, such as the implementations shown in FIGS. 3, 4, and 36, the relatively large ferromagnetic magnetic yokes act as returns for stray magnetic fields produced by the superconducting coils. In some systems, a magnetic shield (not shown) surrounds the yokes. The return yokes and the shield together act to reduce stray magnetic fields, thereby reducing the possibility that stray magnetic fields will adversely affect the operation of the particle accelerator.

In some implementations, the return yokes and shield may be replaced by, or augmented by, an active return system. An example active return system includes one or more active return coils that conduct current in a direction opposite to current through the main superconducting coils. In some example implementations, there is an active return coil for each superconducting main coil, e.g., two active return coils—one for each main superconducting coil. Each active return coil may also be a superconducting coil that surrounds the outside of a corresponding main superconducting coil concentrically. An example of an active return system that may be used is described in U.S. Pat. No. 8,791,656 entitled "Active Return System", the contents of which are incorporated herein by reference.

In an active return system, current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to reduce at least some of the relatively strong stray magnetic field resulting from a corresponding main coil. If the active return coils move unexpectedly during movement of the accelerator, the magnetic field generated thereby may not be as effective at reducing or dissipating fields produced by the main coils. The example coil positioning system may be used with a particle therapy system having an active return system to correct for displacement of active return coils.

At or near the output of the extraction channel of the particle accelerator, there may be one or more beam shaping elements, such as a scanning system and/or a scattering system. A scanning system and a scattering system are examples of beam spreaders. Components of these systems may be mounted on, or otherwise attached to, a nozzle for positioning relatively close to the patient during treatment. In some implementations, however, components may be mounted closer to (e.g., on) the accelerator or the gantry itself (e.g., mounted to the gantry in the absence of an accelerator mounted there). The gantry is referred to as an outer gantry, since some implementations include an inner gantry that tracks movement of the outer gantry and that includes a nozzle for delivering the beam.

Figure 42:
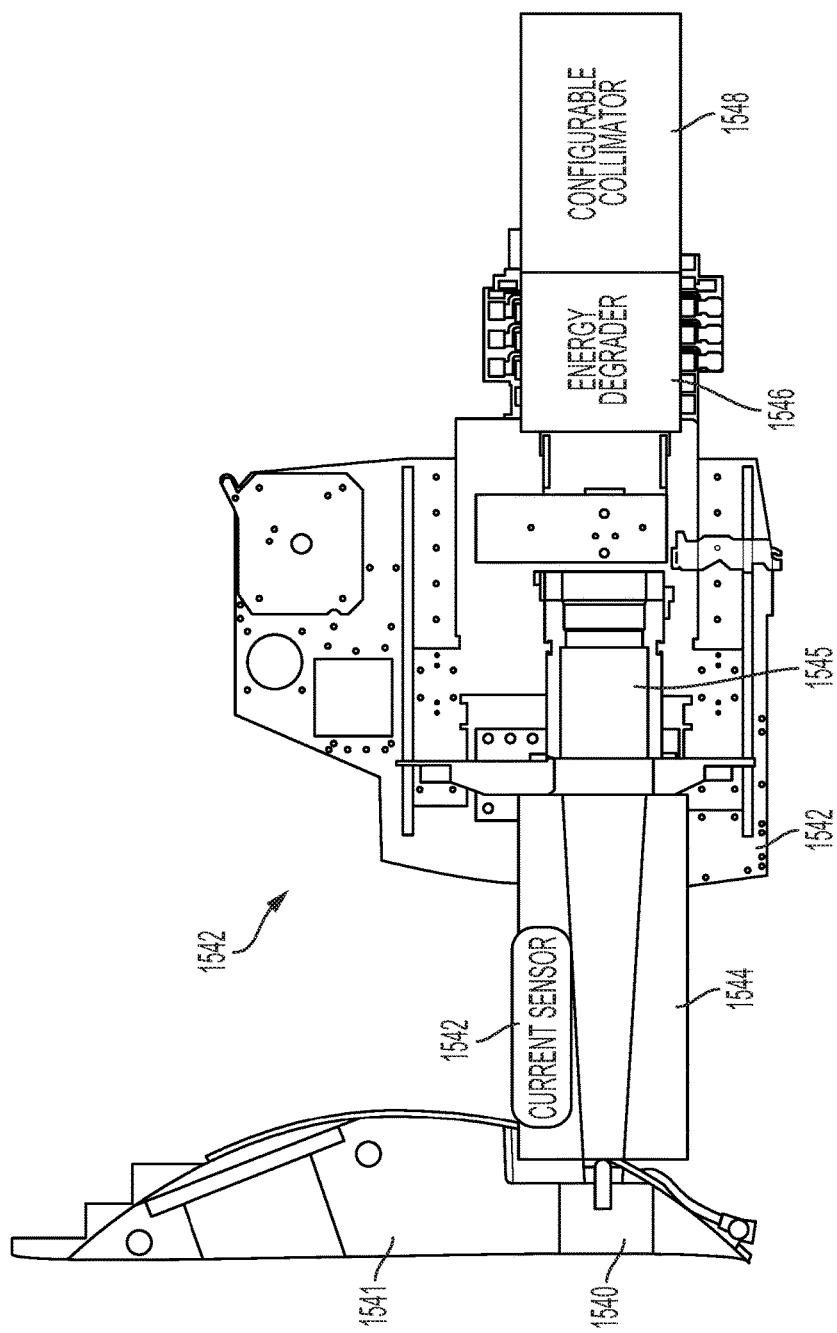
FIG. 42 is a side view of example components that may be used to implement scanning in a particle therapy system.
Figure 43:
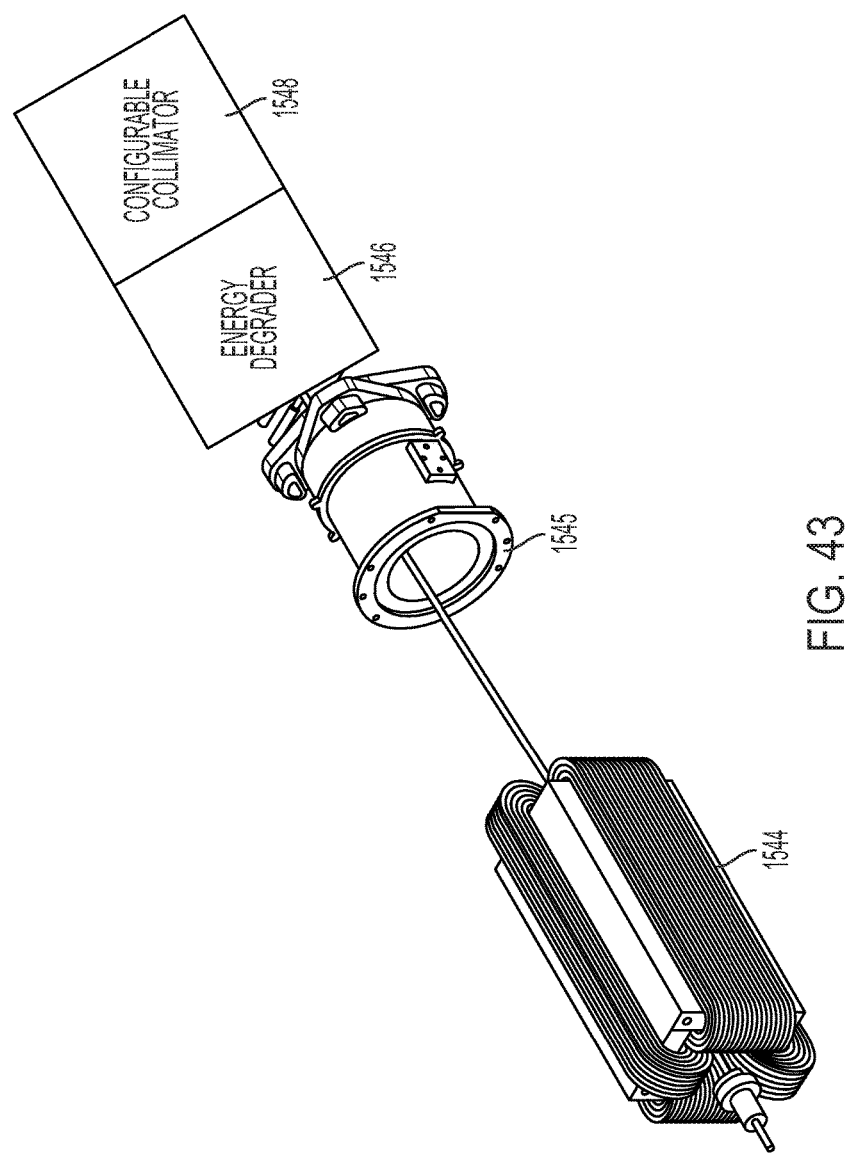
FIG. 43 is a perspective view of the example components that may be used to implement scanning in the particle therapy system.

Referring to FIG. 42, in an example implementation, at the output of extraction channel 1540 of synchrocyclotron 1541 (which may have a configuration as described herein— see, e.g., FIGS. 3, 4, 36) are example scanning components 1542 that may be used to scan the particle beam across all or part of an irradiation target. FIG. 43 also shows examples of the components of FIG. 42. These include, but are not limited to, a scanning magnet(s) 1544, an ion chamber 1545, an energy degrader 1546, and a configurable collimator 1548.

In an example operation, scanning magnet 1544 is controllable in two dimensions (e.g., Cartesian XY dimensions) to position the particle beam in those two dimensions, and to move the particle beam across at least a part (e.g., a cross-section) of an irradiation target. Ion chamber 1545 detects the dosage of the beam and feeds-back that information to a control system to adjust beam movement. Energy degrader 1546 is controllable to move material (e.g., one or more individual plates) into, and out of, the path of the particle beam to change the energy of the particle beam and therefore the depth to which the particle beam will penetrate the irradiation target. Configurable collimator 1548 is controllable to trim the particle beam prior to the particle beam reaching an irradiation target.

Figure 45:
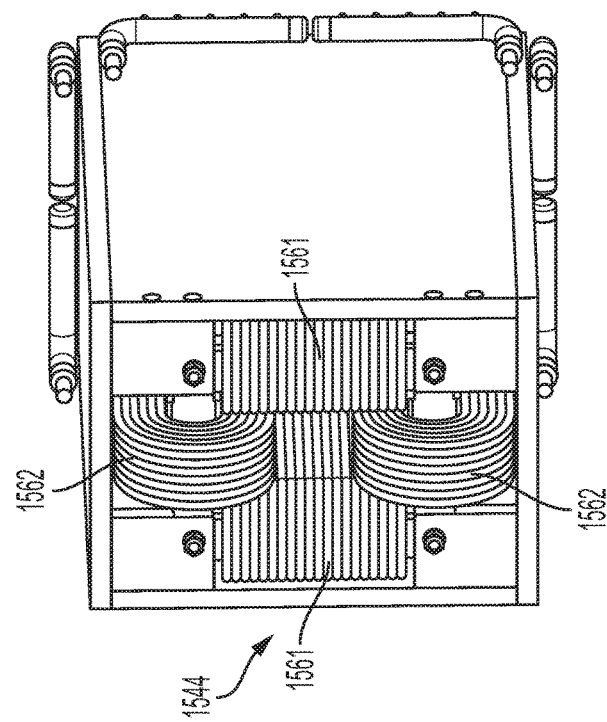
FIG. 45 is a perspective view of an example scanning magnet that may be part of the scanning components.
Figure 44:
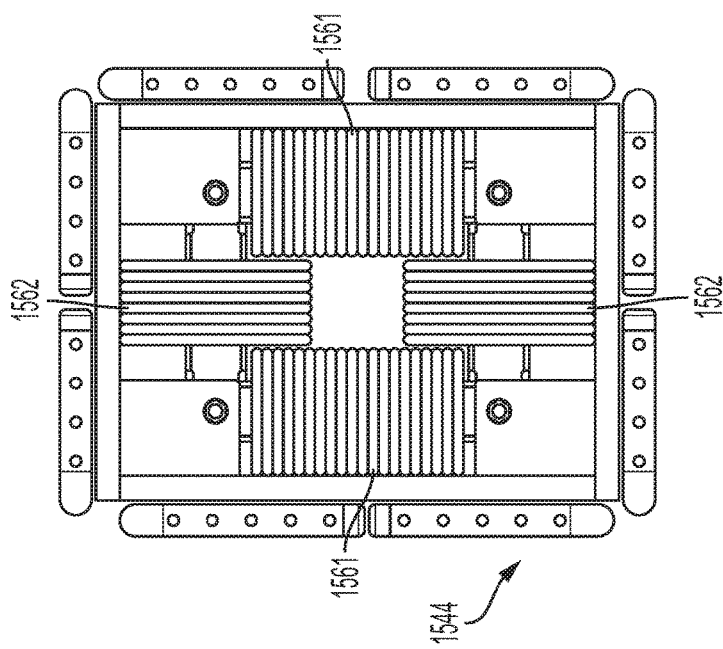
FIG. 44 is a side view of an example scanning magnet that may be part of the scanning components.

FIGS. 44 and 45 show views of an example scanning magnet 1544. In this example implementation, scanning magnet 1544 includes two coils 1561, which control particle beam movement in the X direction, and two coils 1562, which control particle beam movement in the Y direction. Control is achieved, in some implementations, by varying current through one or both sets of coils to thereby vary the magnetic field(s) produced thereby. By varying the magnetic field(s) appropriately, the particle beam can be moved in the X and/or Y direction across the irradiation target. The scanning magnet(s) may be leveraged to control the location and/or direction of the particle beam in the treatment processes described herein.

In some implementations, the scanning magnet rotates along with the particle accelerator. In some implementations, the scanning magnet is not movable physically relative to the particle accelerator. In some implementations, the scanning magnet may be movable physically relative to the particle accelerator (e.g., in addition to the movement provided by the gantry). In some implementations, the scanning magnet may be controllable to move the particle beam continuously so that there is uninterrupted motion of the particle beam over at least part of, and possibly all of, a layer of an irradiation target being scanned. In some implementations, the scanning magnets are controllable at intervals or specific times. In some implementations, there may be two or more different scanning magnets to position the particle beam, and to control all or part movement of a particle beam in the X and/or Y directions during scanning. In some implementations, scanning magnet 1544 may have an air core, a ferromagnetic (e.g., an iron) core, or a core that is a combination of air and ferromagnetic material.

During motion, the scanning magnet is subjected to the same gravitational forces as the superconducting magnet used for particle acceleration. That is, the coils of the scanning magnet may move and, thus, be displaced relative to their intended (predefined) position. The coil positioning system described herein may be used to move coil(s) of the scanning magnet(s) to correct or compensate for undesired movement of the scanning magnet(s) resulting from rotation. For example, the coil positioning system may be used to move the coil(s) to their original, intended positions or to any appropriate position that will achieve an intended magnetic field distribution—which may, or may not be, the original position of the coil(s).

Referring back to FIG. 42, a current sensor 1547 may be connected to, or be otherwise associated with, scanning magnet 1544. For example, the current sensor may be in communication with, but not connected to, the scanning magnet. In some implementations, the current sensor samples current applied to the magnet, which may include current to the coil(s) for controlling beam scanning in the X direction and/or current to the coil(s) for controlling beam scanning in the Y direction. During operation, the magnitude(s) (e.g., value(s)) of the magnet current(s) may be stored for each location at which a dose is delivered, along with the amount (e.g., intensity) of the dose. A computer system, which may be either on the accelerator or remote from the accelerator and which may include memory and one or more processing devices, may correlate the magnet current to coordinates within the radiation target, and those coordinates may be stored along with the amount of the dose. For example, the location may be identified by depth-wise layer number and Cartesian XY coordinates or by Cartesian XYZ coordinates (with the depth-wise layer corresponding to the Z coordinate). In some implementations, both the magnitude of the magnet current and the coordinate locations may be stored along with the dose at each location. The foregoing information may be stored in memory either on, or remote from, the accelerator. This information may be used during scanning to apply multiple doses of the same or of different amounts to the same locations to achieve target cumulative doses, including at areas of overlap between adjacent/sequential beam fields, as described herein.

In some implementations, the scanning system is run open loop, in which case, by controlling the scanning magnet(s), the particle beam is moved freely and uninterrupted across an irradiation target so as to substantially cover the target with radiation. As the radiation is delivered, the dosimetry controlled by the particle therapy control system records (e.g., stores) the amount of the radiation per location and information corresponding to the location at which the radiation was delivered. The location at which the radiation was delivered may be recorded as coordinates or as one or more magnet current values, and the amount of the radiation that was delivered may be recorded as dosage in grays. Because the system is run open loop, the delivery of the radiation is not synchronized to the operation of the particle accelerator (e.g., to its radio frequency (RF) cycle). Locations on the target where insufficient dose has been deposited can be treated with the particle beam any appropriate number of times until a desired dosage is reached. Different treatments of the same location may be from the same beam angle (e.g., from the same projection/beam field) or from different beam angles (projections/beam fields) as is the case intensity-modulated proton therapy (IMPT) described herein.

Configurable collimator 1548 may be located down-beam of the scanning magnets and down-beam of the energy degrader, as shown in FIGS. 42 and 43. The configurable collimator may trim the particle beam on a spot-by-spot basis during movement of the particle beam during scanning. For example, the configurable collimator may include sets of leaves that face each other, and that are movable into and out of carriages to create an aperture shape. Parts of the particle beam that exceed the aperture shape are blocked, and do not pass to the patient. The parts of the beam that pass to the patient are at least partly collimated, thereby providing a beam with a relatively precise edge. In an example, each set of leaves in the configurable collimator is controllable to define an edge that is movable into a path of the particle beam such that a first part of the particle beam on a first side of the edge is blocked by the multiple leaves and such that a second part of the particle beam on a second side of the edge is not blocked by the multiple leaves. The leaves in each set are individually controllable during scanning to trim an area as small as a single spot, and can also be used to trim larger multi-spot areas.

Figure 30:
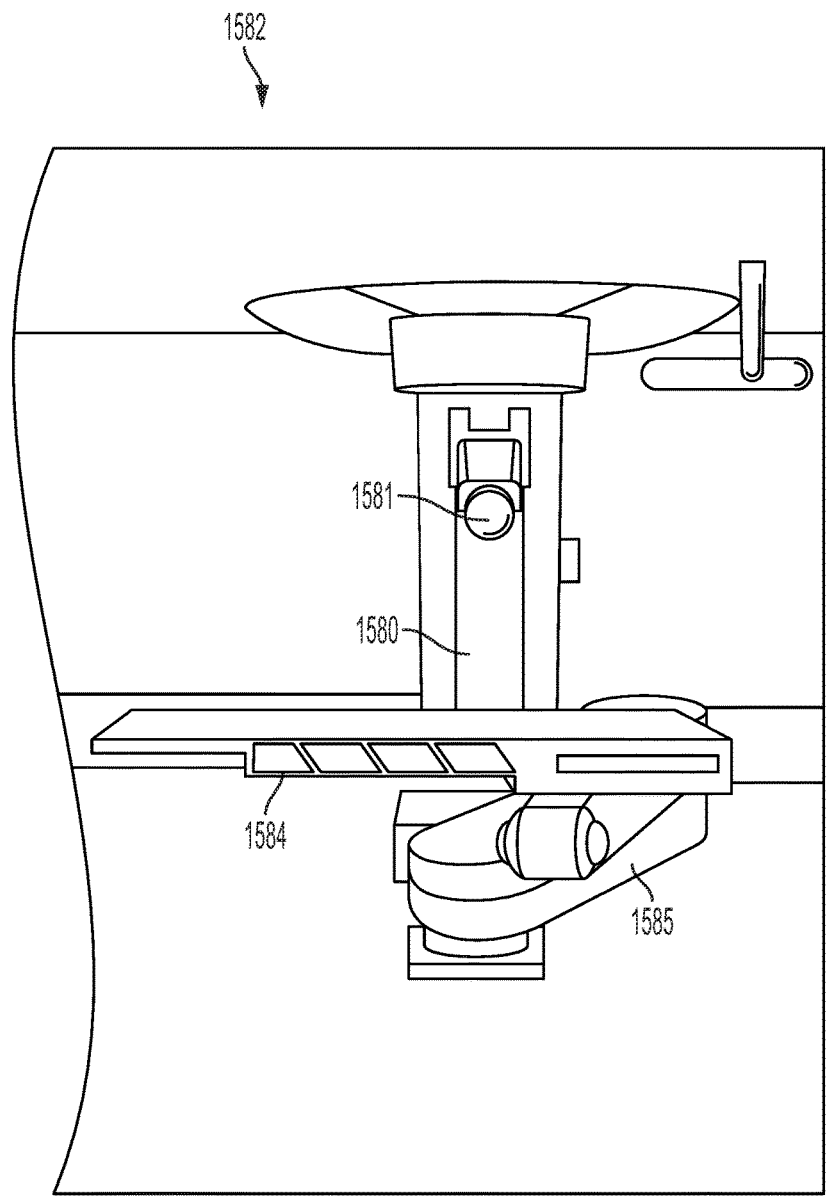
FIG. 30 is a front view of components of an example implementation of a particle therapy system from the perspective of a treatment space.
Figure 31:
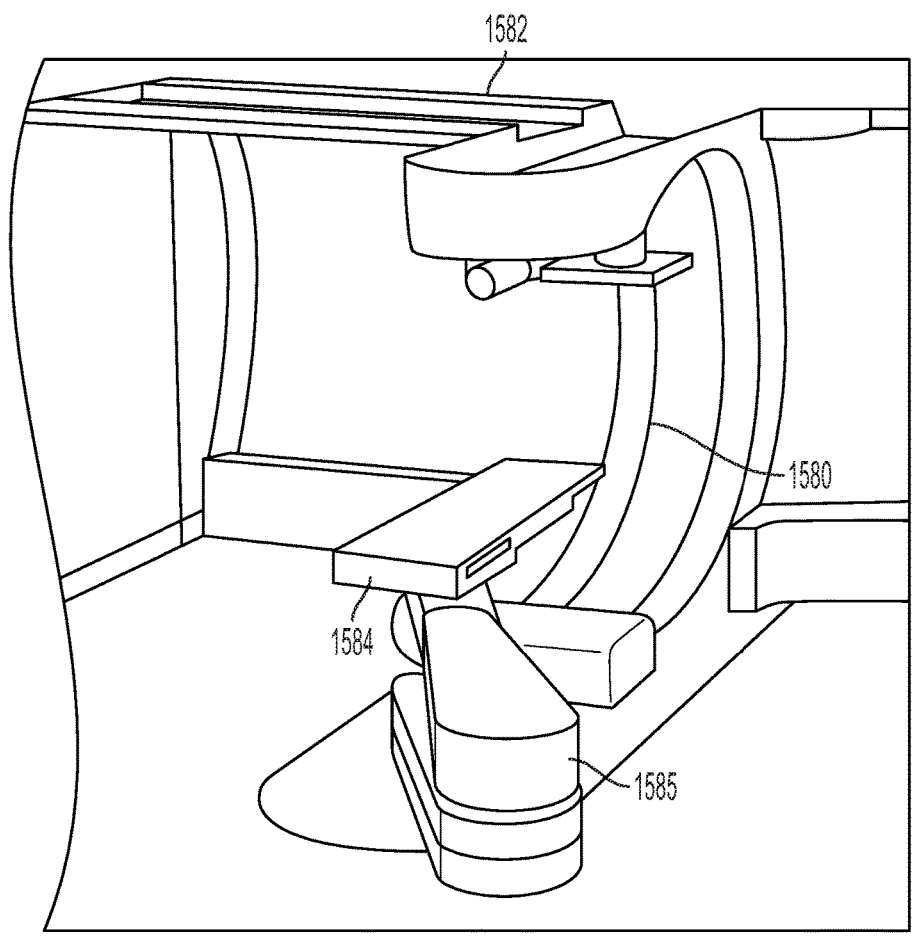
FIG. 31 is a perspective view of components of the particle therapy system of FIG. 30 from the perspective of a treatment space.

FIGS. 30 and 31 show parts an example of a particle therapy system 1582 containing a particle accelerator mounted on a gantry—in this example, a superconducting synchrocyclotron—that may use the coil positioning system described herein. In some implementations, the gantry is steel and has two legs (not shown) mounted for rotation on two respective bearings that lie on opposite sides of a patient. The gantry may be of the type described with respect to FIG. 1.

In the implementation of FIGS. 30 and 31, a patient is disposed on a treatment table 1584, which is controllable via arms 1585. The outer gantry (not shown) moves with inner gantry 1580, which positions nozzle 1581 to treat the patient. The nozzle, and any components mounted thereon, such as the configurable collimator, configure the beam for output.

Figure 32:
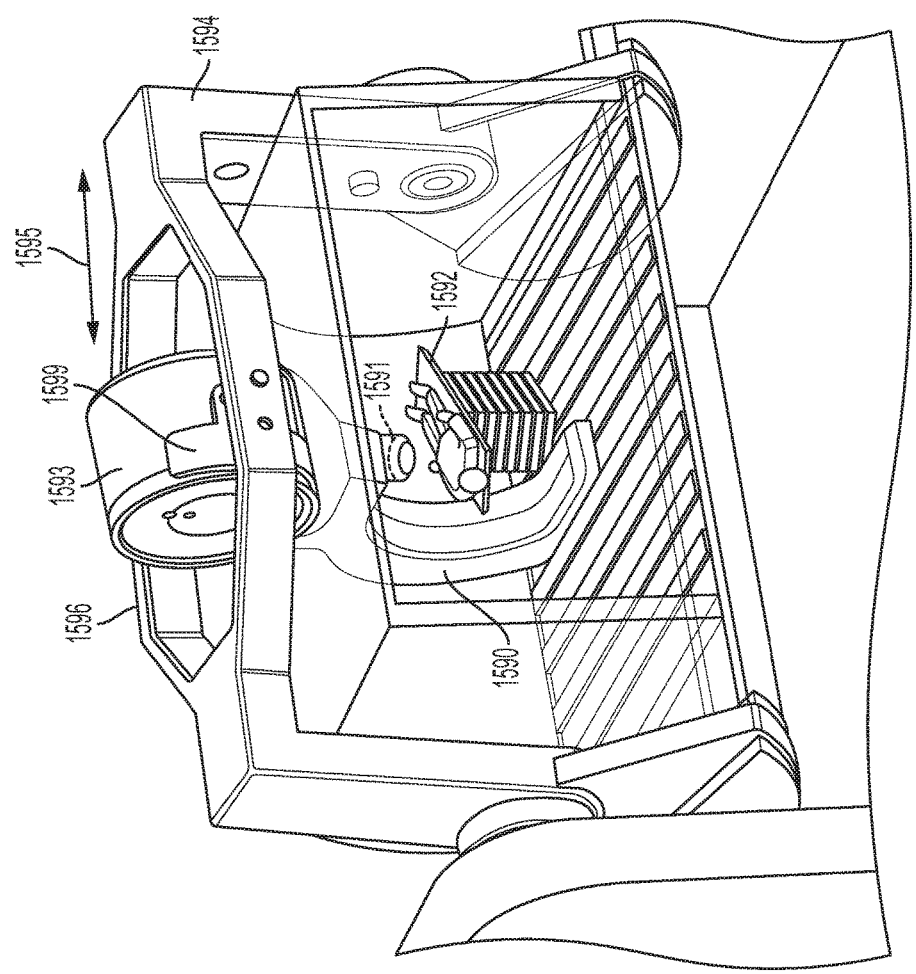
FIG. 32 is a front, perspective view of another example implementation of a particle therapy system from the perspective of a treatment space.

FIG. 32 shows an example of the gantry configuration described elsewhere herein, and includes components of an alternative implementation of a particle therapy system that is controllable in the manner described herein to implement treatment. The example particle therapy system of FIG. 32 includes an inner gantry 1590 having a nozzle 1591, a treatment couch 1592, and a particle accelerator 1593 (e.g., a synchrocyclotron of the type described herein) mounted on an outer gantry 1594 for rotation at least part-way around the patient to deliver radiation to target(s) in the patient. Treatment couch 1592 is controllable and configured to rotate and to translate the patient in the manner described herein.

In the example of FIG. 32, particle accelerator is also mounted to outer gantry 1594 also to enable linear movement (e.g., translational movement) of the particle accelerator in the directions of arrow 1595 along arms 1596. Thus, the accelerator is movable, relative to the treatment couch and thus the patient, from a first location along arms 1596, to a second location along arms 1596, to a third location along arms 1596, and so forth in order to position the accelerator, and thus the beam, for treatment. This translational movement may be controlled by the control system described herein, and used as an additional degree of freedom for positioning the particle beam in the particle therapy system described herein. Although single-dimensional translational movement (along arrow 1595) is shown in FIG. 37, the particle therapy system may be configured for two-dimensional translational movement, and/or three dimensional-translational movement as well (e.g., along the X, Y, and Z directions of a Cartesian coordinate system).

As also shown in FIG. 32, the particle accelerator 1593 may be connected to a gimbal 1599 for pivoting motion relative to the gantry. This pivoting motion may be used to position the accelerator, and thus the beam, for treatment. This pivoting movement may be controlled by the control system described herein, and may be used as one or more additional degrees of freedom for positioning the particle beam in the particle therapy system described herein. In some implementations, pivoting may enable the accelerator to move from a first orientation, to a second orientation, to a third orientation, and so forth during treatment. The particle accelerator may be mounted to enable pivoting relative to the patient in one, two, and/or three dimensions.

The types of accelerator movement achievable by the system of FIG. 32 may result in magnet coil displacement. Accordingly, the coil positioning system described herein may be incorporated into the system of FIG. 32 and used to move the magnet coils to correct for such displacement.

As described herein, in some implementations, rather than mounting the entire particle accelerator to the outer gantry (or other device), a scanning or other radiation-directing magnet alone may be mounted in lieu of, or in addition to, the accelerator, and may be moved relative to the irradiation target. The coil positioning system described herein may be used in implementations like this, to move the coils to correct for coil displacement.

Referring to FIGS. 30, 31, and 32, an inner gantry may be configured to move relative to the treatment couch to direct output of the beam toward the patient. In these examples, the inner gantry is C-shaped, and its movement coincides with movement of the outer gantry, on which the synchrocyclotron is mounted. As explained, the inner gantry includes a nozzle, on which one or more beamline components (e.g., the energy degrader and configurable collimator) are mounted to shape and otherwise adjust the beam. In some implementations, the inner gantry supports sub-millimeter beam positioning. In some implementations, there is no inner gantry, and all components described herein as being mounted on the inner gantry may be mounted to the accelerator or to the outer gantry.

Figure 33:
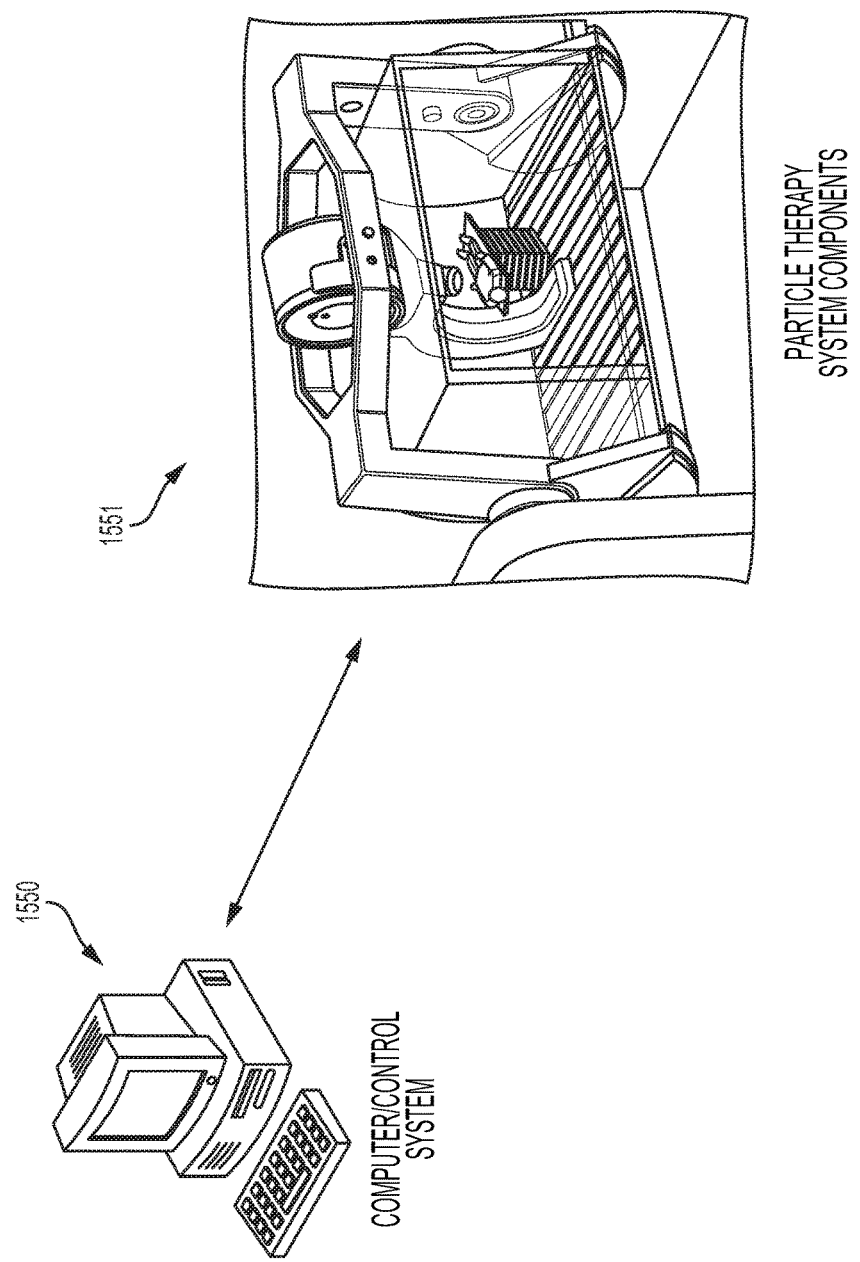
FIG. 33 is a system diagram depicting a control system and example particle therapy system components.

Referring to FIG. 33, control of a particle therapy system 1551 described herein may include, but is not limited to, control over accelerator movement and control over operation of the coil positioning system, including the actuators described herein. Such control may implemented by a control system 1550. Control system 1550 may include one or more computer systems as described herein and/or other control electronics. For example, control of the particle therapy system and its various components may be implemented using hardware or a combination of hardware and software. For example, a system like the ones described herein may include various controllers and/or processing devices located at various points, e.g., a controller or other type of processing device may be embedded in each controllable device or system. A central computer may coordinate operation among the various controllers or other types of processing devices. The central computer, controllers, and/or processing devices may execute various software routines to effect control and coordination of testing, calibration, and particle therapy treatment.

Operation of the example particle therapy systems described herein, and operation of all or some component thereof, can be controlled (as appropriate), at least in part, using one or more computer program products, e.g., one or more computer programs tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the operations of the example particle therapy systems described herein can be performed by one or more programmable processors executing one or more computer programs to perform the functions described herein. All or part of the operations can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any "electrical connection" as used herein may imply a direct physical connection or a wired or wireless connection that includes intervening components but that nevertheless allows electrical signals to flow between connected components. Any "connection" involving electrical circuitry that allows signals to flow, unless stated otherwise, is an electrical connection and not necessarily a direct physical connection regardless of whether the word "electrical" is used to modify "connection".

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

In some implementations, the synchrocyclotron used in the particle therapy system described herein may be a variable-energy synchrocyclotron. In some implementations, a variable-energy synchrocyclotron is configured to vary the energy of the output particle beam by varying the magnetic field in which the particle beam is accelerated. An example of a variable-energy synchrocyclotron that may be used is described with respect to FIGS. 25 to 28. For example, the current may be set to any one of multiple values to produce a corresponding magnetic field. In an example implementation, one or more sets of superconducting coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In some implementations, some sets of coils, such as the set for the fixed electrical current, are superconducting, while other sets of coils, such as the one or more sets for the variable current, are non-superconducting (e.g., copper) coils. The coil positioning system described herein, including the coil positioning actuators, may be used to move both the coils that received the fixed electrical current and the coils that received the variable electrical current. An example of a variable-energy synchrocyclotron that may be used in the example particle therapy systems is described in U.S. Patent Publication No. 2014/0371511 entitled "Particle Accelerator That Produces Charged Particles Having Variable Energies", the contents of which are incorporated herein by reference.

In some implementations, a particle accelerator other than a synchrocyclotron may be used in the particle therapy system described herein. For example, a cyclotron, a synchrotron, a linear accelerator, or the like may be substituted for the synchrocyclotron described herein. Although a rotational gantry has been described (e.g., the outer gantry), the example particle therapy systems described herein are not limited to use with rotational gantries. Rather, a particle accelerator may be mounted, as appropriate, on any type of robotic or other controllable mechanism(s)—characterized herein also as types of gantries—to implement movement of the particle accelerator. For example, the particle accelerator and/or a beam spreader may be mounted on or more robotic arms to implement rotational, pivotal, and/or translational movement of the accelerator and/or the spreader relative to the patient. The coil positioning system described herein, including the coil positioning actuators, may be used to move the coils of these other example particle accelerators under appropriate circumstances.

In some implementations, the particle accelerator itself may not move relative to the patient, as described herein. For example, in some implementations, the particle accelerator may be a stationary machine or at least not mounted for movement relative the patient. In examples like this, the particle accelerator may output its particle beam from the extraction channel to a transmission channel. The transmission channel may include magnets and the like for controlling magnetic fields contained therein in order to transport the particle beam to one or more remote locations, such as one or more treatment rooms. In each treatment room, the transmission channel may direct the beam to a beam spreader or other apparatus that is mounted for movement as described herein (e.g., to an outer gantry or other device). An example beam spreader may be, or include, a scanning magnet of the type described with respect to FIGS. 44 and 45. The coil positioning system described herein, including the coil positioning actuators, may be used to move one or more coils of the beam spreader to account for unwanted or unexpected motion during rotation. For example, the coil positioning system may be used to move the coil(s) to their original, intended positions or to any appropriate position that will achieve an intended magnetic field distribution—which may, or may not be, the original position of the coil(s). In some implementations, the coils can be moved to their expected (e.g., predefined) position, reducing the chances of treatment errors resulting from the spreader.

In some implementations, factors other than movement of the magnet may result in an unintended or unwanted magnetic field distribution. For example, temperature may affect the conductivity of current through the magnet, which may affect the magnet's resulting magnetic field distribution. For example, environmental humidity may affect the conductivity of current through the magnet, which may affect the magnet's resulting magnetic field distribution. For example, gases present in the environment may affect the conductivity of current through the magnet, which may affect the magnet's resulting magnetic field distribution. The coil positioning system described herein may be used to compensate for (e.g., to correct) an unwanted or undesirable magnetic field distribution resulting from factors such as these either alone or in combination with an unwanted or undesirable magnetic field distribution resulting from coil movement. That is, the coil positioning system may move the magnet coil(s), as described herein, so that the coil(s) produce a desired magnetic field distribution or at least approximate the desired magnetic field distribution as closely as possible or to an acceptable degree under the circumstances. The coil positioning system may operate as described herein to sense the magnetic field distribution and move the coil(s) as appropriate. Other sensors, such as temperature, humidity, and gas sensors may inform the determination (e.g., by a processing device) of the magnetic field distribution.

An example implementation of a particle therapy system in which the coil positioning systems described herein may be implemented is described in U.S. Pat. No. 7,728,311 entitled "Charged Particle Radiation Therapy", the contents of which are incorporated herein by reference. The content incorporated by reference includes, but is not limited to, the description of the synchrocyclotron and the gantry system holding the synchrocyclotron found in U.S. Pat. No. 7,728,311.

Other implementations not specifically described herein are also within the scope of the following claims.

What is claimed is:

1. A system comprising:
a magnet comprising one or more coils to conduct current to generate a magnetic field, the magnetic field to affect output of radiation to a target; and
one or more actuators, an actuator among the one or more actuators being at least part of a physical coupling to the one or more coils, the actuator being controllable to move the one or more coils via the physical coupling based on movement of the magnet.

2. The system of claim 1, further comprising:
a housing that at least partly encloses the magnet;
wherein movement of the magnet causes the one or more coils to move relative to the housing in a first direction; and
wherein the one or more actuators are controllable to move the one or more coils relative to the housing in a second direction that is substantially opposite to the first direction in response to movement of the one or more coils in the first direction.

3. The system of claim 1, further comprising:
a housing that borders the magnet;
wherein movement of the magnet causes the one or more coils to move relative to the housing; and
wherein the one or more actuators are controllable to move the one or more coils relative to the housing to compensate, at least partly, for movement of the one or more coils relative to the housing caused by movement of the magnet.

4. The system of claim 1, further comprising:
a housing that holds the magnet;
wherein the magnet is movable from a first orientation to a second orientation, the movement of the magnet causing the one or more coils to move from a first position relative to the housing at the first orientation to a second position relative to the housing at the second orientation; and
wherein the one or more actuators are controllable to move the one or more coils so that the one or more coils are at the first position relative to the housing when the housing is at the second orientation.

5. The system of claim 1, wherein the magnet comprises a support structure to hold the one or more coils; and
wherein the physical coupling comprises the support structure, the actuator being configured to move the one or more coils by moving the support structure.

6. The system of claim 5, further comprising:
a vacuum enclosure around the magnet;
wherein the physical coupling comprises a strap connected between the actuator and the support structure; and
wherein the actuator is connected to the vacuum enclosure and to the strap, the actuator being configured to increase tension on the strap to move the one or more coils.

7. The system of claim 6, wherein the actuator comprises a differential screw that connects to the strap, and the actuator comprises a motor connected to drive the differential screw to increase tension on the strap.

8. The system of claim 1, wherein the actuator is controllable to move the one or more coils via the physical coupling based on movement of the magnet in order to achieve a target magnetic field distribution.

9. The system of claim 6, wherein the magnet is a superconducting magnet;
wherein the system further comprises a cryostat to maintain the one or more coils at temperatures that enable superconductivity in the one or more coils, the cryostat including the support structure.

10. The system of claim 1, wherein the one or more actuators comprise a group of actuators, each actuator in the group being at least part of a separate physical coupling to the one or more coils, each actuator in the group being controllable to move the one or more coils via a respective physical coupling based on movement of the magnet.

11. The system of claim 10, further comprising:
an enclosure that houses the magnet;
wherein the group of actuators are mounted inside an external perimeter of the enclosure, each actuator being configured to pull the one or more coils at least partly inwards towards an interior of the external perimeter.

12. The system of claim 10, further comprising:
an enclosure that houses the magnet;
wherein each actuator in the group of actuators is configured to pull the one or more coils at least partly outwards relative to an external perimeter of the enclosure.

13. The system of claim 10, further comprising:
an enclosure that houses the magnet;
wherein the group of actuators are mounted in a symmetric arrangement on the enclosure and are controllable to act in concert.

14. The system of claim 1, further comprising:
an enclosure that at least partly surrounds the magnet;
wherein the system comprises:
one or more sensors to detect movement of the one or more coils relative to the enclosure, the actuator being controllable based on detection of the movement of the one or more coils relative to the enclosure.

15. The system of claim 14, wherein the one or more sensors comprises one or more magnetic field sensors mounted to the enclosure, the one or more magnetic field sensors being configured to detect a change in the magnetic field generated by the one or more coils relative to the one or more magnetic field sensors, the detected change in the magnetic field being indicative of the movement of the one or more coils relative to the enclosure.

16. The system of claim 14, wherein the one or more sensors comprises one or more displacement sensors mounted to the enclosure to obtain measurements based on positions of the one or more coils; and
wherein the system comprises one or more processing devices to determine the movement of the one or more coils based on the measurements.

17. The system of claim 1, further comprising:
a particle accelerator, the magnet being part of the particle accelerator, the particle accelerator being configured for movement, wherein the magnet is configured for movement as a result of the magnet being part of the particle accelerator.

18. The system of claim 17, wherein the particle accelerator is a synchrocyclotron, the magnet is a superconducting magnet, and the system further comprises:
a gantry on which the particle accelerator is mounted to produce the movement of the particle accelerator and of the magnet.

19. The system of claim 1, wherein the radiation comprises a particle beam, and wherein current in the one or more coils is controllable to affect the particle beam prior to application to an irradiation target.

20. The system of claim 19, wherein the current is controllable to direct the particle beam to one or more points in the irradiation target.

21. The system of claim 19, wherein the current is controllable to focus the particle beam prior to output to the irradiation target.

22. A particle therapy system comprising:
- a magnet comprising one or more coils to conduct current to generate a magnetic field, the magnetic field to affect output of a particle beam;
- a housing to hold the magnet;
- a mount to which the housing is connected to enable movement of the housing, the movement causing a displacement of the one or more coils relative to the housing; and
- one or more actuators that are part of a physical coupling to the one or more coils, the one or more actuators being controllable to move, via the physical coupling, the one or more coils relative to the housing to at least partly correct the displacement.

23. The particle therapy system of claim 22, wherein two or more of the actuators are controllable to act in concert to move the one or more coils.

24. The particle therapy system of claim 22, wherein the displacement occurs along a first direction, and the one or more actuators are controllable to move the one or more coils in a second direction that is substantially opposite to the first direction.

25. The particle therapy system of claim 22, wherein the one or more actuators are controllable to move the one or more coils in real-time during movement of the housing.

26. The particle therapy system of claim 22, wherein the one or more actuators are controllable to move the one or more coils following the movement of the housing that caused the displacement.

27. The particle therapy system of claim 22, wherein the magnet comprises a support structure to hold the one or more coils; and
- wherein the physical coupling comprises the support structure, the one or more actuators being configured to move the coil by moving the support structure physically.

28. The system of claim 27, wherein, for an actuator among the one or more actuators, a physical coupling comprises a strap connected between the actuator and the support structure; and
- wherein the actuator is connected to the housing and to the strap, the actuator being configured to increase tension on the strap to move the one or more coils.

29. The system of claim 28, wherein the actuator comprises a differential screw that connects to the strap, and the actuator comprises a motor connected to drive the differential screw to increase tension on the strap.

30. The system of claim 22, wherein the one or more actuators are controllable to move the one or more coils via the physical coupling based on movement of the magnet in order to achieve a target magnetic field distribution.

31. The system of claim 27, wherein the magnet is a superconducting magnet;
- wherein the system further comprises a cryostat to maintain the one or more coils at temperatures that enable superconductivity in the one or more coils, the cryostat including the support structure.

32. The system of claim 22, wherein the one or more actuators comprise a group of actuators, each actuator in the group being at least part of a separate physical coupling to the one or more coils, each actuator in the group being controllable to move the one or more coils via a respective physical coupling.

33. The system of claim 32, wherein the group of actuators are mounted inside of an exterior perimeter of the housing, each actuator being configured to pull the one or more coils at least partly inwards towards an interior of the exterior perimeter.

34. The system of claim 32, wherein each actuator in the group of actuators is configured to pull the one or more coils at least partly outwards relative to an exterior perimeter of the housing.

35. The system of claim 32, wherein the group of actuators are mounted in a symmetric arrangement on the housing and are controllable to act in concert.

36. The system of claim 22, further comprising:
- one or more sensors to detect movement of the one or more coils relative to the housing, the one or more actuators being controllable based on detection of the movement of the one or more coils relative to the housing.

37. The system of claim 36, wherein the one or more sensors comprises one or more magnetic field sensors mounted to the housing, the one or more magnetic field sensors being configured to detect a change in the magnetic field generated by the one or more coils relative to the one or more magnetic field sensors, the detected change in the magnetic field being indicative of the movement of the one or more coils relative to the housing.

38. The system of claim 36, wherein the one or more sensors comprises one or more displacement sensors mounted to the housing to obtain measurements based on the positions of the one or more coils; and
- wherein the system comprises one or more processing devices to determine the movement of the one or more coils based on the measurements.

39. The system of claim 22, further comprising:
- a particle accelerator, the magnet and the housing being part of the particle accelerator, the particle accelerator being configured for movement that is at least partly rotational, wherein the magnet and the housing are configured for movement as a result of the magnet and the housing being part of the particle accelerator.

40. The system of claim 39, wherein the particle accelerator is a synchrocyclotron, the magnet is a superconducting magnet, and the mount comprises a rotatable gantry on which the particle accelerator is mounted.

41. The system of claim 22, wherein the current in the one or more coils is controllable to affect the particle beam prior to application to an irradiation target.

42. The system of claim 22, wherein the current is controllable to direct the particle beam to one or more points in the irradiation target.

43. The system of claim 22, wherein the current is controllable to focus the particle beam prior to output to the irradiation target.

44. A system comprising:
- means for rotating a magnet, the magnet comprising one or more coils to conduct current to generate a magnetic field, wherein movement of the magnet causes displacement of the one or more coils away from a predefined position; and
- means for physically moving the one or more coils so that, following movement of the magnet, the one or more coils are in the predefined position.

45. A system comprising:
- a magnet comprising one or more coils to conduct current to generate a magnetic field; and one or more actuators, an actuator among the one or more actuators being at least part of a physical coupling to the one or more coils, the actuator being controllable to move the one or more coils via the physical coupling to arrive at a target distribution of the magnetic field.

46. The system of claim 45, further comprising:
one or more sensors to detect movement of the one or more coils relative to a reference, the actuator being controllable based on detection of the movement of the one or more coils relative to the reference.

47. The system of claim 46, wherein the one or more sensors comprises one or more magnetic field sensors, the one or more magnetic field sensors being configured to detect a change in the magnetic field generated by the one or more coils relative to the one or more magnetic field sensors, the detected change in the magnetic field being indicative of the movement of the one or more coils.

48. The system of claim 46, wherein the one or more sensors comprises one or more displacement sensors to obtain measurements based on positions of the one or more coils; and
wherein the system comprises one or more processing devices to determine the movement of the one or more coils based on the measurements.

49. The system of claim 45, further comprising:
a particle accelerator, the magnet being part of the particle accelerator, the particle accelerator being configured for movement, wherein the magnet is configured for movement as a result of the magnet being part of the particle accelerator.

50. The system of claim 49, wherein the particle accelerator is a synchrocyclotron, the magnet is a superconducting magnet, and the system further comprises:
a gantry on which the particle accelerator is mounted to produce the movement of the particle accelerator and of the magnet.

51. The system of claim 49, wherein the magnet is configured to accelerate particles in a cavity of the particle accelerator to produce a particle beam.

52. The system of claim 49, wherein the magnet is configured to focus particles during extraction of a particle beam from the particle accelerator.

53. The system of claim 49, wherein the magnet is configured to control movement of a particle beam output from the particle accelerator relative to a target of the particle beam.

* * * * *